United States Patent
Eckhardt et al.

(10) Patent No.: US 9,090,605 B2
(45) Date of Patent: Jul. 28, 2015

(54) SUBSTITUTED 5-, 6- AND 7-MEMBERED HETEROCYCLES, MEDICAMENTS CONTAINING SUCH COMPOUNDS, AND THEIR USE

(71) Applicants: Vitae Pharmaceuticals, Inc., Fort Washington, PA (US); Boehringer Ingelheim International GmbH, Ingelheim Am Rhein (DE)

(72) Inventors: Matthias Eckhardt, Biberach an der Riss (DE); Frank Himmelsbach, Mittelbiberach (DE); Katerina Leftheris, San Diego, CA (US); Suresh B. Singh, Kendall Park, NJ (US); Colin M. Tice, Ambler, PA (US); Zhenrong Xu, Chalfont, PA (US); Yuanjie Ye, Ambler, PA (US); Linghang Zhuang, Chalfont, PA (US)

(73) Assignees: Vitae Pharmaceuticals, Inc., Fort Washington, PA (US); Boehringer-Ingelheim International GmbH (DE)

( * ) Notice: Subject to any disclaimer, the term of this patent is extended or adjusted under 35 U.S.C. 154(b) by 0 days.

(21) Appl. No.: 14/497,782

(22) Filed: Sep. 26, 2014

(65) Prior Publication Data
US 2015/0080363 A1  Mar. 19, 2015

Related U.S. Application Data

(62) Division of application No. 13/703,708, filed as application No. PCT/US2011/040443 on Jun. 15, 2011, now Pat. No. 8,933,072.

(60) Provisional application No. 61/355,458, filed on Jun. 16, 2010.

(51) Int. Cl.
| | |
|---|---|
| C07D 239/04 | (2006.01) |
| C07D 401/10 | (2006.01) |
| C07D 239/34 | (2006.01) |
| C07D 417/14 | (2006.01) |
| C07D 413/10 | (2006.01) |
| C07D 413/14 | (2006.01) |

(52) U.S. Cl.
CPC ............ *C07D 417/14* (2013.01); *C07D 413/10* (2013.01); *C07D 413/14* (2013.01)

(58) Field of Classification Search
CPC ... C07D 239/04; C07D 401/10; C07D 239/34
USPC .......................................... 544/315; 514/269
See application file for complete search history.

(56) References Cited

U.S. PATENT DOCUMENTS

| | | |
|---|---|---|
| 3,341,538 A | 9/1967 | Block et al. |
| 3,378,587 A | 4/1968 | Reinhardt |
| 3,681,349 A | 8/1972 | Schwan et al. |
| 3,703,529 A | 11/1972 | Cavalla et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |

(Continued)

FOREIGN PATENT DOCUMENTS

| | | |
|---|---|---|
| DE | 1801556 A1 | 5/1970 |
| DE | 2105743 A1 | 8/1972 |

(Continued)

OTHER PUBLICATIONS

Suga, Seiji et al., ""N-Acyliminium Ion Pool" as a Heterodiene in [4+] Cycloaddition Reaction", Organic Letters, 2003, vol. 5, pp. 945-947.

Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.

(Continued)

*Primary Examiner* — Kahsay Habte
(74) *Attorney, Agent, or Firm* — McCarter & English LLP; Steven G. Davis; Michael J. DeGrazia

(57) ABSTRACT

Disclosed are compounds represented by Formula (I):

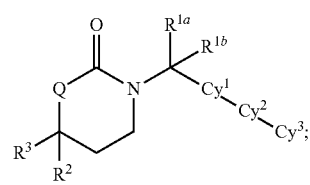

or pharmaceutically acceptable salts, enantiomers or diastereomers thereof. Also disclosed are pharmaceutical compositions comprising the compounds of Formula (I) or pharmaceutically acceptable salts, enantiomers or diastereomers thereof for the therapeutic treatment of diseases associated with the modulation or inhibition of 11β-HSD1 in mammals. Values for the variables of Formula (I) are defined herein.

17 Claims, No Drawings

(56) References Cited

U.S. PATENT DOCUMENTS

| | | |
|---|---|---|
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,145,103 A | 11/2000 | Typaldos et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 8,569,292 B2 | 10/2013 | Claremon et al. |
| 8,575,156 B2 | 11/2013 | Claremon et al. |
| 8,592,410 B2 | 11/2013 | Claremon et al. |
| 8,598,160 B2 | 12/2013 | Claremon et al. |
| 8,598,163 B2 | 12/2013 | Claremon et al. |
| 8,673,899 B2 | 3/2014 | Claremon et al. |
| 8,680,281 B2 | 3/2014 | Claremon et al. |
| 8,835,426 B2 | 9/2014 | Claremon et al. |
| 8,846,668 B2 | 9/2014 | Himmelsbach et al. |
| 8,927,539 B2 | 1/2015 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0019643 A1 | 1/2011 | Kim et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2108954 A1 | 9/1972 |
| DE | 2229695 A1 | 1/1974 |
| DE | 2338369 A1 | 2/1975 |
| DE | 2354002 A1 | 5/1975 |
| DE | 2411382 A1 | 9/1975 |
| DE | 2437610 A1 | 2/1976 |
| DE | 2828039 A1 | 1/1980 |
| DE | 19918725 A1 | 10/2000 |
| DE | 19929348 A1 | 12/2000 |
| DE | 10034623 A1 | 1/2002 |
| EP | 0415642 A1 | 3/1991 |
| EP | 0454444 A1 | 10/1991 |
| EP | 0471591 A2 | 2/1992 |
| EP | 0640594 A1 | 3/1995 |
| EP | 0645387 A1 | 3/1995 |
| EP | 0847275 A1 | 6/1998 |

(56) References Cited

FOREIGN PATENT DOCUMENTS

| | | |
|---|---|---|
| EP | 0928789 A1 | 7/1999 |
| EP | 1156049 A1 | 11/2001 |
| EP | 1270724 A2 | 1/2003 |
| EP | 1801098 A1 | 6/2007 |
| EP | 1852425 A1 | 11/2007 |
| EP | 1864971 A1 | 12/2007 |
| EP | 1935420 A1 | 6/2008 |
| FR | 2796940 A1 | 2/2001 |
| GB | 1077711 A | 8/1967 |
| JP | 6092945 A | 4/1994 |
| JP | 7157681 A | 6/1995 |
| JP | 09151179 A | 6/1997 |
| JP | 2002179572 A | 6/2002 |
| JP | 2003096058 A | 4/2003 |
| JP | 2003300884 A | 10/2003 |
| JP | 2005-206503 A | 8/2005 |
| JP | 2005239670 A | 9/2005 |
| JP | 2005272321 A | 10/2005 |
| JP | 2007140188 A | 6/2007 |
| JP | 2007254409 A | 10/2007 |
| JP | 2009110842 A | 5/2009 |
| JP | 2011519374 A | 7/2011 |
| WO | 92/07838 A1 | 5/1992 |
| WO | 93/07128 A1 | 4/1993 |
| WO | 93/13103 A1 | 7/1993 |
| WO | 95/12591 A1 | 5/1995 |
| WO | 95/31440 A1 | 11/1995 |
| WO | 96/14297 A1 | 5/1996 |
| WO | 96/23787 A1 | 8/1996 |
| WO | 96/37494 A1 | 11/1996 |
| WO | 97/07789 A1 | 3/1997 |
| WO | 97/36605 A1 | 10/1997 |
| WO | 98/22462 A1 | 5/1998 |
| WO | 98/52940 A1 | 11/1998 |
| WO | 98/57940 A1 | 12/1998 |
| WO | 99/05125 A1 | 2/1999 |
| WO | 99/06395 A1 | 2/1999 |
| WO | 00/09107 A2 | 2/2000 |
| WO | 01/00595 A1 | 1/2001 |
| WO | 01/13917 A1 | 3/2001 |
| WO | 01/44200 A2 | 6/2001 |
| WO | 01/55063 A1 | 8/2001 |
| WO | 02/06244 A1 | 1/2002 |
| WO | 02/06277 A1 | 1/2002 |
| WO | 02/22572 A2 | 3/2002 |
| WO | 03/043988 A1 | 5/2003 |
| WO | 03/057673 A1 | 7/2003 |
| WO | 03/093261 A1 | 11/2003 |
| WO | 03/097608 A2 | 11/2003 |
| WO | 2004/004722 A1 | 1/2004 |
| WO | 2004/009559 A2 | 1/2004 |
| WO | 2004/014859 A2 | 2/2004 |
| WO | 2004/046137 A1 | 6/2004 |
| WO | 2004/056745 A2 | 7/2004 |
| WO | 2004/089896 A1 | 10/2004 |
| WO | 2004/094375 A2 | 11/2004 |
| WO | 2005/000845 A2 | 1/2005 |
| WO | 2005/086700 A2 | 9/2005 |
| WO | 2005/108360 A1 | 11/2005 |
| WO | 2005/108361 A1 | 11/2005 |
| WO | 2005/113525 A1 | 12/2005 |
| WO | 2005/116002 A2 | 12/2005 |
| WO | 2006/002349 A1 | 1/2006 |
| WO | 2006/003494 A2 | 1/2006 |
| WO | 2006/014357 A1 | 2/2006 |
| WO | 2006/017443 | 2/2006 |
| WO | 2006/024627 A2 | 3/2006 |
| WO | 2006/024628 A1 | 3/2006 |
| WO | 2006/031715 A2 | 3/2006 |
| WO | 2006/040329 A1 | 4/2006 |
| WO | 2006/044174 A2 | 4/2006 |
| WO | 2006/049952 A1 | 5/2006 |
| WO | 2006/066924 A2 | 6/2006 |
| WO | 2006/066948 A1 | 6/2006 |
| WO | 2006/090792 A1 | 8/2006 |
| WO | 2006/104280 A1 | 10/2006 |
| WO | 2006/109056 A1 | 10/2006 |
| WO | 2007/008529 A2 | 1/2007 |
| WO | 2007/022371 A2 | 2/2007 |
| WO | 2007/048595 A1 | 5/2007 |
| WO | 2007/051810 A2 | 5/2007 |
| WO | 2007/061661 A2 | 5/2007 |
| WO | 2007/068330 A1 | 6/2007 |
| WO | 2007/076055 A2 | 7/2007 |
| WO | 2007/079186 A2 | 7/2007 |
| WO | 2007/081569 A2 | 7/2007 |
| WO | 2007/081570 A2 | 7/2007 |
| WO | 2007/081571 A2 | 7/2007 |
| WO | 2007/084314 A2 | 7/2007 |
| WO | 2007/101270 A1 | 9/2007 |
| WO | 2007/103719 A2 | 9/2007 |
| WO | 2007/109456 A2 | 9/2007 |
| WO | 2007/118185 A2 | 10/2007 |
| WO | 2007/123853 A2 | 11/2007 |
| WO | 2007/124254 A2 | 11/2007 |
| WO | 2007/124329 A1 | 11/2007 |
| WO | 2007/124337 A1 | 11/2007 |
| WO | 2007/127693 A1 | 11/2007 |
| WO | 2007/127763 A2 | 11/2007 |
| WO | 2008/000951 A2 | 1/2008 |
| WO | 2008/024497 A2 | 2/2008 |
| WO | 2008/031227 A1 | 3/2008 |
| WO | 2008/036715 A1 | 3/2008 |
| WO | 2008/046578 A2 | 4/2008 |
| WO | 2008/046758 A2 | 4/2008 |
| WO | 2008/059948 A1 | 5/2008 |
| WO | 2008/106128 A2 | 9/2008 |
| WO | 2008/118332 A2 | 10/2008 |
| WO | 2009/017664 A2 | 2/2009 |
| WO | 2009/017671 A1 | 2/2009 |
| WO | 2009/020140 A1 | 2/2009 |
| WO | 2009/061498 A1 | 5/2009 |
| WO | 2009/063061 A2 | 5/2009 |
| WO | 2009/075835 A1 | 6/2009 |
| WO | 2009/088997 A1 | 7/2009 |
| WO | 2009/094169 A1 | 7/2009 |
| WO | 2009/100872 A1 | 8/2009 |
| WO | 2009/102428 A2 | 8/2009 |
| WO | 2009/102460 A2 | 8/2009 |
| WO | 2009/107664 A1 | 9/2009 |
| WO | 2009/108332 A1 | 9/2009 |
| WO | 2009/117109 A1 | 9/2009 |
| WO | 2009/131669 A2 | 10/2009 |
| WO | 2009/134384 A1 | 11/2009 |
| WO | 2009/134387 A1 | 11/2009 |
| WO | 2009/134392 A1 | 11/2009 |
| WO | 2009/134400 A1 | 11/2009 |
| WO | 2009/138386 A2 | 11/2009 |
| WO | 2010/010149 A1 | 1/2010 |
| WO | 2010/010150 A1 | 1/2010 |
| WO | 2010/010157 A2 | 1/2010 |
| WO | 2010/010174 A1 | 1/2010 |
| WO | 2010/011314 A1 | 1/2010 |
| WO | 2010/023161 A1 | 3/2010 |
| WO | 2010/046445 A2 | 4/2010 |
| WO | 2010/089303 A1 | 8/2010 |
| WO | 2010/091067 A2 | 8/2010 |
| WO | 2010/104830 A1 | 9/2010 |
| WO | 2010/127237 A2 | 11/2010 |
| WO | 2010/139673 A1 | 12/2010 |
| WO | 2010/141424 A1 | 12/2010 |
| WO | 2011/002910 A1 | 1/2011 |
| WO | 2011/011123 A1 | 1/2011 |
| WO | 2011/031979 A1 | 3/2011 |
| WO | 2011/056737 A1 | 5/2011 |
| WO | 2011/057054 A1 | 5/2011 |
| WO | 2011/159760 A1 | 12/2011 |
| WO | 2011/161128 A1 | 12/2011 |
| WO | 2012/059416 A1 | 5/2012 |
| WO | 2012/061708 A1 | 5/2012 |

OTHER PUBLICATIONS

Tamaru et al., "Urea as the Most Reactive and Versatile Nitrogen Nucleophile for the Palladium(2+)-Catalyzed Cyclization of Unsat-

(56) References Cited

OTHER PUBLICATIONS urated Amines", Journal of the American Chemical Society, 1988, vol. 110, pp. 3994-4002.
Thiel (Nature Biotechnol 2:513-519, 2004).
Vippagunta, et al., "Crystalline Solids", Advanced Drug Deliver Reviews, 2001, vol. 48, pp. 3-26.
Yoshida, Masaaki et al., "Selective synthesis of five—and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
Zhurnal Organicheskoi Khimii, 1978, vol. 14(5), pp. 1092-1094.
CA 1267843-31-1, (Aug. 10, 2009).
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).
Office Action for U.S. Appl. No. 12/741,522 (U.S. Patent No. 8,138,178), date of mailing Dec. 15, 2010.
CA 154:284276, (Mar. 17, 2011).
Office Action dated Apr. 3, 2012 for corresponding U.S. Appl. No. 13/318,271.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Office Action dated May 3, 2012 for corresponding U.S. Appl. No. 13/347,799.
Office Action dated Jun. 14, 2012 for corresponding U.S. Appl. No. 13/347,784.
Database CA [Online], Chemical Abstracts Service, Fukushima et al., "Preparation of Imidazolidinone Derivatives as 11.beta.-HSD1 Inhibitors", 2007, XP 002531878.
Examiner Interview Summary dated May 2, 2011, in U.S. Appl. No. 12/741,522 (U.S. Patent No. 8,138,178).
Chalmers (TIPS vol. 17, pp. 166-172 Apr. 1996).
International Search Report for PCT/EP2009/063913 mailed May 6, 2010.
Gutkowska et al.: Acta Poloniae Pharmaceutica 1986, 43, p. 403-405.
Gutkowska et al.: Acta Polonaie Pharmaceutica 1987, 39, p. 411-414.
DeMarinis R.M. et.al. Journal of Medicinal Chemistry 1981, vol. 24, No. 12, pp. 1432-1437.
Rosenstock et.al. Diabetes Care Jul. 2010, LNKDPUBMED: 20413513, vol. 33, No. 7, pp. 1516-1522.
Vidic et al.: Chem. Ber. 1976, 109, p. 2657-2669.
Bosch et al.: Heterocycles 1980, 14, p. 1983-1988.
Ma et al.: Tetrahedron 2007, 63, p. 7523-7531.
Ma et al.: Synthesis 2007, p. 161-163.
Yokoyama et al.: J. Med. Chem. 1979, 22, p. 537-553.
Harno et.al. Trends in Endocrinology and Metabolism, Elsevier Science Publishing, New York 2010, vol. 21, No. 10, pp. 619-627.
Taddayon et.al. Expert opinion on Investigational Drugs, Ashley Publication Ltd. 2003, vol. 12, No. 3, pp. 307-324.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
Gutkowska et al.: Acta Poloniae Pharmaceutica, 1982, vol. 39, p. 61-64.
Olesen et al.: Current Opin Drug Dis Dev, 2001, vol. 4, No. 4, p. 471-478.
Thornber et al.: Chem Soc Rev, 1979, vol. 8, p. 563-580.
Caplus-133:4656—Anantanarayan, A. el. al., "Preparation of heteroarylpyrazoles as P38 kinase inhibitors". 2000.
Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
International Search Report and Written Opinion for PCT/US2012/050679 mailed Oct. 31, 2012.
International Search Report and Written Opinion for PCT/EP2009/059509, mailed Feb. 9, 2009.
Claremon et al. CAS: 150:214405, 2009.
Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.
Evans, B.E. et al., "Orally active, nonpeptide osytocin antagonists". Journal of Medicinal Chemistry, American Chem. Soc., Vo. 35, No. 21, Oct. 15, 1992, p. 3919-3927.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.
Aluri. B.R. et al., "Bulky n-Substituted 1,3-Benzazaphospholes: Access via Pd-Catalyzed C-N and C-P Cross Coupling, Lithiation, and Conversion to Novel P=C PtBu2 Hybrid Ligands". Inorganic Chemistry, 2008, 47, p. 6900-6912.
Aluri, B.R. et al., "Sterically and Polarity-Controlled Reactions of tBuLi with P=Ch-Nr Heterocycles: Novel Heterocyclic P-and P,O-Ligands and Preliminary Tests in Transition-Metal Catalysis", Chem. Eur. Journal, vol. 14, 2008, p. 4328-4335.
Fandrick, Dr. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.
International Search Report and Written Opinion for PCT/EP/2009/059496 mailed Nov. 17, 2009.
International Search Report and Written Opinion for PCT/EP2010/051262 mailed Aug. 7, 2011.
International Search Report and Written Opinion for PCT/EP2011/060386 mailed Sep. 16, 2011.
International Search Report and Written Opinion for PCT/US2010/054912 mailed Mar. 16, 2011.
International Search Report for PCT/EP2011/068938 mailed Mar. 27, 2012.
Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.
Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.
Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.
Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.
Worthy, AD. et al., "Regioselective Hydroformylation of Sulfonamides using a Scaffolding Ligand". Organic Letters, 2009, vol. 11, No. 13—p. 2764-2767.
Kametani et al. Chem Pharma Bull, 1965 vol. 13, No. 3, p. 295-299.
Patani et al. Chem Rev, 1996 p. 3147-3176.
Stewart et al. Vitam Horm. 1999;57:249-324.
International Search Report and Written Opinion for PCT/EP2010/057581 mailed Aug. 25, 2010.
De Luis, et al., "Control of Metabolic Syndrome with Metformin in Obese Type 2 Diabetes Mellitus Patients, Diabetes Research and Clinical Practice," 2000, vol. 50, Suppl. 1, pp. S51-S52.
US 8,575,157, 11/2013, Renz et al. (withdrawn).
International Search Report and Written Opinion, International Application No. PCT/US2011/040443, International Filing Date: Jun. 15, 2011, mailed Nov. 11, 2011, 15 pages.

(56) References Cited

OTHER PUBLICATIONS

"Khimiia Elementoorganicheskikh Soedineni", 1982, vol. 1982 pp. 22-26.
"Zhurnal Organicheskoi Khimii", 1982, vol. 18, PT 11, p. 2468.
Anderson, (Chem and Biol 10:787-797, 2003).
Chemical Abstracts, Registry No. 351443-37-3 (Available on Aug. 15, 2001.).
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Chimica Therapeutica, 1968, vol. 3(5), pp. 321-324, 1968.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CASRN: 20057-45-8 abstract, (1969).
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract,(1978).
Database File Registry [Online], Chemical Abstracts Service, Columbus, Ohio, US, 2007, Database accession No. 958599-31-0, Abstract, XP002556900.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958700-63-5, Abstract, XP002556893.
Gavezzotti, "Are Crystal Structures Predictable?", Accounts of Chemical Research, 1994, vol. 27, pp. 309-314.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
International Search Report & Written Opinion—(PCT/US2008/002517) Date of Mailing Dec. 29, 2008.
International Search Report & Written Opinion—(PCT/US2008/009017) Date of Mailing Apr. 12, 2008.
International Search Report and Written Opinion—(PCT/US2008/009048) Date of Mailing Dec. 4, 2008.
International Search Report—(PCT/US2008/012618) Date of Mailing Dec. 3, 2009.
International Search Report—(PCT/US2008/013539) Date of Mailing Mar. 19, 2009.
International Search Report—(PCT/US2009/000057) Date of Mailing Mar. 25, 2009.
International Search Report—(PCT/US2009/000421) Date of Mailing Apr. 15, 2009.
International Search Report—(PCT/US2009/000853) Date of Mailing Sep. 2, 2009.
International Search Report—(PCT/US2009/000908) Date of Mailing Sep. 17, 2009.
International Search Report—(PCT/US2009/001712) Date of Mailing Jul. 14, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2009/002641) Date of Mailing Jul. 3, 2009.
International Search Report—(PCT/US2009/002653) Date of Mailing Jul. 3, 2009.
International Search Report—(PCT/US2009/004261) Date of Mailing Oct. 21, 2009.
International Search Report—(PCT/US2010/023021) Date of Mailing Aug. 5, 2010.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11.beta.-hydroxysteroid Dehydrogenase Type 1 as a Promising Therapeutic Target", Drug Discovery Today, 2007, vol. 12, pp. 504-520.
Morissette et al. Advanced Drug Deliery Reviews 2004, 56, 275-300.
MS Bitar, "Glucocorticoid Dynamics and Impaired Wound Healing in Diabetes Mellitus", Am J Pathol., 1998, vol. 152, pp. 547-554.
MS Bitar, "Insulin and Glucocorticoid-Dependent Suppression of the IGF-I System in Diabetic Wounds", Sugery, 2000, vol. 127, pp. 687-695.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, et al., "Heat-Shock Protein 72/73 and Impaired Wound Healing in Diabetic and Hypercortisolemic States", Sugery, 1999, vol. 125, pp. 594-601.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Souillac et al., Characterization of Delivery Systems, Differential Scanning Calorimetry, pp. 217-218 (in Encyclopedia of Controlled Drug Delivery, 1999, John Wiley & Sons, pp. 212-227).

SUBSTITUTED 5-, 6- AND 7-MEMBERED HETEROCYCLES, MEDICAMENTS CONTAINING SUCH COMPOUNDS, AND THEIR USE

RELATED APPLICATIONS

This application is a divisional of U.S. application Ser. No. 13/703,708, filed May 30, 2013, which is the U.S. National Stage of PCT International Application No. PCT/US2011/040443, filed Jun. 15, 2011, which claims the benefit of U.S. Provisional Application No. 61/355,458, filed Jun. 16, 2010. The entire teachings of the above applications are incorporated herein by reference.

SUMMARY

The present invention relates to compounds derived from the following chemical scaffold which is structurally defined by the formula I

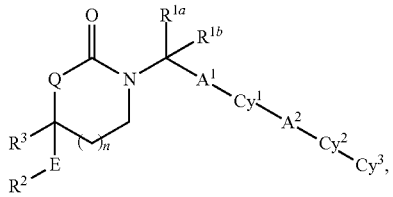

wherein the variables $A^1$, $A^2$, $Cy^1$, $Cy^2$, $Cy^3$, E, n, $R^{1a}$, $R^{1b}$, $R^2$, $R^3$, and Q are as defined hereinafter, including pharmaceutically acceptable salts thereof. The invention further relates to pharmaceutical compositions containing a compound of formula I according to the invention as well as the use of a compound according to the invention for preparing a pharmaceutical composition for the treatment of metabolic disorders. In addition, the invention relates to processes for preparing a pharmaceutical composition as well as a compound according to the invention.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSDtype 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4th Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11β-HSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used as a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043,951).

SUMMARY OF THE INVENTION

The objective of the present invention is to find new substituted 5-, 6- and 7-membered heterocycles, particularly those which are active with regard to the enzyme 11β-hydroxysteroid dehydrogenase (HSD) 1. A further objective of the present invention is to discover substituted 5-, 6- and 7-membered heterocycles which have an inhibitory effect on the enzyme 11β-hydroxysteroid dehydrogenase (HSD) 1 in vitro and/or in vivo and possess suitable pharmacological and pharmacokinetic properties to use them as medicaments.

A further objective of the present invention is to provide new pharmaceutical compositions which are suitable for the prevention and/or treatment of metabolic disorders, particularly diabetes, obesity, and dyslipidemia.

Other objectives of the present invention will become apparent to the skilled man directly from the foregoing and following remarks.

In a first aspect the present invention is a compound which is an HSD inhibitor and is structurally defined by formula I

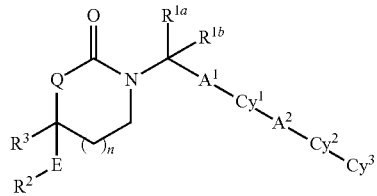

or a pharmaceutically acceptable salt thereof, wherein:
$A^1$ is a bond, $C_{1-2}$-alkylene, $CH_2O$ with the oxygen being attached to $Cy^1$, carbonyl, or C≡C;
$A^2$ is (i) a bond, O, S, or $NR^N$, or (ii) $C_{1-3}$-alkylene or $C_{1-2}$-alkyleneoxy, each of which is optionally substituted with 1 to 4 groups independently selected from methyl, ethyl, and trifluoromethyl, and in each of which one $CH_2$ group is optionally replaced by carbonyl;
$Cy^1$ is aryl, heteroaryl, cycloalkyl, or heterocyclyl, each of which is optionally substituted with 1 to 4 groups independently selected from
halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)$O—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2 NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2 R^6$, —$V^1$—$NHS(=O)_2R^6$, —$V^1$—C(=O)$R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2 N(R^7)_2$, cyano-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

$Cy^2$ is aryl, heteroaryl, cycloalkyl, or heterocyclyl, each of which is optionally substituted with 1 to 4 groups independently selected from
halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)$O—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—C(=O)$R^6$, —$V^1$—$C(=O)O$—$C_{1-6}$-alkyl, —$V^1$—$S(=O)_2R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, carboxy-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$; or heterocyclyl, which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-66}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, —$V^1$—$S(=O)_2R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, carboxy-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$; or aryl or heteroaryl;

E is a bond or $C_{1-3}$-alkylene or $C_{1-2}$-alkylenyloxy, wherein the O is attached to $R^2$, each of which is optionally substituted with 1 to 4 groups independently selected from methyl, ethyl, trifluoromethyl, and oxo;

$R^{1a}$, $R^{1b}$ independently of each other are hydrogen, $C_{1-6}$-alkyl, $C_{3-6}$-cycloalkyl, $C_{2-6}$-alkenyl, $C_{2-6}$-alkynyl or $C_{1-3}$-alkyloxy-$C_{1-3}$-alkyl, or $R^{1a}$ and $R^{1b}$ are joined and, together with the carbon atom they are attached, form a $C_{3-6}$-cycloalkyl group, wherein the above-mentioned $C_{1-6}$-alkyl, $C_{2-6}$-alkenyl, $C_{2-6}$-alkynyl, $C_{1-3}$-alkoxy-$C_{1-3}$-alkyl, and $C_{3-6}$-cycloalkyl groups are optionally substituted with one to three groups independently selected from fluorine, cyano, $C_{1-6}$-alkyl, oxo and hydroxy, $R^2$ is $C_{1-6}$-alkyl, aryl, heteroaryl, cycloalkyl, or heterocyclyl, each of which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

$R^3$ is $C_{1-6}$-alkyl, $C_{2-6}$-alkenyl, $C_{2-6}$-alkynyl, $C_{3-5}$-cycloalkyl-$C_{1-4}$-alkyl, $C_{1-3}$-alkoxy-$C_{1-3}$-alkoxy, or $C_{1-3}$-alkoxy-$C_{1-3}$-alkyl, each of which is optionally substituted with one to four groups independently selected from fluorine, cyano, oxo, —$R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, spirocycloalkyl, heterocyclyl (which in turn is optionally substituted with $C_{1-4}$-alkyl, halo-$C_{1-4}$-alkyl, halogen, or oxo), heteroaryl (which in turn is optionally substituted with $C_{1-4}$-alkyl, halo-$C_{1-4}$-alkyl, $C_{1-4}$-alkoxy, $C_{1-4}$-alkylthio, $C_{1-4}$-alkylsulfonyl, halogen, trifluoromethyl, di($C_{1-3}$-alkyl)amino, nitro, cyano, carboxy, aminocarbonyl, $C_{1-4}$-alkylaminocarbonyl, di($C_{1-3}$-alkyl)aminocarbonyl, or oxo), aryl-amino (which in turn is optionally substituted with $C_{1-4}$-alkyl, $C_{1-4}$-alkoxy, $C_{1-4}$-alkylthio, $C_{1-4}$-alkylsulfonyl, halogen, trifluoromethyl, di($C_{1-4}$-alkyl)amino, nitro, cyano, carboxy, aminocarbonyl, $C_{1-4}$-alkylaminocarbonyl, and di($C_{1-3}$-alkyl)aminocarbonyl) and heteroarylamino (which in turn is optionally substituted with $C_{1-4}$-alkyl, halo-$C_{1-4}$-alkyl, $C_{1-4}$-alkoxy, $C_{1-4}$-alkylthio, $C_{1-4}$-alkylsulfonyl, halogen, trifluoromethyl, di($C_{1-3}$-alkyl)amino, nitro, cyano, carboxy, aminocarbonyl, $C_{1-4}$-alkylaminocarbonyl, di($C_{1-3}$-alkyl)aminocarbonyl, or oxo);

$R^4$ is independently selected from hydrogen, $C_{1-6}$-alkyl and halo-$C_{1-6}$-alkyl;

$R^6$ is independently selected from $C_{1-6}$-alkyl, $C_{2-6}$-alkenyl, and $C_{2-6}$-alkynyl;

$R^7$ is $C_{3-6}$-cycloalkyl;

$R^8$ is heterocyclyl;

$R^9$ is $C_{4-7}$-cycloalkyl-$C_{1-6}$-alkyl, $C_{3-6}$-cycloalkyl-$C_{2-4}$-alkynyl, halo-$C_{1-6}$-alkyl, halo-$C_{2-6}$-alkenyl, halo-$C_{3-6}$-cycloalkyl, halo-$C_{4-7}$-cycloalkyl-$C_{1-6}$-alkyl, $C_{1-6}$-alkoxy-$C_{1-6}$-alkyl, or halo-$C_{1-6}$-alkoxy-$C_{1-6}$-alkyl;

$R^N$ independently of each other is hydrogen, $C_{1-6}$-alkyl, halo-$C_{1-6}$-alkyl, amino-$C_{1-6}$-alkyl, $C_{1-6}$-alkylamino-$C_{1-6}$-alkyl, di($C_{1-6}$-alkyl)amino-$C_{1-6}$-alkyl, hydroxy-$C_{1-6}$-alkyl, and $C_{1-6}$-alkoxy-$C_{1-6}$-alkyl; $C_{3-6}$-cycloalkyl, $C_{3-6}$-alkenyl, $C_{3-6}$-alkynyl, $C_{1-4}$-alkylcarbonyl, $C_{1-4}$-alkylaminocarbonyl, di-($C_{1-3}$-alkyl)aminocarbonyl, $C_{1-4}$-alkyloxycarbonyl, $C_{1-4}$-alkylsulfonyl, n is 0, 1 or 2;

Q is $CH_2$, O, NH, or N($C_{1-6}$-alkyl), wherein alkyl is optionally monosubstituted with halogen or hydroxy;

$V^1$ is independently selected from $C_{1-6}$-alkylene, $C_{2-6}$-alkenylene, $C_{2-6}$-alkynylene, and $C_{1-6}$-alkyleneoxy. An alkyleneoxy is bidirectional. It is to be understood that both directions are included within the meaning of the term, except in cases where the oxygen would be attached to a heteroatom. For example, when $V^1$ is alkyleneoxy in the group —$V^1$—C(O)SONHR$^7$, the oxygen can be attached to either the carbonyl carbon or to the remainder of the molecule. However, when $V^1$ is alkyleneoxy in the group —$V^1$—$NH_2$, the oxygen can be attached only to the remainder of the molecule and not the nitrogen atom.

Another embodiment of the invention is a pharmaceutical composition comprising i) a pharmaceutically acceptable carrier or diluent, and ii) an HSD inhibitor disclosed herein, or a pharmaceutically acceptable salt, enantiomer or diastereomer thereof.

Another embodiment of the invention is a method of inhibiting 11β-HSD1 activity comprising the step of administering to a subject in need of such treatment an effective amount of an HSD inhibitor disclosed herein, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of an HSD inhibitor disclosed herein, or a pharmaceutically acceptable salt, enantiomer or diastereomer thereof.

Another embodiment of the invention is the use of an HSD inhibitor disclosed herein, or a pharmaceutically acceptable salt, enantiomer or diastereomer thereof for the manufacture of a medicament for inhibiting 11β-HSD1 activity in a subject in need of such treatment.

Another embodiment of the invention is the use of an HSD inhibitor disclosed herein, or a pharmaceutically acceptable salt, enantiomer or diastereomer thereof for the manufacture of a medicament for treating a subject with a disease associated with the activity or expression of 11β-HSD1.

Another embodiment of the invention is an HSD inhibitor disclosed herein, or a pharmaceutically acceptable salt, enantiomer or diastereomer thereof for use in inhibiting 11β-HSD1 activity in a subject in need of such treatment.

Another embodiment of the invention is an HSD inhibitor disclosed herein, or a pharmaceutically acceptable salt, enantiomer or diastereomer thereof for use in for treating a subject with a disease associated with the activity or expression of 11β-HSD1.

In a further aspect the present invention is a process for preparing the compounds of general formula I, characterized in that
a compound of general formula IIa, IIb, or IIc

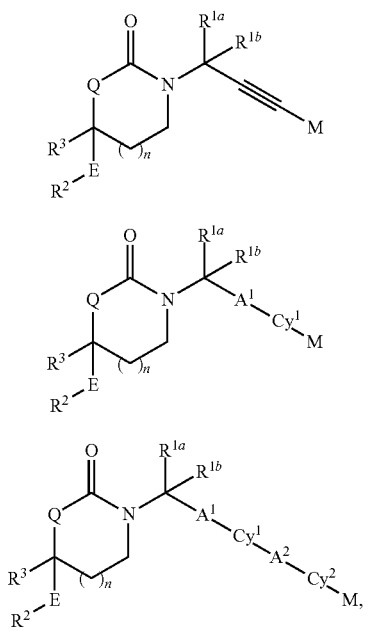

wherein the variables $R^{1a}$, $R^{1b}$, $R^2$, $R^3$, $A^1$, $A^2$, E, Q, $Cy^1$, $Cy^2$, and n are defined as hereinbefore and hereinafter and M is a metal or pseudo-metal containing group and in particular examples denotes
H, MgCl, MgBr, MgI, B(OH)$_2$, B(OC$_{1-3}$-alkyl)$_2$, B(OCMe$_2$CMe$_2$O), BF$_3$K, Si(OC$_{1-4}$-alkyl)$_3$, SiF$_3$, ZnCl, ZnBr, ZnI, Sn(C$_{1-4}$-alkyl)$_3$, wherein all alkyl fragments are optionally mono- or polyfluorinated,
is coupled with a complementary compound of general formula IIIa, IIIb, or IIIc,

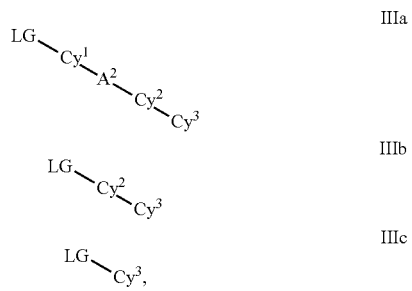

wherein the variables $A^2$, $Cy^1$, $Cy^2$, and $Cy^3$ are defined as hereinbefore and hereinafter and LG is a leaving group and in particular examples denotes
Cl, Br, I, O$_3$SCH$_3$, O$_3$SPh, O$_3$S(CF$_2$)$_o$F, wherein o has a value ranging from 1 to 12 and the phenyl group is optionally substituted with 1 to 5 groups independently selected from fluorine, methyl, methoxy, nitro, cyano, and SO$_2$Me,
in the presence of a transition metal catalyst, preferably derived from Fe, Cu, Ni, or Pd, most preferably Pd, which are employed as elements, e.g. palladium on charcoal or nanoparticles of Pd or Fe, salts, e.g. Pd(O$_2$CCH$_3$)$_2$, Pd(O$_2$CCF$_3$)$_2$, or PdCl$_2$, or complexes, e.g. Pd$_2$(dibenzylideneacetone)$_3$, Pd(PPh$_3$)$_4$, Pd(P$^t$Bu$_3$)$_2$, Pd(PPh$_3$)$_2$Cl$_2$, or Pd[1,1'-bis(diphenyl-phosphino)ferrocene]Cl$_2$, optionally combined with a ligand such as a phosphine, e.g. 2-(optionally substituted phenyl)phenyl-dicyclohexyl-phosphine, 2-(optionally substituted phenyl)phenyl-di-tert-butyl-phosphine, 1,1'-bis(diphenylphosphino)ferrocene, tricyclohexyl-phosphine, trifurylphosphine, tri-tert-butylphosphine, triphenylphosphine, or tritolylphosphine, or a carbene, e.g. derived from a 1,3-diaryl-imidazolidinium salt or 1,3-diaryl-dihydroimidazolidinium salt (aryl is phenyl optionally substituted with one to five groups independently selected from fluorine, C$_{1-3}$-alkyl, C$_{1-3}$-alkyloxy, di-(C$_{1-3}$-alkyl)-amino) and a base, e.g. KOtBu or Cs$_2$CO$_3$, and/or another ligand, e.g. acetonitrile, benzonitrile, or allyl, optionally in the presence of further additives, e.g. LiCl, NaOH, NaO$^t$Bu, KO$^t$Bu, Na$_2$CO$_3$, K$_2$CO$_3$, Cs$_2$CO$_3$, NaO$_2$CCH$_3$, K$_3$PO$_4$, ammonium salts, e.g. Bu$_4$NCl, copper salts, e.g. CuI, and/or silver salts, e.g. AgO$_3$SCF$_3$, preferably employed in benzene, toluene, ether, tetrahydrofuran, 1,4-dioxane, 1,2-dimethoxyethane, N,N-dimethylformamide, N,N-dimethylacetamide, N-methylpyrrolidone, alcohol, e.g. methanol, water, or mixtures thereof, preferably at −10 to 150° C.; though, depending on the coupling partners employed, not all additives and solvents are suited. Certain combinations of the conditions and reagents mentioned in conjunction with the coupling partners are in the literature referred to as Kumada coupling for magnesium substituted compounds II, Suzuki-Miyaura coupling for boron substituted compounds II (see e.g. WO2009/017664, filed Jul. 25, 2008), Hiyama coupling for silicon substituted compounds II, Negishi coupling for zinc substituted compounds II, Stille coupling for tin substituted compounds II, and Sonogashira coupling for compounds IIa. Alternatively, compounds bearing a hydrogen for M may also be suited, particularly when a heteroaromatic Cy is used (see e.g. *ChemSusChem* 2008, 1, 404-407, *Eur. J. Inorg. Chem.* 2008, 2550-59, *J. Am. Chem.*

Soc. 2008, 130, 15185-92, and references quoted therein). The reactivity/polarity pattern of the coupling partners may be reversed as well, i.e. compounds II bear LG instead of M and compounds III M instead of LG, providing the same products under the same or similar reaction conditions. Detailed reaction conditions for the couplings described here can be found in the literature through the respective name of the reaction (see e.g. March's Advanced Organic Chemistry, Michael B. Smith and Jerry March, John Wiley & Sons Inc., 6. Ed., New Jersey, 2007 and references quoted therein) and in the experimental part;

and, if necessary, any protective group used in the reactions described above is cleaved concurrently or subsequently;

if desired, a compound of general formula I thus obtained is resolved into its stereoisomers;

if desired, a compound of general formula I thus obtained is converted into the salts thereof, particularly for pharmaceutical use into the pharmaceutically acceptable salts thereof.

DETAILED DESCRIPTION OF THE INVENTION

The compounds of general formula I according to the invention and pharmaceutically acceptable salts thereof have valuable pharmacological properties, particularly, an inhibitory effect on the enzyme 11β-hydroxysteroid dehydrogenase (HSD) 1.

Unless otherwise stated, the groups, residues, and substituents, particularly $A^1$, $A^2$, $Cy^1$, $Cy^2$, $Cy^3$, E, $R^{1a}$, $R^{1b}$, $R^2$, $R^3$, n, and Q are defined as above and hereinafter. If residues, substituents, or groups occur several times in a compound they may have the same or different meanings. Some preferred meanings of groups and substituents of the compounds according to the invention will be given hereinafter.

Preferred embodiments of the invention are characterized by the following definitions:

a) Definitions ($a^i$) for $A^1$ in the order of preference, ascending from preferably ($a^1$) to more preferably ($a^2$) up to most preferably ($a^3$):
($a^1$): Preferably, $A^1$ denotes bond, $C_{1-2}$-alkylene or ethynyl.
($a^2$): More preferably, $A^1$ denotes bond or ethynyl.
($a^3$): Most preferably, $A^1$ denotes a bond.

b) Definitions ($b^i$) for $A^2$ in the order of preference, ascending from preferably ($b^1$) to more preferably ($b^2$) up to most preferably ($b^3$):
($b^1$): Preferably, $A^2$ denotes bond, O, $CH_2$, $CH_2CH_2$, $CH_2O$, or C(=O).
($b^2$): More preferably, $A^2$ denotes bond, $CH_2CH_2$ or $CH_2O$.
($b^3$): Most preferably, $A^2$ denotes a bond.

c) Definitions ($c^i$) for $Cy^1$ in the order of preference, ascending from preferably ($c^1$) to more preferably ($c^2$) up to most preferably ($c^3$):
($c^1$) Preferably, $Cy^1$ denotes cyclohexyl, piperidinyl, phenyl, thienyl, thiazolyl, thiadiazolyl, pyridyl, pyridazinyl, pyrazinyl, pyrimidinyl, benzimidazolyl, indazolyl, benzothiazolyl or benzotriazolyl, each of which is optionally additionally substituted with 1 or 2 groups independently selected from
halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy.
($c^2$) More preferably, $Cy^1$ denotes cyclohexyl, piperidinyl, phenyl or pyrimidinyl, each of which is optionally additionally substituted with 1 or 2 groups independently selected from
halogen, cyano, $C_{1-6}$-alkyl and $C_{1-6}$-alkoxy.
($c^3$) Most preferably, $Cy^1$ denotes phenyl.

d) Definitions ($d^i$) for $Cy^2$ in the order of preference, ascending from preferably ($d^1$) to more preferably ($d^2$) up to most preferably ($d^3$):
($d^1$): Preferably, $Cy^2$ denotes phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl or 1,1-dioxo-hexahydro-1,2-thiazinyl, each of which is optionally additionally substituted with 1 or 2 groups independently selected from
halogen, cyano, hydroxy, $C_{1-6}$-alkyl, halo-$C_{1-14}$-alkyl, $C_{2-6}$-alkenyl, $C_{2-6}$-alkynyl, $C_{1-6}$-alkoxy and halo-$C_{1-4}$-alkoxy.
($d^2$): More preferably, $Cy^2$ denotes phenyl, pyrazolyl, thiazolyl, pyridinyl, pyridazinyl, 2-oxo-1,2-dihydropyridinyl or pyrimidinyl, each of which is optionally additionally substituted with 1 or 2 groups independently selected from
halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy.
($d^3$): Most preferably, $Cy^2$ denotes phenyl, pyrazolyl, thiazolyl, pyridinyl, pyridazinyl, 2-oxo-1,2-dihydropyridinyl, or pyrimidinyl.

e) Definitions ($e^i$) for $Cy^3$ in the order of preference, ascending from preferably ($e^1$) to more preferably ($e^2$) to even more preferably ($e^3$) up to most preferably ($e^4$):
($e^1$) Preferably, $Cy^3$ denotes $C_{3-6}$-cycloalkyl, which is mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxycarbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-14}$-alkylsulfonyl-$C_{1-14}$-alkyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl, or 2-oxo-1,2-dihydropyridinyl, which is optionally mono- or disubstituted independently of each other with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di- $C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl.

($e^2$) More preferably, $Cy^3$ denotes $C_{3-6}$-cycloalkyl, which is mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or 2-oxo-1,2-dihydropyridinyl, which is optionally mono- or disubstituted independently of each other with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl.

($e^3$) Even more preferably, $Cy^3$ denotes $C_{3-6}$-cycloalkyl, which is monosubstituted with cyano, aminocarbonyl, methylaminocarbonyl, dimethylaminocarbonyl, carboxy, ethoxycarbonyl or methylsulfonyl, or azetidinyl, oxetanyl, pyrrolidinyl, 2-oxo-pyrrolidinyl, tetrahydrofuranyl, piperidinyl, 2-oxo-piperidinyl, tetrahydropyranyl, 2-oxo-imidazolidinyl, or morpholinyl, each of which is optionally mono- or disubstituted with a group independently selected from fluorine, methyl, aminocarbonyl and hydroxy, or 1,2-dihydropyridin-2-on-yl, which is optionally monosubstituted with a group selected from fluorine and methyl.

($e^4$) Most preferably, $Cy^3$ denotes 1-cyano-cyclopropyl, 1-ethoxycarbonyl-cyclopropyl, 1-carboxy-cyclopropyl, 1-aminocarbonyl-cyclopropyl, 1-methylaminocarbonyl-cyclopropyl, 1-dimethylaminocarbonyl-cyclopropyl, 1-methylsulfonyl-cyclopropyl, 1-aminocarbonyl-cyclobutyl, 1-aminocarbonyl-cyclopentyl, 1-aminocarbonyl-cyclohexyl, 4-aminocarbonyl-tetrahydropyran-4-yl, azetidin-1-yl, azetidin-3-yl, 3-hydroxy-azetidin-1-yl, 3-fluoro-azetidin-1-yl, 3,3-difluoro-azetidinyl, oxetan-3-yl, 3-hydroxy-oxetan-3-yl, 2-aminocarbonyl-pyrrolidin-1-yl, tetrahydrofuran-3-yl, tetrahydropyran-4-yl, pyrrolidin-2-on-1-yl, 1-methyl-pyrrolidin-2-on-3-yl, 1,3-dimethyl-pyrrolidin-2-on-3-yl, 3-hydroxy-1-methyl-pyrrolidin-2-on-3-yl, 2-oxo-imidazolidin-1-yl, 3-methyl-2-oxo-imidazolidin-1-yl, morpholin-4-yl, piperidin-2-on-1-yl, or 1,2-dihydropyridin-2-on-1-yl.

f) Definitions ($f^i$) for E in the order of preference, ascending from preferably ($f^1$) to more preferably ($f^2$) up to most preferably ($f^3$):

($f^1$) Preferably, E denotes bond or $C_{1-3}$-alkylene or $C_{1-2}$-alkylenyloxy, wherein the O is attached to $R^2$, each of which is optionally substituted with 1 or 2 methyl groups.

($f^2$) More preferably, E denotes bond or $C_{1-3}$-alkylene.

($f^3$) Most preferably, E denotes bond.

g) Definitions ($g^i$) for $R^{1a}$ and $R^{1b}$ in the order of preference, ascending from preferably ($g^1$) to more preferably ($g^2$) up to most preferably ($g^3$):

($g^1$) Preferably, $R^{1a}$ and $R^{1b}$ denote independently of each other hydrogen, $C_{1-4}$-alkyl, cyclopropyl or methoxymethyl ($g^2$) More preferably, $R^{1a}$ denotes methyl, ethyl or cyclopropyl and $R^{1b}$ denotes hydrogen.

($g^3$) Most preferably, $R^{1a}$ denotes methyl and $R^{1b}$ denotes hydrogen.

h) Definitions ($h^i$) for $R^2$ in the order of preference, ascending from preferably ($h^1$) to more preferably ($h^2$) up to most preferably ($h^3$):

($h^1$) Preferably, $R^2$ denotes phenyl, fluorophenyl, $C_{1-4}$-alkyl, trifluoroethyl, cyclopropyl or cyclopropylmethyl.

($h^2$) More preferably, $R^2$ is phenyl, fluorophenyl or cyclopropylmethyl.

($h^3$) Most preferably, $R^2$ is phenyl.

j) Definitions ($j^i$) for $R^3$ in the order of preference, ascending from preferably ($j^1$) to more preferably ($j^2$) up to most preferably ($j^3$):

($j^1$): Preferably, $R^3$ denotes methyl, ethyl, propyl, butyl, vinyl, allyl or ethoxyethyl, each of which is optionally substituted with one or two groups independently selected from methyl, cyano, aminocarbonyl, methylaminocarbonyl, dimethylaminocarbonyl, hydroxymethylcarbonylamino, 2-oxo-pyrrolidin-1-yl, carboxy, amino, methylamino, dimethylamino, acetylamino, aminocarbonylamino, methylaminocarbonylamino, ethylaminocarbonylamino, N-methyl-N-methylcarbonyl-amino, methylsulfonylamino, N-methyl-N-methylsulfonyl-amino, hydroxy, methoxy, 2-hydroxyethoxy, aminocarbonyloxy, methylsulfanyl, methylsulfinyl and methylsulfonyl.

($j^2$): More preferably, $R^3$ is 2-methylallyl, 2-aminocarbonyl-ethyl, 2-aminocarbonyl-2-methyl-propyl, 3-methylsulfonylamino-propyl, 2-hydroxyethyl, 2-hydroxy-2-methylpropyl, 3-hydroxypropyl, 3-hydroxy-3-methylbutyl or 2-cyano-2-methylpropyl.

($j^3$): Most preferably, $R^3$ is 2-hydroxy-2-methyl-propyl.

k) Definitions ($k^i$) for n in the order of preference, ascending from preferably ($k^1$) to most preferably ($k^2$):

($k^1$) Preferably, n is 1 or 2.

($k^2$) Most preferably, n is 1.

l) Definitions ($l^i$) for Q in the order of preference, ascending from preferably ($l^1$) to more preferably ($l^2$) up to most preferably ($l^3$):

($l^1$) Preferably, Q is O, $CH_2$ or NH.

($l^2$) More preferably, Q is NH or O.

($l^3$) Most preferably, Q is O.

Each $a^i$, $b^i$, $c^i$, $d^i$, $e^i$, $f^i$, $g^i$, $h^i$, $j^i$, $k^i$ and $l^i$ represents a characterized, individual embodiment for the corresponding substituent as described above. Thus given the above definitions, preferred individual embodiments of the first aspect of the invention are fully characterized by the term ($a^i b^i c^i d^i e^i f^i g^i h^i j^i k^i l^i$), wherein for each index i an individual figure is given that ranges from 1 to the highest number given above; index 0 for each letter refers to the individual embodiment recited in the section entitled "Summary of the Invention". Indices i vary independently from each other. All individual embodiments described by the term in parentheses with full permutation of the indices i, including i equals 0, referring to the definitions above, shall be comprised by the present invention.

The following Table 1 shows exemplarily embodiments E-1 to E-28 of the invention that are considered preferred.

TABLE 1

| Exemplary embodiments E-1 to E-28 of the invention | | | | | | | | | | | |
|---|---|---|---|---|---|---|---|---|---|---|---|
| | $A^1$ | $A^2$ | $Cy^1$ | $Cy^2$ | $Cy^3$ | E | $R^{1a}/R^{1b}$ | $R^2$ | $R^3$ | n | Q |
| E-1 | $a^1$ | $b^1$ | $c^1$ | $D^1$ | $e^1$ | $f^1$ | $g^1$ | $h^1$ | $j^1$ | $k^1$ | $l^1$ |
| E-2 | $a^2$ | $b^2$ | $c^1$ | $D^1$ | $e^1$ | $f^2$ | $g^2$ | $h^2$ | $j^2$ | $k^2$ | $l^2$ |

TABLE 1-continued

Exemplary embodiments E-1 to E-28 of the invention

| | $A^1$ | $A^2$ | $Cy^1$ | $Cy^2$ | $Cy^3$ | E | $R^{1a}/R^{1b}$ | $R^2$ | $R^3$ | n | Q |
|---|---|---|---|---|---|---|---|---|---|---|---|
| E-3 | $a^3$ | $b^3$ | $c^1$ | $D^1$ | $e^1$ | $f^3$ | $g^2$ | $h^2$ | $j^2$ | $k^2$ | $l^2$ |
| E-4 | $a^3$ | $b^3$ | $c^2$ | $D^1$ | $e^{13}$ | $f^3$ | $g^2$ | $h^2$ | $j^2$ | $k^2$ | $l^2$ |
| E-5 | $a^3$ | $b^3$ | $c^3$ | $D^1$ | $e^1$ | $f^3$ | $g^2$ | $h^2$ | $j^2$ | $k^2$ | $l^2$ |
| E-6 | $a^3$ | $b^3$ | $c^3$ | $D^2$ | $e^1$ | $f^3$ | $g^2$ | $h^2$ | $j^2$ | $k^2$ | $l^2$ |
| E-7 | $a^3$ | $b^3$ | $c^3$ | $D^2$ | $e^2$ | $f^3$ | $g^2$ | $h^2$ | $j^2$ | $k^2$ | $l^2$ |
| E-8 | $a^3$ | $b^3$ | $c^3$ | $D^2$ | $e^2$ | $f^3$ | $g^2$ | $h^2$ | $j^3$ | $k^2$ | $l^2$ |
| E-9 | $a^3$ | $b^3$ | $c^3$ | $d^2$ | $e^2$ | $f^3$ | $g^3$ | $h^2$ | $j^3$ | $k^2$ | $l^2$ |
| E-10 | $a^3$ | $b^3$ | $c^3$ | $d^2$ | $e^2$ | $f^3$ | $g^2$ | $h^3$ | $j^3$ | $k^2$ | $l^2$ |
| E-11 | $a^3$ | $b^3$ | $c^3$ | $d^2$ | $e^2$ | $f^3$ | $g^2$ | $h^2$ | $j^3$ | $k^2$ | $l^3$ |
| E-12 | $a^3$ | $b^3$ | $c^3$ | $d^2$ | $e^3$ | $f^3$ | $g^2$ | $h^2$ | $j^3$ | $k^2$ | $l^2$ |
| E-13 | $a^3$ | $b^3$ | $c^3$ | $d^2$ | $e^3$ | $f^3$ | $g^2$ | $h^3$ | $j^3$ | $k^2$ | $l^2$ |
| E-14 | $a^3$ | $b^3$ | $c^3$ | $d^3$ | $e^3$ | $f^3$ | $g^2$ | $h^3$ | $j^3$ | $k^2$ | $l^2$ |
| E-15 | $a^3$ | $b^3$ | $c^3$ | $d^3$ | $e^3$ | $f^3$ | $g^3$ | $h^3$ | $j^3$ | $k^2$ | $l^2$ |
| E-16 | $a^3$ | $b^3$ | $c^3$ | $d^3$ | $e^4$ | $f^3$ | $g^3$ | $h^3$ | $j^3$ | $k^2$ | $l^2$ |
| E-17 | $a^3$ | $b^3$ | $c^3$ | $d^3$ | $e^3$ | $f^3$ | $g^3$ | $h^3$ | $j^3$ | $k^2$ | $l^3$ |
| E-18 | $a^3$ | $b^3$ | $c^3$ | $d^3$ | $e^4$ | $f^3$ | $g^3$ | $h^3$ | $j^3$ | $k^2$ | $l^3$ |
| E-19 | $a^3$ | $b^3$ | $c^0$ | $d^0$ | $e^0$ | $f^0$ | $g^0$ | $h^0$ | $j^0$ | $k^0$ | $l^0$ |
| E-20 | $a^3$ | $b^3$ | $c^0$ | $d^0$ | $e^0$ | $f^3$ | $g^0$ | $h^0$ | $j^0$ | $k^2$ | $l^2$ |
| E-21 | $a^3$ | $b^3$ | $c^0$ | $d^0$ | $e^1$ | $f^3$ | $g^0$ | $h^0$ | $j^0$ | $k^2$ | $l^2$ |
| E-22 | $a^3$ | $b^3$ | $c^1$ | $d^1$ | $e^2$ | $f^3$ | $g^1$ | $h^1$ | $j^1$ | $k^2$ | $l^2$ |
| E-23 | $a^3$ | $b^3$ | $c^2$ | $d^2$ | $e^3$ | $f^3$ | $g^2$ | $h^2$ | $j^2$ | $k^2$ | $l^2$ |
| E-24 | $a^3$ | $b^3$ | $c^3$ | $d^3$ | $e^4$ | $f^3$ | $g^3$ | $h^3$ | $j^3$ | $k^2$ | $l^2$ |
| E-25 | $a^3$ | $b^3$ | $c^3$ | $d^2$ | $e^3$ | $f^3$ | $g^2$ | $h^2$ | $j^3$ | $k^2$ | $l^2$ |
| E-26 | $a^3$ | $b^3$ | $c^3$ | $d^1$ | $e^2$ | $f^3$ | $g^1$ | $h^2$ | $j^3$ | $k^2$ | $l^2$ |
| E-27 | $a^3$ | $b^3$ | $c^1$ | $d^1$ | $e^2$ | $f^3$ | $g^1$ | $h^2$ | $j^3$ | $k^2$ | $l^2$ |
| E-28 | $a^3$ | $b^3$ | $c^1$ | $d^1$ | $e^2$ | $f^3$ | $g^1$ | $h^2$ | $J^1$ | $k^2$ | $l^2$ | including pharmaceutically acceptable salts thereof.

Another preferred embodiment of this invention is described by formula I.a

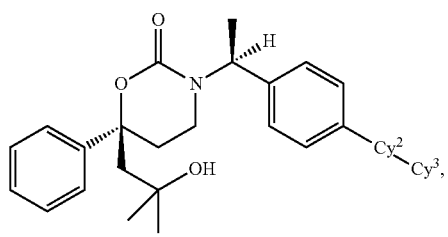

I.a or a pharmaceutically acceptable salt thereof, wherein the variables $Cy^2$ and $Cy^3$ are defined as hereinbefore and hereinafter, their tautomers, their stereoisomers, mixtures thereof, and the salts thereof. Alternatively, $Cy^2$ and $Cy^3$ are defined as follows: $d^1$ and $e^1$; $d^1$ and $e^2$; $d^1$ and $e^3$; $d^1$ and $e^{14}$; $d^2$ and $e^1$; $d^2$ and $e^2$; $d^2$ and $e^3$; $d^2$ and $e^4$; $d^3$ and $e^1$; $d^3$ and $e^2$; and $d^3$ and $e^4$.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

The term "substituted" as used herein means that any one or more hydrogens on the designated atom is replaced with a selection from the indicated group, provided that the designated atom's normal valence is not exceeded, and that the substitution results in a stable compound.

The term "partially unsaturated" as used herein means that in the designated group or moiety 1, 2, or more, preferably 1 or 2, double bonds are present. "Partially unsaturated" does not cover fully unsaturated groups or moieties such as aromatic and heteroaromatic groups.

The term halogen denotes an atom selected from the group consisting of F, Cl, Br, and I.

The term $C_{1-n}$-alkyl, wherein n may have a value of 1 to 18, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl, etc.

The term halo-$C_{1-n}$-alkyl, wherein n may have a value of 1 to 18, denotes a $C_{1-n}$-alkyl group defined as described above wherein 1 to 2n+1 hydrogen atoms may be replaced by halogen, preferably fluorine. Examples of such groups include fluoromethyl, difluoromethyl, trifluoromethyl, 2,2,2-trifluoroethyl, pentafluoroethyl, heptafluoropropyl, chlorodifluoromethyl, etc.

The term $C_{2-n}$-alkenyl, wherein n has a value of 3 to 10, denotes a branched or unbranched hydrocarbon group with 2 to n C atoms and a C=C double bond. Examples of such groups include ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, etc.

The term $C_{2-n}$-alkynyl, wherein n has a value of 3 to 10, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Unless otherwise stated alkynyl groups are connected to the remainder of the molecule via the C atom in position 1. Therefore terms such as 1-propynyl, 2-propynyl, 1-butynyl, etc. are equivalent to the terms 1-propyn-1-yl, 2-propyn-1-yl, 1-butyn-1-yl, etc. This also applies analogously to $C_{2-n}$-alkenyl groups.

The term $C_{1-n}$-alkoxy denotes a $C_{1-n}$-alkyl-O group, wherein $C_{1-n}$-alkyl is as hereinbefore defined. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy, etc.

The term $C_{1-n}$-alkylcarbonyl denotes a $C_{1-n}$-alkyl-C(=O) group, wherein $C_{1-n}$-alkyl is as hereinbefore defined. Examples of such groups include methylcarbonyl, ethylcarbonyl, n-propylcarbonyl, iso-propylcarbonyl, n-butylcarbonyl, iso-butylcarbonyl, sec-butylcarbonyl, tert-butylcarbonyl, n-pentylcarbonyl, iso-pentylcarbonyl, neo-pentylcarbonyl, tert-pentylcarbonyl, n-hexylcarbonyl, iso-hexylcarbonyl, etc.

The term "aryl" means an carbocyclic aromatic radical with six to fourteen carbon atoms. Examples include phenyl, a naphthyl, indanyl or a tetrahydronaphthalene. A substituted aryl group has from 1-4 substituents. Unless otherwise indicated, substituents are selected independently of each other from $R^5$. The term "aryl" may be used interchangeably with the terms "aryl ring" "carbocyclic aromatic ring", "aryl group" and "carbocyclic aromatic group";

The term "heteroaryl" means a 5-12-membered heteroaromatic radical containing 0-4 heteroatoms selected from N, O, and S. A heteroaryl can be monocyclic or bicyclic, for example, fused to an aryl, monocyclic heteroaryl, heterocyclyl or cycloalkyl group. Examples include 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A substituted heteroaryl has from 1-4 substituents. Unless otherwise indicated, substituents are selected independently of each other from $R^5$. Ring nitrogen atoms are optionally substituted by oxo to form an N-oxide. The terms "heteroaryl", "heteroaromatic", "heteroaryl ring", "heteroaryl group", "heteroaromatic ring", and "heteroaromatic group" are used interchangeably.

Tautomeric forms exist when a compound is a mixture of two or more structurally distinct compounds that are in rapid equilibrium. N-containing heteroaromatic groups, such as heteroaryl possessing one or more nitrogens within its framework, that bear a hydroxy group at the carbon atom adjacent to the nitrogen or another position of the ring which allows a mesomeric interaction with the nitrogen, can have tautomeric forms. Examples of such substructures of heteroaromatic groups wherein a tautomeric amide may be formed are depicted in the following compilation, wherein $R^N$ is hydrogen:

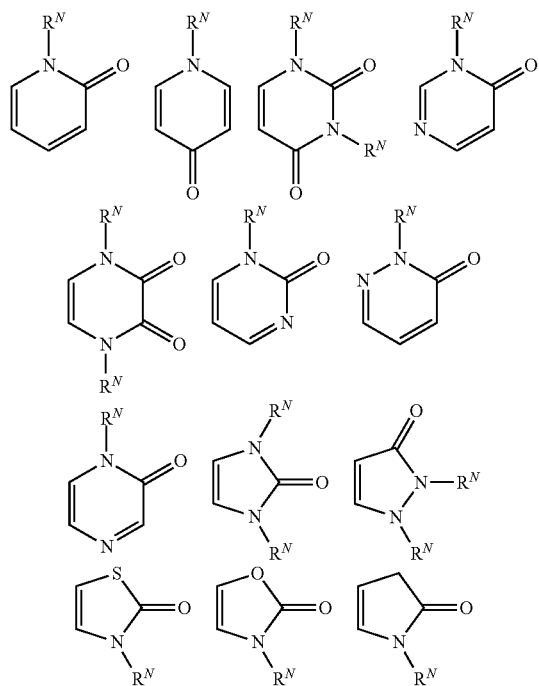

These tautomeric structures may be annelated to heteroaromatic and aromatic groups. It is to be understood that when one tautomeric form of a compound or group is depicted by name or structure, all tautomeric forms of the compound or group are included.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A substituted heterocyclyl has from 1-4 substituents. Unless otherwise indicated, substituents are selected independently of each other from $R^5$;

$R^5$ denotes halogen, $C_{1-3}$-alkyl, $C_{3-6}$-cycloalkyl, cyano, carboxy, $C_{1-4}$-alkyloxycarbonyl, aminocarbonyl, $C_{1-3}$-alkylaminocarbonyl, di-($C_{1-3}$-alkyl)aminocarbonyl, difluoromethyl, trifluoromethyl, amino, $C_{1-3}$-alkylamino, di-($C_{1-3}$-alkyl)amino, $C_{1-3}$-alkylcarbonylamino, $C_{1-3}$-alkylsulfonylamino, nitro, hydroxy, oxo, $C_{1-3}$-alkyloxy, difluoromethoxy, trifluoromethoxy, methylsulfanyl, methylsulfinyl, methylsulfonyl, aminosulfonyl, or phenyl optionally substituted with 1 or 2 substituents independently of each other selected from fluorine, methyl, cyano, methoxy, and hydroxy;

whilst the above-mentioned alkyl or alkylene moieties may be branched or unbranched.

The term $C_{3-n}$-cycloalkyl denotes a saturated mono-, bi- or tri-cyclic fused, bridged or spirocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc. Preferably the term $C_{3-7}$-cycloalkyl denotes saturated monocyclic groups.

The term $C_{5-n}$-cycloalkenyl denotes a $C_{5-n}$-cycloalkyl group which is as hereinbefore defined and additionally has at least one unsaturated C=C double bond.

The term $C_{3-n}$-cycloalkylcarbonyl denotes a $C_{3-n}$-cycloalkyl-C(=O) group wherein $C_{3-n}$-cycloalkyl is as hereinbefore defined.

The term tri-($C_{1-n}$-alkyl)silyl comprises silyl groups which have identical or two or three different alkyl groups which have 1 to n C atoms.

The term di-($C_{1-n}$-alkyl)amino comprises amino groups which have identical or two different alkyl groups which have 1 to n C atoms.

If groups or residues are optionally substituted, this applies to any form of the group or residue. For instance, if an alkyl group is optionally mono- or polyfluorinated this also includes alkyl residues which are part of larger groups, e.g. alkenyl, alkynyl, alkyloxy, alkylcarbonyl, alkoxyalkyl, etc., or if an aryl or heteroaryl group is optionally mono- or polysubstituted with a certain substituent or a set of substituents this also includes aryl or heteroaryl groups which are part of larger groups, e.g. aryl- or heteroaryl-$C_{1-n}$-alkyl, aryl- or heteroaryloxy, aryl- or heteroaryloxy-$C_{1-n}$-alkyl, aryl- or heteroaryl-$C_{1-n}$-alkyloxy, etc. Accordingly, in cases where a residue has e.g. the meaning aryloxy, while aryl residues are optionally mono- or polyfluorinated and aryl denotes inter alia phenyl, the meanings mono-, di-, tri-, tetra-, and pentafluorophenoxy are also included. The same applies to groups or residues in which a part of the group or residue is replaced as e.g. a $CH_2$ group is optionally replaced with O, S, $NR^N$, CO, or $SO_2$. For instance, a residue having inter alia the meaning HO—$C_{1-3}$-alkyl in which a $CH_2$ group is optionally replaced by CO (=carbonyl), this also comprises $HO_2C$—, $HO_2C$—$CH_2$, HO—$CH_2$—C(=O)—, H(O=)C—CH(OH)—, $HO_2CCH_2CH_2$, $HO_2CCH(CH_3)$—, $HOCH_2$—C(=O)—$CH_2$, H(O=)C—C(OH)($CH_3$)—, H(O=)C—CH($CH_2OH$)—, $HOCH_2$—$CH_2$—C(=O)—, $H_3C$—$H_2C$(OH)—C(=O)—, H(O=)C—CH(OH)—$CH_2$, H(O=)C—$CH_2$—CH(OH)—, and $H_3C$—C(=O)—CH(OH)—.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

All atoms/elements described herein, including atoms that are part of a group, comprise all stable isotopic forms of the respective element. For instance, whenever hydrogen is mentioned, either explicitly or as part of a group such as methyl, this includes hydrogen and deuterium as stable isotopic forms of the element hydrogen.

As used herein, the term "subject" and "patient" may be used interchangeably, and means a human in need of treatment.

The compounds according to the invention may be obtained using methods of synthesis known in principle. Preferably, the compounds are obtained by the following methods according to the invention which are described in more detail hereinafter.

Compounds of Formula I can be prepared by several processes. In the discussion below, $A^1$, $A^2$, $Cy^1$, $Cy^2$, $Cy^3$, E, $R^{1a}$, $R^{1b}$, $R^2$, $R^3$, $R^N$, n, and Q have the meanings specified above unless otherwise noted.

A general route to access compounds of the invention, wherein Q preferably denotes O or $NR^N$, is delineated in Scheme 1. Starting from appropriately derivatized carboxylic acid 1 and amine 2 carboxylic amide 3 is prepared using standard amide coupling conditions. For instance, N-(3-dimethylaminopropyl)-N'-ethylcarbodiimide or 2-(1H-benzotriazol-1-yl)-1,1,3,3-tetramethyl-uronium tetrafluoroborate, optionally in the presence of 1-hydroxy-benzotriazole or 2,4,6-tripropyl-1,3,5,2,4,6-trioxatriphosphorinane-2,4,6-trioxide, combined with a base, e.g. N,N-diisopropyl-ethylamine or triethylamine, in an inert solvent, such as N,N-dimethylformamide, N-methylpyrrolidinone, or $CH_2Cl_2$, at 0 to 80° C. are routine conditions to achieve this transformation. Reduction of amide 3 to obtain amine 4 is preferably conducted with hydride transferring reagents, such as borane in complex with e.g. tetrahydrofuran or dimethyl sulfide, $iBu_2AlH$, or $LiAlH_4$, in an inert solvent, such as tetrahydrofuran, ether, or 1,2-dimethoxyethane, at 0 to 100° C. Treatment of amine 4 with an activated carbonic acid derivative, e.g. phosgene, diphosgene, triphosgene, carbonyl diimidazole, p-nitrophenyl chloroformate, $ClCO_2C_{1-4}$-alkyl, $ClCO_2CH_2Ph$, or $(C_{1-4}$-alkylOCO$)_2CO$, in an inert solvent, such as tetrahydrofuran, $CH_2Cl_2$, 1,4-dioxane, toluene, or acetonitrile, preferably in the presence of a base, such as triethylamine, pyridine, or $NaHCO_3$, optionally in the presence of an additive such as 4-dimethylaminopyridine, at −10 to 120° C. provides, depending on the carbonic acid derivative used, intermediate 6, which is primarily produced when $ClCO_2C_{1-4}$-alkyl or $(C_{1-4}$-alkylOCO$)_2CO$ is employed, or directly target compound I'. Intermediate 6 is cyclized by deprotonating Q with a base, e.g. NaH, KH, sodium amide, or butyl lithium, in an inert solvent, e.g. toluene, ether, tetrahydrofuran, 1,4-dioxane, N,N-dimethylformamide, or N-methylpyrrolidinone, at −80 to 100° C.

Scheme 1. Strategy 1 to construct compounds of the invention

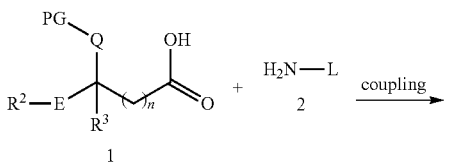

1

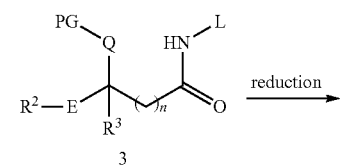

3

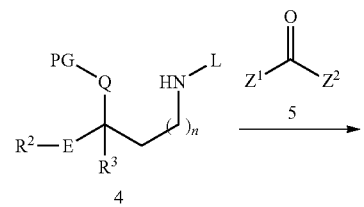

4

-continued

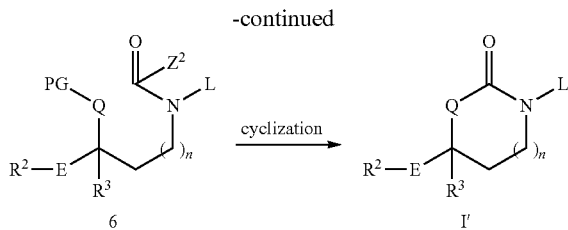

PG = protective group or H

L = 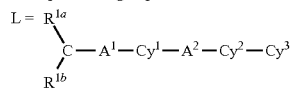 or a truncated form of it that allows attachment of missing residues $R^{1a}$, $R^{1b}$, $A^1$, $Cy^1$, $A^2$, $Cy^2$, and/or $Cy^3$ $Z^1$, $Z^2$ = e.g. Cl, OCCl$_3$, 1-imidazole, 4-nitrophenoxy, succinyloxy, OBn, OC$_{1-4}$-alkyl Scheme 2 outlines another strategy to access compounds of the invention, wherein Q denotes O or NR$^N$. Starting with amine 2 and α,β-unsaturated ketone 7a or ketone 7b, which bears a leaving group (LG) such as chlorine, bromine, iodine, methylsulfonyloxy, 4-tolylsulfonyloxy, or trifluoromethylsulfonyloxy, amine 8 is obtained by 1,4-addition or nucleophilic substitution. Ketones of formula 7b, wherein Q is O, can in turn be prepared from α,β-unsaturated ketones of formula 7a by the formal addition of the corresponding H-LG, such as HCl, HBr, and HI, or, also applicable to compounds wherein Q is NR$^N$, from the corresponding hydroxy compound by sulfonylation with sulfonyl chlorides or anhydrides, e.g. mesyl chloride, tosyl chloride, or trifluoromethanesulfonic anhydride, in the presence of a base, e.g. pyridine or triethylamine, in e.g. dichloromethane, toluene, tetrahydrofuran, 1,4-dioxane, or 1,2-dimethoxyethane at −20 to 60° C. Compound 9 can be prepared by reaction of amine 8 with C$_{1-4}$-alkyloxycarbonyl or benzyloxycarbonyl chloride or anhydride, optionally in the presence of a base, such as triethylamine, ethyl-diisopropyl-amine, or NaHCO$_3$, in an inert solvent, such as toluene, dichloromethane, tetrahydrofuran, or acetonitrile. Addition of an organometal compound R$^3$-M, wherein M preferably denotes ZnCl, ZnBr, ZnI, MgCl, MgBr, MgI, and Li, to ketones of formula 9, optionally in the presence of CeCl$_3$ or a Lewis acid, e.g. boron trifluoride etherate or trimethylsilyl chloride, furnishes, after cyclization of the adduct, compounds of formula I'. In specific examples R$^3$-M is allylmagnesium bromide, allylzinc bromide, (2-methylallyl)magnesium chloride, or (2-methoxy-2-oxoethyl) zinc bromide and added to ketone 9 in an inert solvent, preferably toluene, ether, tetrahydrofuran, 1,4-dioxane, 1,2-dimethoxyethane, or N-methylpyrrolidinone, at −78 to 60° C. The roles of R$^3$ and R$^2$-E as given in Scheme 2 can be reversed, i.e. R$^3$ is part of compound 7a and 7b and R$^2$-E is introduced via organometal compound 10. Depending on the ease of accessibility of intermediates 7a/7b and 10, the former or latter proceeding may be favored (in the following potential syntheses of intermediate 7b only are delineated that, however, may be as well employed for the synthesis of the corresponding intermediate 7b incorporating R$^3$ instead of R$^2$-E).

Scheme 2. Strategy 2 to construct compounds of the invention

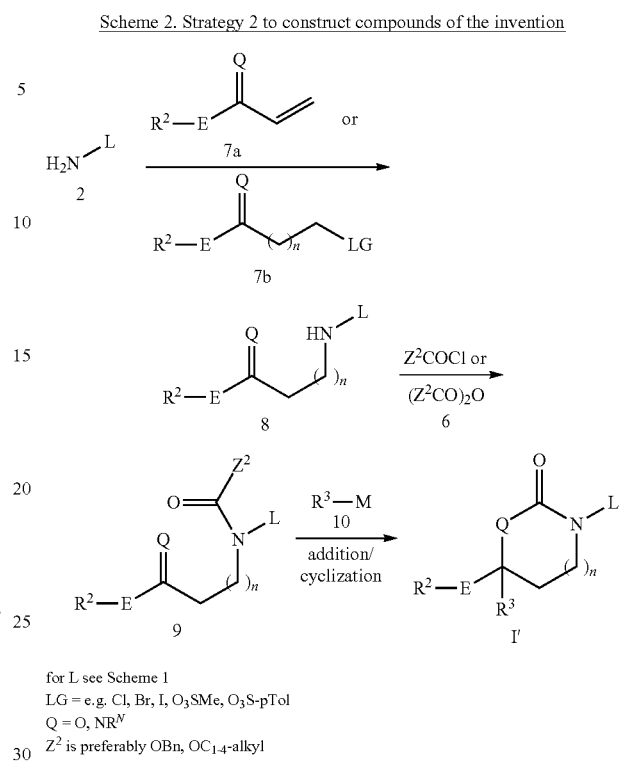

for L see Scheme 1
LG = e.g. Cl, Br, I, O$_3$SMe, O$_3$S-pTol
Q = O, NR$^N$
$Z^2$ is preferably OBn, OC$_{1-4}$-alkyl A further way of synthesis of a compound of formula I, wherein Q equals O or NR$^N$, is described in Scheme 3. Reaction of compound 12, bearing a leaving group (LG) such as chlorine, bromine, iodine, methylsulfonyloxy, 4-tolylsulfonyloxy, or trifluoromethylsulfonyloxy, with isocyanate 11, optionally in the presence of a base, e.g. triethylamine, K$_2$CO$_3$, KOtBu, or NaH, in an inert solvent, such as toluene, tetrahydrofuran, 1,4-dioxane, acetonitrile, N,N-dimethylformamide, or N,N-methylpyrrolidinone, preferably at −10 to 120° C., affords target compound I' after intramolecular nucleophilic substitution of LG in the adduct. Isocyanates of formula 11 can be prepared from amines of formula 2 by treatment with e.g. phosgene, diphosgene, or triphosgene, in the presence of a base, e.g. NEt$_3$, K$_2$CO$_3$, or NaHCO$_3$.

Scheme 3. Strategy 3 to construct comounds of the invention

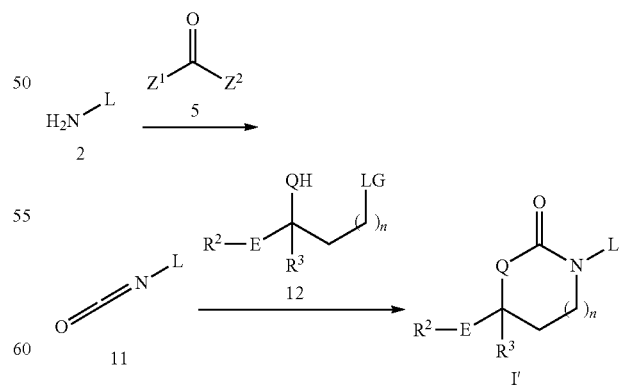

$Z^1$, $Z^2$ is preferably Cl, OCCl$_3$, 1-imidazole, 4-nitrophenoxy
for L see Scheme 1
Q is O or NR$^N$
LG = e.g. Cl, Br, I, O$_3$SCH$_3$, O$_3$S-pTol, O$_3$SCF$_3$ Amines of formula 2 can be prepared by Ritter reaction of alcohols of formula 12 with HCN or trimethylsilyl cyanide, by addition of two nucleophiles of formula 15a and 15b, which are added at once in case $R^{1a}$ equals $R^{1b}$ or successively in case they are different, to nitriles of formula 13, or by Hofmann or Curtius rearrangement starting from carboxylic acids of formula 14. The Ritter reaction is preferably conducted in the presence of a strong Lewis acid, such as sulfuric acid, trifluoromethanesulfonic acid, or boron trifluoride, in e.g. acetic acid, dichloromethane, 1,2-dichloroethane, or without an additional solvent, at −20 to 80° C.

Depending on the reaction conditions and the nitrile, amine 2 is obtained directly thereafter or an intermediate, the corresponding formamide, is generated, which can be hydrolyzed using an acid, e.g. sulfuric acid, or a base, e.g. NaOH or KOH, to afford 2. Addition of a carbon nucleophile to nitrile 13 or the derived imine, which is obtained after the addition of only one of $R^{1a}$ and $R^{1b}$, is preferably carried out with the corresponding Li or MgCl/Br derivatized $R^{1a}$ or $R^{1b}$, while hydride addition is preferably conducted using LiAlH$_4$ or HAl(i-Bu)$_2$. The nucleophiles are preferably added at −70 to 60° C. in inert solvents, such as toluene, dichloromethane, ether, tetrahydrofuran, 1,4-dioxane, or 1,2-dimethoxyethane. A convenient way of accomplishing the Curtius rearrangement of acid 14 uses diphenylphosphoryl azide in the presence of a base, e.g. triethylamine or ethyldiisopropylamine, in a solvent, such as acetonitrile, benzene, or toluene, which provides, possibly after heating, the isocyanate, that can be hydrolyzed to afford amine 2.

Scheme 4. Preparation of intermediate 2

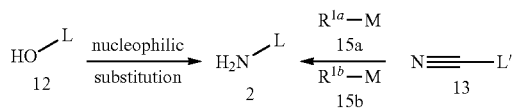

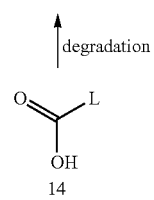

for L see scheme 1
L′ = A$^1$-Cy$^1$-A$^2$-Cy$^2$-Cy$^3$
or a truncated form of it that
allows attachment of missing
residues Cy$^1$, A$^2$, Cy$^2$, and/or Cy$^3$ Scheme 5 summarizes alternative synthetic routes to intermediate 4. Reacting amine 2 with epoxides (n=0) or oxetanes (n=1) of formula 16 is one possibility to obtain the desired intermediate 4, wherein Q is oxygen. This transformation works particularly well with epoxides and is optionally conducted in the presence of a base, e.g. triethylamine, ethyldiisopropyl-amine, or potassium carbonate, in solvents such as water, alcohol, N,N-dimethylformamide, N-methylpyrrolidinone, acetonitrile, or mixtures thereof, preferably at 0 to 140° C. Using analogous aldehyde 17 and amine 2 allows to access the same intermediate or the corresponding amino compound (Q=NR$^4$) via reductive amination with e.g. NaHB(O$_2$CCH$_3$)$_3$, NaH$_3$BCN, or NaBH$_4$, optionally in the presence of an acid such as acetic acid (methods for the reductive amination of aldehydes are described in Baxter, E. W. and Reitz, A. B. "Organic Reactions" Volume 59, Ed. Overman, L. E., Wiley Interscience, 2002). Another approach to compound 4 combines amine 2 and compound 18 bearing a leaving group such as chloride, bromide, iodide, mesylate, tosylate, or triflate. This nucleophilic substitution reaction is preferably carried out in the presence of a base, e.g. triethylamine, ethyl-diisopropyl-amine, K$_2$CO$_3$, or NaHCO$_3$, in tetrahydrofuran, 1,4-dioxane, acetonitrile, N,N-dimethylformamide, N-methylpyrrolidinone, dimethyl sulfoxide, alcohol, water or mixtures thereof, at 0 to 140° C.

Scheme 5. Alternative approaches to access intermediate 4

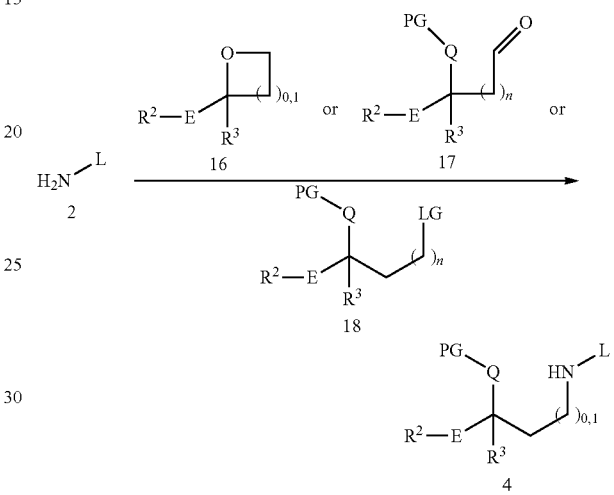

PG = protective group or H; for L see Scheme 1
LG = e.g. Cl, Br, I, O$_3$SMe, O$_3$STol, O$_3$SCF$_3$ Scheme 6 describes three synthetic routes to intermediate 22, which in turn is a competent precursor of intermediate 12. Transformation of compound 22 to 12, wherein LG denotes Cl, Br, or I, can be accomplished with N—Cl/Br/I-succinimide, tetrachloromethane, bromine, or iodine combined with a phosphine, e.g. triphenylphosphine, while the corresponding sulfonates of intermediate 12, LG denotes e.g. O$_3$SMe, O$_3$S-p-Tol, or O$_3$SCF$_3$, can be prepared by treating alcohol 22 with the corresponding sulfonyl chloride or anhydride, e.g. mesyl chloride, tosyl chloride, or trifluoromethanesulfonic anhydride, in the presence of a base, e.g. triethylamine or pyridine, in an inert solvent, preferably toluene, dichloromethane, ether, or 1,4-dioxane, at −20 to 60° C. Compound 22 can be prepared from olefin 19 by hydroboration with a borane, e.g. borane complexed with tetrahydrofuran, trimethylamine, or dimethyl sulfide, diethylborane, or 9-borabicyclo[3.3.1]nonane, preferably conducted in tetrahydrofuran at 0 to 60° C., followed by oxidation of the intermediate hydroboration product with e.g. hydrogen peroxide and sodium hydroxide in an aqueous solution at 0 to 80° C. The same compounds of formula 22 can be prepared from olefin 20 by oxidative cleavage of the double bond, e.g. ozonolysis or dihydroxylation, with e.g. osmium tetroxide, combined with glycol cleavage, with e.g. sodium periodate, followed by reduction of the aldehyde obtained thereafter, with e.g. NaBH$_4$. Ketone 21 provides intermediate 22 by addition of carbon nucleophile 10, wherein M is preferably Li, MgCl, MgBr, MgI, ZnCl, ZnBr, or ZnI. This transformation is optionally performed in the presence of an additive, such as CeCl$_3$ or a Lewis acid such as boron trifluoride etherate or a zinc halide, preferably in toluene, ether, tetrahydrofuran, 1,4-dioxane, 1,2-dimethoxyethane, or N-methylpyrrolidinone, at −78 to 60° C. The latter approach allows also direct access to intermediate 12 from ketone 21, provided that LG is compatible with nucleophile 10 and the specific reaction conditions employed.

nucleophile of $R^3$, e.g. allyltrimethylsilane or triallylborane, in the presence of a Lewis acid, e.g. $TiCl_4$, $Me_3SiO_3SCF_3$, or $BF_3*OEt_2$. Eventually, compound I" is obtained by treatment of compound 12' with amine 2 via nucleophilic substitution of the group LG with L-NH and subsequent cyclization of this

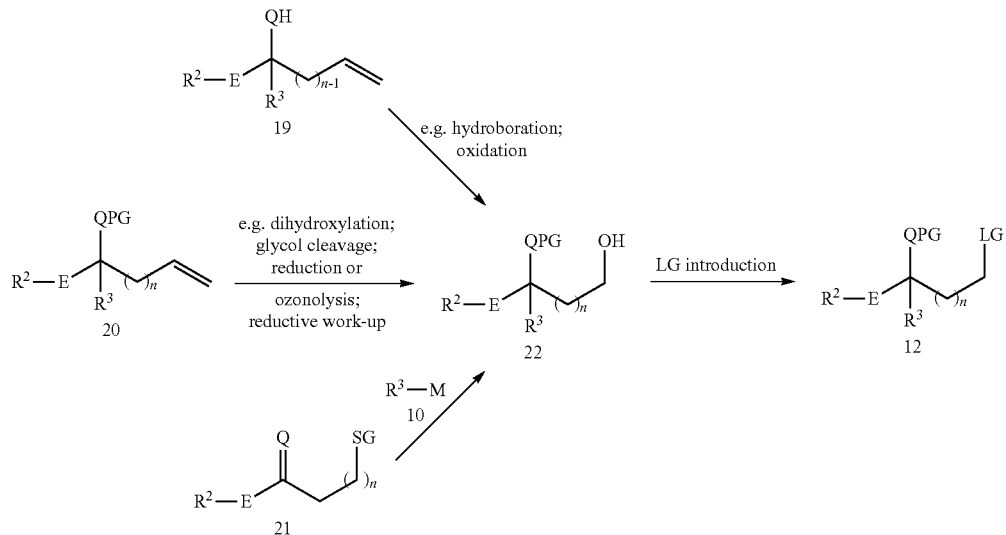

Scheme 6. Synthetic routes to intermediate 12

PG = protective group or H; for L see Scheme 1
LG is a leaving group, e.g. Cl, Br, I, $O_3SMe$, $O_3S$-p-Tol, $O_3SCF_3$
SG = LG or OH
M = e.g. Li, MgCl/Br/I, ZnCl/Br/I, $CeCl_2$ A more specific example for the preparation of a compound of general formula 4, wherein Q is NH or substituted N, in line with the last approach described in Scheme 6, is depicted below. Accordingly, compound 4' can be prepared from tert-butylsulfinylimine 8" by the addition of nucleophile 10 under the conditions described above. tert-Butylsulfinylimine 8", in turn, can be prepared from aminoketone 8' by reaction with tert-butylsulfinamide:

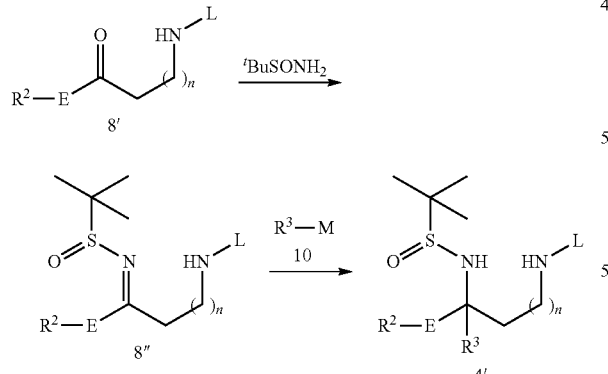

Compounds of the invention wherein Q is $CH_2$ (I") can be prepared by a Reformatsky reaction of zinc compounds of formula 10' with ketones of formula 7b bearing a leaving group, preferably chlorine (Scheme 7). Replacement of the hydroxy in compound 23 with $R^3$, which is preferably allyl or a derivative of it, can be accomplished by treatment with a intermediate by e.g. heating, optionally in the presence of a base, e.g. triethylamine, ethyl-diisopropyl-amine, or potassium carbonate.

Scheme 7. Strategy 4 to construct compounds of the invention

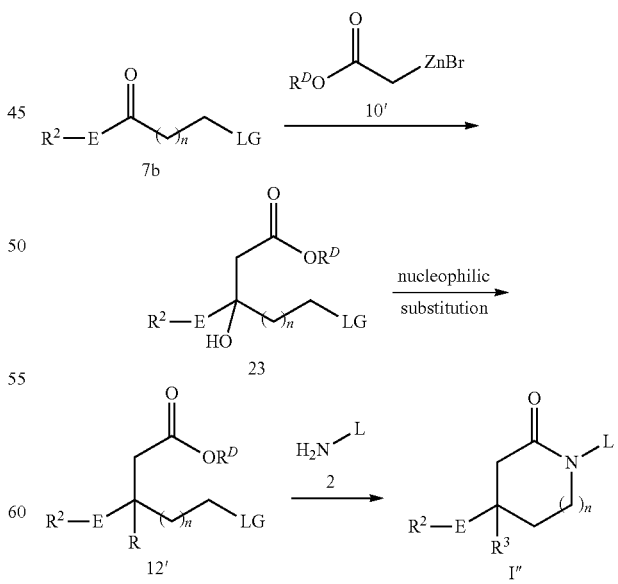

for L see Scheme 1
LG = e.g. Cl, Br, I, $O_3SMe$, $O_3S$-p-Tol
$R^D$ = e.g. Bn, $C_{1-4}$alkyl optionally mono- or polysubstituted with F or Cl In a departure from the approach presented in Scheme 7, intermediate 12" is cyclized to provide lactone 24 by e.g. heating, optionally in the presence of an additive such as a silver salt (Scheme 8). Lactone 24 can then be transformed by ozonolysis and subsequent reductive work-up, with e.g dimethyl sulfide or triphenylphosphine, or the sequence dihydroxylation, with e.g. osmium tetroxide, and glycol cleavage, with e.g. NaIO$_4$, to the aldehyde 25, wherein n is 1, or by hydroboration, e.g. with borane in complex with tetrahydrofuran, trimethylamine, or dimethyl sulfide, and subsequent oxidation, with e.g. hydrogen peroxide and sodium hydroxide, followed by oxidation of the alcohol formed thereafter, with e.g. dimethyl sulfoxide combined with SO$_3$*pyridine, acetic anhydride, or oxalyl chloride, to aldehyde 25, wherein n is 2. Aminolactone 26 can be prepared by reductive amination of aldehyde 25 with amine 2 using, for example, hydride reducing agents such as Na(NC)BH$_3$ or NaHB(O$_2$CCH$_3$)$_3$ in the presence of acetic acid. The concluding step in Scheme 8 can be accomplished by e.g. heating, optionally in the presence of a base, e.g. triethylamine, ethyl-diisopropyl-amine, or potassium carbonate.

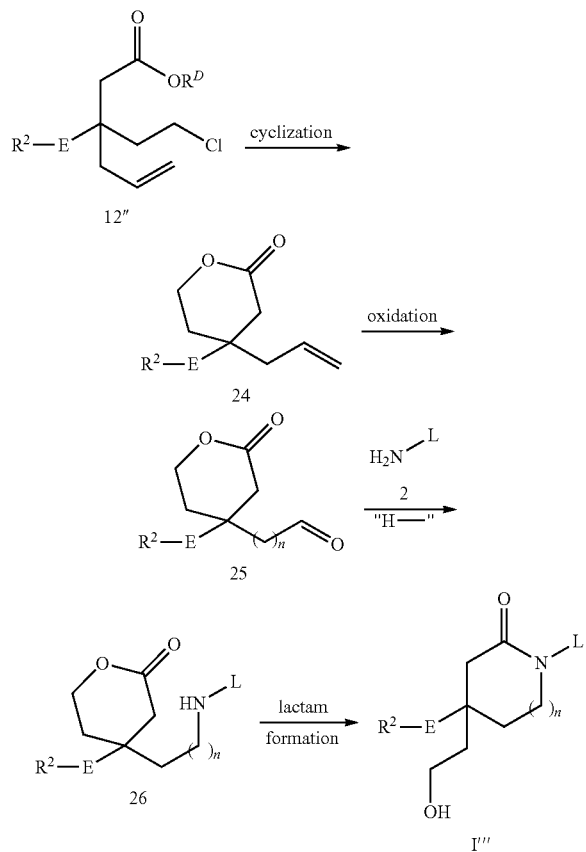

Scheme 8. Strategy 5 to construct compounds of the invention

R$^D$ = e.g. tBu, Bn, optionally mono- or polysubstituted with Me, NMe$_2$, OMe
for L see Scheme 1

In the following a few feasible derivatizations of compounds of general formula I or precursors thereof, obtained as described above, bearing certain functional groups to assemble other compounds of general formula I or precursors thereof are vicariously summarized. This compilation is by no means meant to be complete but is only supposed to give some possibilities by way of example.

If in the process of manufacture according to the invention a compound of general formula I or a precursor thereof is obtained which contains an amino, alkylamino, or imino group, this may be converted by acylation or sulfonylation into a corresponding acyl or sulfonyl compound of general formula I or a precursor thereof.

If a compound of general formula I or a precursor thereof is obtained which contains a hydroxy group, this may be converted by acylation or sulfonylation into a corresponding acyl or sulfonyl compound of general formula I or a precursor thereof.

If a compound of general formula I or a precursor thereof is obtained which contains a hydroxy group, this may be converted by alkylation into a corresponding ether of general formula I or a precursor thereof.

If a compound of general formula I or a precursor thereof is obtained which contains an amino, alkylamino, or imino group, this may be converted by alkylation or reductive alkylation into a corresponding alkyl compound of general formula I or a precursor thereof.

If a compound of general formula I or a precursor thereof is obtained which contains a nitro group, this may be converted by reduction into a corresponding amino compound.

If a compound of general formula I or a precursor thereof is obtained which contains an imino group, this may be converted by nitrosation and subsequent reduction into a corresponding N-amino-imino compound.

If a compound of general formula I or a precursor thereof is obtained which contains a C$_{1-4}$-alkyloxycarbonyl group, this may be converted by cleavage of the ester into the corresponding carboxy compound.

If a compound of general formula I or a precursor thereof is obtained which contains a carboxy group, this may be converted into a corresponding ester of general formula I or a precursor thereof.

If a compound of general formula I or a precursor thereof is obtained which contains a carboxy or ester group, this may be converted by reaction with an amine into a corresponding amide of general formula I or a precursor thereof.

If a compound of general formula I or a precursor thereof is obtained which contains an aromatic substructure, this may be derivatized with a chlorine, bromine, or iodine atom or a nitro, sulfonic acid, chlorosulfonyl, or acyl group by an electrophilic substitution reaction to a corresponding compound of general formula I or a precursor thereof.

If a compound of general formula I or a precursor thereof is obtained which contains an aromatic amino group, this may be transformed into a corresponding cyano, fluoro, chloro, bromo, iodo, hydroxy, mercapto, or azido derivatized compound of general formula I or a precursor thereof by diazotization and subsequent replacement of the diazo group with cyanide, fluoride, chloride, bromide, iodide, hydroxide, alkyl or hydrogen sulfide, or azide, respectively.

If a compound of general formula I or a precursor thereof is obtained which contains an aromatic amino group, this may be converted into a corresponding aryl derivatized aromatic compound of general formula I or a precursor thereof by diazotization of the amino group and subsequent replacement of the resulting diazo group with an appropriate aryl nucleophile mediated by a suited transition metal species.

If a compound of general formula I or a precursor thereof is obtained which contains an aromatic chloro, bromo, or iodo atom, or a trifluoromethylsulfonyloxy, mesyloxy, or tosyloxy group, this may be converted into a corresponding aryl, alkenyl, alkynyl, or alkyl derivatized compound of general formula I or a precursor thereof by replacement of the respective group by aryl, alkenyl, alkynyl, or alkyl using a transition metal species mediated process.

If a compound of general formula I or a precursor thereof is obtained which contains an aromatic chloro, bromo, or iodo atom, or a trifluoromethylsulfonyloxy, mesyloxy, or tosyloxy group, this may be replaced with hydrogen to give a corresponding aromatic compound of general formula I or a precursor thereof.

If a compound of general formula I or a precursor thereof is obtained which contains two heteroatoms at adjacent carbon atoms that are amino and hydroxy, amino, or mercapto, these heteroatoms may be linked via a carboxy carbon atom to form a cyclic amidine, imino ester, or imino thioester substructure that may be part of an aromatic ring.

If a compound of general formula I or a precursor thereof is obtained which contains a cyano group, this may be converted by reduction into an aminoalkyl derivatized compound of general formula I or a precursor thereof.

If a compound of general formula I or a precursor thereof is obtained which contains a cyano group, this may be converted into an N-hydroxycarbamimidoyl group by the treatment with hydroxylamine.

If a compound of general formula I is obtained which contains an N-hydroxycarbamimidoyl group, this may be converted to an oxadiazole derivatized compound of general formula I or a precursor thereof by the treatment with a carboxylic or related group.

If a compound of general formula I or a precursor thereof is obtained which contains an aminocarbonyl group, this may be converted by dehydration into a corresponding cyano compound of general formula or a precursor thereof I.

If a compound of general formula I or a precursor thereof is obtained which contains a keto or aldehydic group, this may be converted by reduction into a corresponding hydroxy compound of general formula I or a precursor thereof.

If a compound of general formula I or a precursor thereof is obtained which contains a carboxylic acid or aminocarbonyl group, this may be converted by a rearrangement reaction into a corresponding amino derivatized compound of general formula I or a precursor thereof.

If a compound of general formula I or a precursor thereof is obtained which contains a keto or aldehyde group, this may be converted into an alkenyl derivatized compound of general formula I or a precursor thereof.

If a compound of general formula I or a precursor thereof is obtained which contains an olefinic C=C double or a C≡C triple bond, this may be reduced to give the corresponding saturated compound of general formula I or a precursor thereof.

If a compound of general formula I or a precursor thereof is obtained which contains a keto or aldehydic group, this may be converted into a corresponding tertiary or secondary hydroxy compound of general formula I or a precursor thereof.

If a compound of general formula I or a precursor thereof is obtained which contains a carboxylic ester group, this may be converted into a tertiary alcohol by the addition of two equivalents of an organo metal compound.

If a compound of general formula I or a precursor thereof is obtained which contains a primary or secondary hydroxy group, this may be converted by oxidation into a corresponding carbonyl compound of general formula I or a precursor thereof.

If a compound of general formula I or a precursor thereof is obtained which contains an olefinic bond, this may be converted into a corresponding hydroxy compound of general formula I or a precursor thereof by hydroboration followed by oxidation.

If a compound of general formula I or a precursor thereof is obtained which contains an olefinic bond, this may be converted by dihydroxylation into a corresponding 1,2-dihydroxy compound of general formula I or a precursor thereof.

If a compound of general formula I or a precursor thereof is obtained which contains an olefinic bond, this may be converted by ozonolysis into a corresponding carbonyl compound of general formula I or a precursor thereof.

If a compound of general formula I or a precursor thereof is obtained which contains an olefinic bond, this may be converted into a corresponding hydroxy compound of general formula I or a precursor thereof by epoxidation followed by oxirane opening with a hydride source.

If a compound of general formula I or a precursor thereof is obtained which contains an olefinic bond, this may be converted by Wacker oxidation into a corresponding carbonyl compound of general formula I or a precursor thereof.

If a compound of general formula I or a precursor thereof is obtained which contains an olefinic bond, this may be converted by hydrocyanation into a corresponding cyano compound of general formula I or a precursor thereof.

If a compound of general formula I or a precursor thereof is obtained which contains a cyano group, this may be converted by water addition into a corresponding aminocarbonyl compound of general formula I or a precursor thereof.

If a compound of general formula I or a precursor thereof is obtained which contains an electron deficient aromatic substructure that bears a leaving group such as an halide or a pseudo-halide, the leaving group may be replaced with a nucleophile to furnish a corresponding compound of general formula I or a precursor thereof.

The subsequent esterification is optionally carried out in a solvent such as methylene chloride, N,N-dimethylformamide, benzene, toluene, chlorobenzene, tetrahydrofuran, 1,4-dioxane, or mixtures thereof or particularly advantageously in the corresponding alcohol optionally in the presence of an acid, e.g. hydrochloric acid, or a dehydrating agent, e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-carbonyldiimidazole, N,N'-dicyclohexylcarbodiimide, triphenylphosphine combined with carbon tetrachloride, or combinations thereof optionally in the presence of 4-dimethylaminopyridine and/or 1-hydroxybenzotriazole. The reactions are conducted between 0 and 150° C., preferably between 0 and 80° C.

The ester formation may also be carried out by reacting a compound which contains a carboxy group with a corresponding alkyl halide in the presence of a base.

The subsequent acylation or sulfonylation is optionally carried out in a solvent such as methylene chloride, N,N-dimethylformamide, benzene, toluene, chlorobenzene, tetrahydrofuran, 1,4-dioxane, or mixtures thereof with a corresponding acyl or sulfonyl electrophile, optionally in the presence of a tertiary organic base, an inorganic base, or a dehydrating agent. Routinely used agents are e.g. isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-carbonyldiimidazole, triphenylphosphine combined with carbon tetrachloride, or combinations thereof that may be employed in the presence of 4-dimethylaminopyridine and/or 1-hydroxybenzotriazole at temperatures between 0 and 150° C., preferably between 0 and 80° C.

The subsequent alkylation is optionally carried out in methylene chloride, N,N-dimethylformamide, benzene, toluene, chlorobenzene, tetrahydrofuran, 1,4-dioxane, or mixtures thereof with an alkylating agent such as a corresponding halide or sulfonic acid ester, e.g. methyl iodide, ethyl bromide, dimethyl sulfate, or benzyl chloride, optionally in the presence of a tertiary organic base or an inorganic base at temperatures between 0 and 150° C., preferably between 0 and 100° C.

The subsequent reductive alkylation is carried out with a corresponding carbonyl compound such as formaldehyde, acetaldehyde, propionaldehyde, acetone, or butyraldehyde in the presence of a complex metal hydride, such as sodium borohydride, lithium borohydride, sodium triacetoxyborohydride, or sodium cyanoborohydride, conveniently at a pH of 6-7 and ambient temperature, or using hydrogen in the presence of a transition metal catalyst, e.g. palladium on charcoal, at hydrogen pressures of 1 to 5 bar. Methylation may also be carried out in the presence of formic acid as reducing agent at elevated temperature, e.g. between 60 and 120° C.

The subsequent reduction of a nitro group is carried out, for example, with hydrogen and a catalyst such as palladium on carbon, platinum dioxide, or Raney nickel, or using other reducing agents such as tin(II) chloride, iron, or zinc optionally in the presence of an acid such as acetic acid.

The subsequent nitrosation of an imino group followed by reduction to obtain an N-amino-imino compound is carried out, for example, with an alkyl nitrite such as isoamyl nitrite to form the N-nitroso-imino compound that is then reduced to the N-amino-imino compound using, for example, zinc in the presence of an acid such as acetic acid.

The subsequent cleaving of a $C_{1-4}$-alkyloxycarbonyl group to obtain the carboxy group is carried out, for example, by hydrolysis with an acid such as hydrochloric acid or sulfuric acid or an alkali metal hydroxide such as lithium hydroxide, sodium hydroxide, or potassium hydroxide. The tert-butyl group is preferably removed by treatment with a strong acid, e.g. trifluoroacetic acid or hydrochloric acid, in an inert solvent such as dichloromethane, 1,4-dioxane, or ethyl acetate.

The subsequent amide formation is carried out by reacting a corresponding reactive carboxylic acid derivative with a corresponding amine optionally in a solvent such as methylene chloride, N,N-dimethylformamide, benzene, toluene, chlorobenzene, tetrahydrofuran, 1,4-dioxane, or mixtures thereof, or without an solvent in an excess of the amine, optionally in the presence of a tertiary organic base, an inorganic base, 4-dimethylaminopyridine, and/or 1-hydroxybenzotriazole, at temperatures between 0 and 150° C., preferably between 0 and 80° C. Using the carboxylic acid may lead to the desired amide by in situ activation of the carboxy function with e.g. isobutyl chloroformate, thionyl chloride, oxalyl chloride, trimethylchlorosilane, phosphorus trichloride, phosphorus pentoxide, N,N'-carbonyldiimidazole, triphenylphosphine combined with carbon tetrachloride, 2-(1H-benzotriazol-1-yl)-1,1,3,3-tetramethyluronium tetrafluoroborate, N,N'-dicyclohexylcarbodiimide, or combinations thereof.

The subsequent introduction of a chlorine, bromine, or iodine atom into an aromatic substructure may be carried out by reacting the aromatic compound with an appropriate electrophile of the respective halogen atom. Suited chlorine and bromine electrophiles may be e.g. N-halosuccinimide, HOCl, HOBr, tert-BuOCl, tert-BuOBr, chlorine, bromine, dibromoisocyanuric acid, pyridinium dichlorobromate, pyridinium tribromide, or sulfuryl chloride that may be used alone or in combination with an acid, e.g. hydrochloric acid, hydrobromic acid, tetrafluoroboric acid, triflic acid, sulfuric acid, or acetic acid, or a Lewis acid, e.g. iron(III) halide, boron trifluoride hydrate, boron trifluoride etherate, or aluminum halide. Further useful combinations may be LiBr and ceric ammonium nitrate, KCl or KBr with Oxone®, or KBr and sodium perborate. Suited iodine electrophiles may be generated from iodine and an oxidizing agent such as nitric acid, sulfur trioxide, manganese dioxide, $HIO_3$, hydrogen peroxide, sodium periodate, peroxydisulfates, and Oxone®. Further suited iodine electrophiles may be e.g. iodine chloride, dichloroiodates, and N-iodosuccinimide. These iodine electrophiles are optionally used without an additive or in the presence of an acid such as acetic acid, trifluoroacetic acid, or sulfuric acid or a Lewis acid such as boron trifluoride hydrate or copper salts. If a nitro group is to be introduced appropriate nitro electrophile sources may be, for instance, nitric acid, acetyl nitrate, ceric ammonium nitrate, sodium nitrate, $N_2O_5$, alkyl nitrate, and nitronium tetrafluoroborate. Some of these reagents may be used without an additive, though, several of them are better used in combination with an acid, e.g. sulfuric acid or triflic acid, acetic anhydride, trifluoroacetic anhydride, Lewis acid, e.g. ytterbium triflate or iron acetate, $P_2O_5$, or a base. The $SO_3H$ group may be introduced by reacting the aromatic compound with, for example, concentrated sulfuric acid, $SO_3$, $ClSO_3H$, or $ClSO_2NMe_2$ combined with indium triflate. Reacting the aromatic compound with $ClSO_3H$ gives the corresponding chlorosulfonylated derivative that may be hydrolyzed to the sulfonic acid. Acylating the aromatic part is conducted using an acyl electrophile that may be generated from the respective acyl halide, e.g. chloride, or acyl anhydride and a Lewis acid such as aluminum halide, diethylaluminum halide, indium halide, iron(III) halide, tin(IV) halide, boron trifluoride, titanium(IV) halide, or a Brønsted acid, e.g. sulfuric acid or triflic acid. The formyl group is preferably introduced using the so-called Vilsmeier or Vilsmeier-Haack conditions: dialkylformamide combined with phosgene, thionyl chloride, $POCl_3$, or oxalyl chloride. Preferred solvents for the electrophilic substitutions described may differ depending on the electrophile employed; in the following some more generally applicable are mentioned: methylene chloride, 1,2-dichloroethane, chlorobenzene, dichlorobenzene, ether, 1,4-dioxane, fluorinated hydrocarbons, hexanes, quinoline, and acetonitrile. Temperatures preferably applied range from 0 to 180° C.

The subsequent replacement of an aromatic amino group is initiated by diazotization of the amino group using a nitrous acid or nitrosonium source or equivalent such as a nitrite salt combined with an acid, e.g. sodium nitrite and hydrochloric acid, nitrosonium tetrafluoroborate, or an alkylnitrite, e.g. tert-butyl nitrite or iso-amyl nitrite. The diazotization is optionally carried out in methylene chloride, 1,2-dichloroethane, N,N-dimethylformamide, N-methylpyrrolidinone, benzene, toluene, chlorobenzene, tetrahydrofuran, water, ethyl acetate, alcohol, ether, 1,2-dimethoxyethane, 1,4-dioxane, or mixtures thereof at temperatures between −10 and 100° C. (diazotization of amino groups is detailed in, for example, *Angew. Chem. Int. Ed.* 1976, 15, 251). The subsequent displacement of the diazo group with a cyano group, chlorine, or bromine atom using copper cyanide, chloride, or bromide, respectively, is known as the Sandmeyer reaction (see e.g. March's Advanced Organic Chemistry, Michael B. Smith and Jerry March, John Wiley & Sons Inc., 6. Ed., New Jersey, 2007 and references quoted therein); the reaction is optionally conducted between −10 and 120° C. in one of the solvents or mixtures mentioned above. The replacement of the diazo group with a fluorine atom may be achieved with a tetrafluoroborate salt or tetrafluoroboric acid and heating to 20 to 160° C.; the reaction is known as the Schiemann reaction. Iodine may be introduced by treatment of the diazo compound with an iodide salt, e.g. sodium iodide, preferably using water or an aqueous solvent mixture at temperatures between 0 and 120° C. The diazo group is replaced with hydroxy using water or an aqueous solvent mixture at temperatures between 0 and 180° C. The reaction usually works without further additives but the addition of copper oxide or strong acid may be advantageous. Mercapto or alkylmercapto may be introduced via their corresponding disulfide salts or dialkyldisulfides at temperatures between 0 and 120° C.; depending on the sulfur species used an inert solvent or aqueous solvent system may be preferred (see e.g. *Synth. Commun.* 2001, 31, 1857 and references quoted therein).

The subsequent replacement of an aromatic amino group by an aryl group may be accomplished via the corresponding diazo compound obtainable as described above. The reaction with an aryl nucleophile, preferably an aryl boronic acid, boronic ester, trifluoroborate, zinc halide, or stannane, is conducted in the presence of a transition metal species derived from palladium, nickel, rhodium, copper, or iron, preferably palladium. The active catalyst may be a complex of the transition metal with ligands such as e.g. phosphines, phosphites, imdiazole carbenes, imidazolidine carbenes, dibenzylideneacetone, allyl, or nitriles, an elemental form of the transition metal such as palladium on carbon or nanoparticles, or salts such as chloride, bromide, acetate, or trifluoroacetate. The diazo compound is preferably employed as its tetrafluoroborate salt optionally in water, N-methylpyrrolidinone, N,N-dimethylformamide, methylene chloride, benzene, toluene, tetrahydrofuran, ethyl acetate, alcohol, ether, 1,2-dimethoxyethane, 1,4-dioxane, or mixtures thereof at temperatures between 10 and 180° C., preferably between 20 and 140° C.

The subsequent replacement of an aromatic chloro, bromo, or iodo atom or an aromatic trifluoromethylsulfonyloxy, mesyloxy, or tosyloxy group with an aryl, alkenyl, alkynyl, or alkyl residue is preferably mediated by a transition metal species derived from palladium, nickel, copper, or iron. The active catalyst may be a complex of the transition metal with ligands such as phosphines, e.g. tri-tert-butylphosphine, tricyclohexylphosphine, 2-(substituted phenyl)phenyl-dicyclohexylphosphines, 2-(substituted phenyl)phenyl-di-tert-butylphosphines, 1,1'-bis(diphenylphosphino)ferrocene, triphenylphosphine, tritolylphosphine, or trifurylphosphine, phosphites, 1,3-disubstituted imdiazole carbenes, 1,3-disubstituted imidazolidine carbenes, dibenzylideneacetone, allyl, or nitriles, an elemental form of the transition metal such as palladium on carbon or nanoparticles of iron or palladium, or a salt such as fluoride, chloride, bromide, acetate, triflate, or trifluoroacetate. The replacement reaction is preferably conducted with a trifluoroborate, boronic acid, or boronic ester (Suzuki or Suzuki-type reaction), zinc halide (Negishi or Negishi-type reaction), stannane (Stille or Stille-type reaction), silane (Hiyama or Hiyama-type reaction), magnesium halide (Kumada or Kumada-type reaction) of the aryl, alkenyl, or alkyl residue to be introduced. The terminal alkyne is preferably used as such or as its zinc acetylide derivative. Depending on the nature of the electrophilic and nucleophilic reaction partners additives such as halide salts, e.g. lithium chloride, potassium fluoride, tetrabutylammonium fluoride, hydroxide sources such as potassium hydroxide or potassium carbonate, silver salts such as silver oxide or triflate, and/or copper salts such as copper chloride or copper thiophene-2-carboxylate may be advantageous or even essential. Copper iodide is a preferred additive in the coupling with terminal alkynes (Sonogashira reaction). The coupling reactions are preferably conducted in benzene, toluene, ether, tetrahydrofuran, 1,2-dimethoxyethane, 1,4-dioxane, N,N-dimethylformamide, N,N-dimethylacetamide, N-methylpyrrolidinone, alcohol, water, or mixtures thereof, though, depending on the nucleophile some of them are less or not suited at all. Preferred temperatures are in the range from −10 to 180° C.

The subsequent replacement of an aromatic chlorine, bromine, or iodine atom or an aromatic trifluoromethylsulfonyloxy, mesyloxy, or tosyloxy group with a hydrogen atom is preferably mediated by a transition metal species derived from palladium, nickel, platinum, or rhodium. The active catalyst may be a complex of the transition metal with ligands, an elemental form, or a salt of the transition metal as mentioned above. Raney nickel or palladium on carbon are among the preferred catalyst species. Suited hydrogen sources may be hydrogen, preferably at pressures of 1 to 10 bar, silanes, e.g. trialkoxysilane or polymethylhydrosiloxane, boranes, hydrides, e.g. alkali metal borohydride, formic acid, or formates, e.g. ammonium formate. The reactions are preferably carried out in N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof at −10 to 180° C., more preferably at 20 to 140° C.

The subsequent cyclization starting from a compound bearing two heteroatoms at adjacent carbon atoms is optionally conducted with a carboxy equivalent such as nitrile, carboxylic chloride or fluoride, carboxylic acid, ketene, carboxylic ester, or carboxylic thioester. The overall transformation comprises two reaction steps: attachment of the carboxy equivalent to one of the two heteroatoms followed by cyclization with the other heteroatom. The first step is an amide formation with the amino functionality that may be carried out as described hereinbefore. The ensuing reaction step, cyclization with the second heteroatom, may be accomplished by heating in the presence of an acid, e.g. acetic acid, trifluoroacetic acid, sulfuric acid, or hydrochloric acid, or a base, e.g. sodium hydroxide, sodium ethoxide, or sodium tert-butoxide. The use of dehydrating reagents such as anhydrides, e.g. acetic anhydride, orthoesters, e.g. trimethyl orthoformate, thionyl chloride, phosgene, diphosgene, triphosgene, phosphorous oxychloride, phosphorous pentachloride, dialkylcarbodiimides, combinations with phosphines, e.g. triphenylphosphine or trialkylphosphine with dialkyl azodicarboxylates, bromine, iodine, or 1,2-dihaloethanes, e.g. 1,2-dibromotetrafluoroethane, may be advantageous. The reactions are preferably carried out in inert solvents or mixtures such as methylene chloride, 1,2-dichloroethane, benzene, toluene, tetrahydrofuran, ether, or combinations thereof, though, cyclization in the presence of an acid or a base may also be conducted in water or an alcohol, e.g. methanol, ethanol, iso-propanol, or tert-butanol, or combinations with these solvents. The reactions are carried out at temperatures between 0 and 200° C., preferably between 20 and 140° C.

The subsequent reduction of a cyano group to obtain an aminomethyl group is preferably conducted with hydrogen in the presence of a transition metal species or with a hydride. Suited transition metals may be derived from palladium, nickel, platinum, rhodium, or ruthenium such as palladium on charcoal, palladium hydroxide, platinum oxide, or Raney nickel that may be used in solvents such as ethyl acetate, alcohols, e.g. methanol or ethanol, dichloromethane, tetrahydrofuran, ether, benzene, toluene, N,N-dimethylformamide, or N-methylpyrrolidinone at hydrogen pressures between 1 and 10 bar and at temperatures between 0 and 160° C. Additives such as acids, e.g. hydrochloric acid, methanesulfonic acid, sulfuric acid, or acetic acid, may be beneficial for the reduction with transition metal catalysts. Among the preferred hydride sources are e.g. borohydrides, e.g. sodium borohydride, potassium tri-sec-butylborohydride, borane, or lithium triethylborohydride, and alanates, e.g. lithium aluminum hydride or diisobutylaluminum hydride. Some of these reagents are best used in combination with nickel chloride or cobalt chloride as sodium borohydride. These reagents may be used in e.g. tetrahydrofuran, ether, 1,4-dioxane, 1,2-dimethoxyethane, dichloromethane, 1,2-dichloroethane, benzene, or toluene; some are also compatible with alcoholic or aqueous solutions. Preferred reaction temperatures range from −80 to 160° C., more preferred from −40 to 80° C.

The subsequent formation of a N-hydroxycarbamimidoyl group from a cyano group may be carried out by the treatment of the cyano compound with hydroxylamine. The reaction is preferably conducted in aqueous or alcoholic solvents at temperatures between 0 and 140° C.

The subsequent formation of an oxadiazole from an N-hydroxycarbamimidoyl is conducted with a carboxy equivalent such as nitrile, carboxylic chloride or fluoride, carboxylic acid, ketene, carboxylic ester, or carboxylic thioester. The transformation is related to the formation of a ring starting from two heteroatoms at adjacent carbon atoms described above and may be carried out analogously.

The subsequent formation of a cyano group from an aminocarbonyl group is preferably conducted by using a dehydrating reagent such as anhydride, e.g. acetic anhydride, trifluoroacetic anhydride, or triflic anhydride, phosgene, thionyl chloride, oxalyl chloride, $POCl_3$, $PCl_5$, $P_4O_{10}$, triphenylphosphite, or triphenyl- or trialkylphosphine combined with tetrachloromethane, 1,2-dibromotetrafluoroethane, or bromine. The reactions are preferably carried out in dichloromethane, 1,2-dichloroethane, hexanes, ether, 1,4-dioxane, benzene, toluene, acetonitrile, mixtures thereof, or without a solvent at temperatures between 0 and 140° C. Additives such as amines, e.g. pyridine or triethylamine, or N,N-dimethylformamide may be beneficial.

The subsequent reduction of a keto or an aldehydic group to obtain a secondary or primary alcohol may be carried out with a complex metal hydride such as sodium borohydride, lithium borohydride, lithium triethylborohydride, diisobutylaluminum hydride, or lithium aluminum hydride. The reductions may be conducted in e.g. dichloromethane, 1,2-dichloroethane, hexanes, ether, 1,4-dioxane, tetrahydrofuran, N,N-dimethylformamide, N-methylpyrrolidone, benzene, toluene, alcohols, e.g. methanol, water, or mixtures thereof, though, not all reducing agents are compatible with all of these solvents. Preferred temperatures range from −80 to 140° C. depending on the reducing power of the reagent. Alternatively, hydrogen in the presence of a transition metal catalyst may be used for the reduction.

The subsequent conversion of a carboxy group into an amino group by rearrangement may be accomplished by heating an acyl azide resulting in the formation of an isocyanate (Curtius rearrangement). The isocyanate may be hydrolyzed to produce the free amine or converted into a urea or carbamate derivative by treatment with an amine or an alcohol, respectively. The acyl azide may be obtained by treating an appropriate acyl electrophile, e.g. acyl chloride, carboxylic anhydride, or carboxylic ester, with an azide source, such as e.g. sodium azide or trimethylsilyl azide, in a solvent such as 1,4-dioxane, 1,2-dimethoxyethane, acetonitrile, tetrahydrofuran, dichloromethane, 1,2-dichloroethane, N-methylpyrrolidinone, N,N-dimethylformamide, toluene, benzene, hexanes, or mixtures thereof; water or alcohols may be usable in certain cases as well. The reactions are routinely carried out between −10 and 120° C. Alternatively, the acyl electrophile may be generated in situ from the acid and then converted into the acyl azide: diphenylphosphoryl azide in the presence of a base, e.g. triethylamine or ethyldiisopropylamine, in a solvent such as acetonitrile, benzene, toluene, or an alcohol at elevated temperature has proven to be an effective reagent for this direct conversion. The direct conversion may also be achieved with hydrazoic acid and an acid catalyst such as sulfuric acid in e.g. chloroform at elevated temperatures (Schmidt reaction). Another method to accomplish this overall transformation is the Lossen rearrangement: starting from an acyl electrophile such as acyl chloride the corresponding suited hydroxamic acid derivative is formed that in turn rearranges to give the isocyanate and then the amine by heating and/or treatment with a base, e.g. sodium hydroxide (see e.g. *J. Org. Chem.* 1997, 62, 3858 and *Synthesis* 1990, 1143 and references quoted therein).

An unsubstituted carboxylic amide may be converted into an amine by the so-called Hoffmann rearrangement. Among the suited reagents for this transformation are NaOBr, bromine combined with sodium methoxide, N-bromosuccinimide and sodium methoxide, $PhI(O_2CCF_3)_2$, and $PhI(OH)OTs$.

The subsequent conversion of an aldehydic or a keto functionality into an olefin may be accomplished by, for example, the so-called Wittig reaction and modifications thereof, Peterson olefination, and Julia reaction and modifications thereof. These reactions have large precedence in organic syntheses and are detailed in e.g. March's Advanced Organic Chemistry, Michael B. Smith and Jerry March, John Wiley & Sons Inc., 6. Ed., New Jersey, 2007 and references quoted therein.

The subsequent reduction of a C=C double or C≡C triple bond is preferably conducted with hydrogen in the presence of a transition metal species derived from palladium, nickel, platinum, ruthenium, or rhodium, preferably Raney nickel, palladium on charcoal, platinum oxide, and $RhCl(PPh)_3$. The reactions are preferably carried out in methylene chloride, N,N-dimethylformamide, N,N-dimethylacetamide, N-methylpyrrolidinone, benzene, toluene, tetrahydrofuran, water, ethyl acetate, alcohol, ether, 1,2-dimethoxyethane, 1,4-dioxane, or mixtures thereof, at 0 to 180° C., more preferably at 20 to 140° C., and hydrogen pressures of 1 to 10 bar, preferably 1 to 5 bar.

The subsequent transformation of an aldehyde or a ketone to a secondary or tertiary alcohol is preferably accomplished by addition of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at −80 to 80° C.

The subsequent transformation of a carboxylic ester into a tertiary hydroxy group is preferably conducted with two or more equivalents of a carbon nucleophile, e.g. alkyl, allyl, alkenyl, aryl, or alkynyl lithium, magnesium, or cerium compound, in tetrahydrofuran, ether, 1,4-dioxane, 1,2-dimethoxyethane, toluene, hexanes, or mixtures thereof, at temperatures of −80 to 80° C.

The subsequent oxidation of a primary or secondary hydroxy compound may be achieved by using an oxidizing agent, such as dimethyl sulfoxide combined with e.g. oxalyl chloride, acetic anhydride, $SO_3$*pyridine, or dicyclohexylcarbodiimide, pyridinium chlorochromate (PCC), pyridinium dichromate (PDC), Dess-Martin periodinane, manganese dioxide, 2,2,6,6-tetramethylpiperidine-N-oxide (TEMPO) optionally combined with a co-oxidant, or tetrapropylammonium perrhutenate (TPAP) combined with a co-oxidant agent such as N-methyl-morpholine-N-oxide, which are optionally used in the presence of a base, e.g. triethylamine, preferably in toluene, dichloromethane, or 1,2- dichloroethane, at −70 to 60° C. Alternatively, the transformation may be performed as an Oppenauer oxidation with e.g. Al(OtBu)$_3$ and acetone.

The subsequent hydroboration and oxidation of an olefinic bond is conducted with a borane, e.g. borane complexed with tetrahydrofuran, trimethylamine, or dimethyl sulfide, diethylborane, thexylborane, 9-borabicyclo[3.3.1]nonane, NaBH$_4$ combined with BF$_3$ or TiCl$_4$, or dichloroborane, preferably used in tetrahydrofuran at −20 to 60° C. The hydroboration product is subsequently treated with e.g. hydrogen peroxide and sodium hydroxide in an aqueous solution to replace the boron group in the intermediate with hydroxy.

The subsequent dihydroxylation of an olefinic bond is preferably conducted with osmium tetroxide or potassium osmate combined with a co-oxidant, e.g. N-methyl-morpholine-N-oxide or K$_3$Fe(CN)$_6$, preferably in water combined with tert-BuOH, tetrahydrofuran, and/or 1,4-dioxane, at −20 to 60° C.

The subsequent cleavage of an olefinic bond by ozonolysis is conducted with ozone, preferably in dichloromethane at −50 to −78° C. The intermediate obtained thereafter may be transformed into a carbonyl compound by treatment with e.g. dimethyl sulfide, zinc combined with acetic acid, hydrogen in the presence of palladium, or triphenylphosphine. Treatment of the intermediate with sodium borohydride or lithium aluminum hydride affords the corresponding hydroxy compound.

The subsequent epoxidation of an olefinic bond is preferably conducted with m-chloroperbenzoic acid (mCPBA), hydrogen peroxide combined with formic acid or acetic acid, or Oxone® combined with acetone or 1,1,1-trifluoroacetone, preferably in dichloromethane at −20 to 40° C. The oxirane ring can be opened with a hydride source such as lithium aluminum hydride or lithium triethylborohydride in an inert solvent, e.g. tetrahydrofuran, to furnish the hydroxy compound.

The subsequent Wacker oxidation of an olefinic bond is preferably conducted with PdCl$_2$ and CuCl or CuCl$_2$, in the presence of oxygen, in an aqueous solvent to provide the corresponding carbonyl compound.

The subsequent hydrocyanation of an olefinic bond can be conducted with 4-tolylsulfonyl cyanide in the presence of phenylsilane and a cobalt catalyst (see e.g. *Angew. Chem.* 2007, 119, 4603-6).

The subsequent formal water addition to cyano groups can be done by treating an aqueous solution of the nitrile with a strong acid, e.g. sulfuric acid or hydrochloric acid, or a base, e.g. NaOH or KOH, optionally at elevated temperature, preferably at 0 to 140° C. Alternatively, this transformation can be achieved in an aqueous solution with a transition metal catalyst such as PdCl$_2$.

The subsequent replacement of a leaving group on an electron-deficient aromatic or heteroaromatic structure with a primary or secondary amine is preferably performed in N,N-dimethylformamide, N,N-dimethylacetamide, N-methylpyrrolidinone, dimethyl sulfoxide, tetrahydrofuran, 1,4-dioxane, alcohol, water, or mixtures thereof, optionally in the presence of a base, such as triethylamine, ethyl-diisopropyl-amine, pyridine, 1,8-diazabicyclo[5.4.0]undec-7-ene, NaOtBu, KOtBu, Na$_2$CO$_3$, K$_2$CO$_3$, Cs$_2$CO$_3$, or CaO, at temperatures ranging from 0 to 180° C. An O-nucleophile is introduced preferably in N,N-dimethylformamide, N,N-dimethylacetamide, N-methylpyrrolidinone, dimethyl sulfoxide, tetrahydrofuran, 1,4-dioxane, or mixtures thereof or without an additional solvent, using preferably NaH, KOtBu, K$_2$CO$_3$, or Cs$_2$CO$_3$ as base, at 0 to 180° C.

The synthetic routes and transformations presented may rely on the use of protecting groups. Suitable protecting groups for the respective functionalities and their removal are described hereinafter and may analogously be employed (see also: *Protecting Groups*, Philip J. Kocienski, 3$^{rd}$ edition, Georg Thieme Verlag, Stuttgart, 2004 and references quoted therein).

For example, a protecting group for a hydroxy group may be a trimethylsilyl, tert-butyldimethylsilyl, triisopropylsilyl, acetyl, pivaloyl, benzoyl, methyl, tert-butyl, allyl, trityl, benzyl, 4-methoxybenzyl, tetrahydropyranyl, methoxymethyl, ethoxymethyl, or 2-trimethylsilylethoxymethyl group, protecting groups for a carboxy group may be trimethylsilyl, methyl, ethyl, tert-butyl, allyl, benzyl, or tetrahydropyranyl, protecting groups for a ketone or aldehyde may be a ketal or acetal, respectively, e.g. derived from methanol, ethylene glycol, propane-1,3-diol, or propane-1,3-dithiol, protecting groups for an amino, alkylamino, or imino group may be methyl, formyl, acetyl, trifluoroacetyl, ethoxycarbonyl, tert-butoxycarbonyl, benzyloxycarbonyl, benzyl, 4-methoxybenzyl, or 2,4-dimethoxybenzyl and for the amino group additionally phthalyl and tetrachlorophthalyl, and protecting groups for a terminal alkyne may be trimethylsilyl, triisopropylsilyl, tert-butyldimethylsilyl, or 2-hydroxyprop-2-yl.

Any acyl protecting group may be cleaved, for example, hydrolytically in an aqueous solvent, e.g. in water, isopropanol/water, acetic acid/water, tetrahydrofuran/water, or 1,4-dioxane/water, in the presence of an acid such as trifluoroacetic acid, hydrochloric acid, or sulfuric acid or in the presence of an alkali metal base such as lithium hydroxide, sodium hydroxide, or potassium hydroxide at temperatures between 0 and 120° C., preferably between 10 and 100° C. The transformation may be conducted aprotically with e.g. iodotrimethylsilane in dichloromethane or 1,2-dichlorethane at −70 to 60° C. Trifluoroacetyl is also cleaved by treating with an acid such as hydrochloric acid optionally in a solvent such as acetic acid at temperatures between 50 and 120° C. or by treating with aqueous sodium hydroxide solution optionally in an additional solvent such as tetrahydrofuran or methanol at temperatures between 0 and 80° C.

Any acetal or ketal protecting group used may be cleaved, for example, hydrolytically in an aqueous solvent, e.g. water, isopropanol/water, acetic acid/water, tetrahydrofuran/water, or 1,4-dioxane/water, in the presence of an acid such as acetic acid, trifluoroacetic acid, hydrochloric acid, or sulfuric acid at temperatures between 0 and 120° C., preferably between 10 and 100° C. Iodotrimethylsilane in dichloromethane is a variant to achieve this transformation aprotically.

A trimethylsilyl group is cleaved, for example, in water, an aqueous solvent mixture or an alcohol, such as methanol or ethanol, in the presence of a base such as lithium hydroxide, sodium hydroxide, potassium carbonate, or sodium methoxide. Acids such as e.g. hydrochloric acid, trifluoroacetic acid, or acetic acid may also be suitable. The cleavage usually takes place at comparatively low temperatures, e.g. between −60 and 60° 0. Silyl groups other than trimethylsilyl are preferentially cleaved in the presence of an acid, e.g. trifluoroacetic acid, hydrochloric acid, or sulfuric acid, at temperatures between 0 and 100° C. A particularly suited cleaving method for silyl groups is based on the use of fluoride salts, e.g. tetrabutylammonium fluoride, hydrogen fluoride, or potassium fluoride, in organic solvents, such as for example diethyl ether, tetrahydrofuran, 1,4-dioxane, 1,2-dimethoxyethane, toluene, benzene, 1,2-dichloroethane, or dichloromethane at temperatures between −20 and 100° C.

A benzyl, methoxybenzyl, or benzyloxycarbonyl group is advantageously cleaved hydrogenolytically, e.g. with hydrogen in the presence of a catalyst such as palladium on carbon or palladium hydroxide, in a solvent such as methanol, ethanol, ethyl acetate, acetic acid or mixtures thereof optionally in the presence of an acid such as hydrochloric acid at temperatures between 0 and 100° C., preferably between 20 and 60° C., and at hydrogen pressures of 1 to 10 bar, preferably 3 to 5 bar. Trimethylsilyl iodide, boron trichloride, or boron trifluoride in the presence of a scavenger such as anisol, thioanisol, or pentamethylbenzene may also be used with benzylether derivatives. An electron-rich benzyl residue such as methoxybenzyl may also be cleaved oxidatively with e.g. 2,3-dichloro-5,6-dicyano-1,4-benzoquinone (DDQ) or ceric ammonium nitrate (CAN) preferably in an alcoholic or aqueous solvent at temperatures between 10 and 120° C. A 2,4-dimethoxybenzyl group is preferably cleaved in trifluoroacetic acid in the presence of a scavenger such as anisole.

A tert-butyl or tert-butyloxycarbonyl group is preferably cleaved by treating with an acid such as trifluoroacetic acid, sulfuric acid, or hydrochloric acid or by treating with iodotrimethylsilane optionally using a solvent such as methylene chloride, 1,4-dioxane, methanol, isopropanol, water, or diethylether.

A methyl group at an tertiary amine may be cleaved by the treatment with 1-chloroethyl chloroformate or vinyl chloroformate. Hydrobromic acid and boron tribromide are particularly suited for the cleavage of methylethers.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se (cf. Allinger N. L. and Eliel E. L. in "Topics in Stereochemistry", Vol. 6, Wiley Interscience, 1971) into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

The compounds of formula I may be converted into salts, particularly for pharmaceutical use into the pharmaceutically acceptable salts, with inorganic or organic acids, provided that compound I bears a basic residue. Acids which may be used for this purpose include for example hydrochloric acid, hydrobromic acid, sulfuric acid, methanesulfonic acid, phosphoric acid, fumaric acid, succinic acid, lactic acid, citric acid, tartaric acid, or maleic acid.

If the compounds of formula I contain an acidic residue such as a carboxy group, they may be converted into the salts thereof with inorganic or organic bases, particularly for pharmaceutical use into the pharmaceutically acceptable salts thereof. Suitable bases for this purpose include, for example, sodium hydroxide, potassium hydroxide, calcium hydroxide, calcium isopropoxide, magnesium hydroxide, magnesium ethoxide, ammonium hydroxide, cyclohexylamine, ethanolamine, diethanolamine, triethanolamine, N-methyl-D-glucamine, L-lysine, L-arginine, and piperazine.

The compounds according to the invention are advantageously also obtainable using the methods described in the examples that follow, which may also be combined for this purpose with methods known to the skilled man from the literature.

As already mentioned, the compounds of general formula I according to the invention and the pharmaceutically acceptable salts thereof have valuable pharmacological properties, particularly an inhibitory effect on the enzyme 11β-hydroxysteroid dehydrogenase (HSD) 1.

The biological properties of the new compounds may be investigated as follows:

Biological Test Example 1:

In vitro inhibition of 11β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 µM) and cortisone (80 nM). Cortisol generated in the reaction was then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition (% CTL) of each compound was determined relative to the carbenoxolone signal and $IC_{50}$ curves were generated.

The compounds of general formula I according to the invention tested according to this procedure have, for example, $IC_{50}$ values below 10000 nM, particularly below 1000 nM, most preferably below 200 nM.

TABLE 2

Inhibitory activity on 11β-HSD 1 of determined according to biological test example 1

| Example | IC$_{50}$ [nM] |
|---|---|
| 1 | 56 |
| 2 | 68 |
| 3 | 39 |
| 4 | 53 |
| 5 | 31 |
| 6 | 21 |
| 7 | 41 |
| 8 | 182 |
| 9 | 68 |
| 10 | 61 |
| 11 | 94 |
| 12 | 92 |
| 13 | 46 |
| 14 | 48 |
| 15 | 27 |
| 16 | 29 |
| 17 | 81 |
| 18 | 64 |
| 19 | 35 |
| 20 | 73 |
| 21 | 52 |
| 22 | 86 |
| 23 | 115 |
| 24 | 53 |
| 25 | 84 |
| 42 | 56 |
| 43 | 67 |
| 44 | 181 |
| 45 | 186 |
| 46 | 56 |
| 47 | 65 |
| 48 | 47 |
| 50 | 73 |
| 51 | 80 |
| 52 | 42 |
| 53 | 43 |
| 54 | 30 |
| 55 | 87 |
| 56 | 59 |
| 57 | 29 |

Biological Test Example 2:

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at room temperature in 96 well clear flexible PET Microbeta plates (PerkinElmer). The assay begins by dispensing 49 µl of substrate solution [50 mM HEPES, pH 7.4, 100 mM KCl, 5 mM NaCl, 2 mM MgCl$_2$, 2 mM NADPH and 160 nM [$^3$H]cortisone (1 Ci/mmol)] and mixing in 1 µL of the test compounds in dimethyl sulfoxide previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at room temperature. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates were shaken for 120 minutes at room temperature, and the SPA signal corresponding to [$^3$H]cortisol was measured on a Microbeta plate reader.

The compounds of general formula I according to the invention tested according to this procedure have, for example, IC$_{50}$ values below 1000 nM, particularly below 100 nM, most preferably below 10 nM.

TABLE 3

Inhibitory activity on 11β-HSD 1 of Examples compiled according to biological test example 2

| Example | IC$_{50}$ [nM] |
|---|---|
| 26 | 5.2 |
| 27 | 27.4 |
| 28 | 8.4 |
| 29 | 9.8 |
| 30 | 3.2 |
| 31 | 0.9 |
| 32 | 0.7 |
| 33 | 0.8 |
| 34 | 1.0 |
| 35 | 2.8 |
| 36 | 0.8 |
| 37 | 0.5 |
| 38 | 2.3 |
| 39 | 3.7 |
| 40 | 1.1 |
| 41 | 2.3 |
| 49 | 1.5 |
| 58 | 4.3 |
| 59 | 6.5 |
| — | — |
| — | — |

In view of their ability to inhibit the enzyme 11β-hydroxysteroid dehydrogenase (HSD) 1, the compounds of general formula I according to the invention and the corresponding pharmaceutically acceptable salts thereof are theoretically suitable for the treatment and/or preventative treatment of all those conditions or diseases which may be affected by the inhibition of the 11β-hydroxysteroid dehydrogenase (HSD) 1 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies, slow or poor wound healing), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyper-uricaemia. These substances may also be suitable for preventing beta-cell degeneration such as e.g. apoptosis or necrosis of pancreatic beta-cells. The substances may also be suitable for improving or restoring the functionality of pancreatic cells, and also of increasing the number and size of pancreatic beta-cells. The compounds according to the invention may also be used as diuretics or antihypertensives and may be suitable for the prevention and treatment of acute renal failure.

Additionally, inhibition of 11β-hydroxysteroid dehydrogenase (HSD) 1 has been shown to lower intraocular pressure in subjects with ocular hypertension, therefore the compounds could be used to treat glaucoma.

In view of the role of 11β-hydroxysteroid dehydrogenase (HSD) 1 in modulating cortisol levels for interaction with the glucocorticoid receptor and the known role of excess glucocorticoids in bone loss, the compounds may have beneficial effects against osteoporosis.

Stress and/or glucocorticoids have been shown to influence cognitive function, and excess cortisol has been associated with brain neuronal loss or dysfunction. Treatment with an 11β-hydroxysteroid dehydrogenase (HSD) 1 inhibitor may result in amelioration or prevention of cognitive impairment. Such compounds may also be useful in treating anxiety, depression, Alzheimer's disease, dementia, cognitive decline (including age-related cognitive decline).

The dynamic interaction between the immune system and the HPA (hypothalamopituitary-adrenal) axis is known, and glucocorticoids help balance between cell-mediated responses and humoral responses. The immune reaction is typically biased towards a humoral response in certain disease states, such as tuberculosis, leprosy, and psoriasis. More appropriate would be a cell-based response. An 11β-hydroxysteroid dehydrogenase (HSD) 1 inhibitor would bolster a temporal immune response in association with immunization to ensure that a cell based response would be obtained, and as such could be useful in immunomodulation.

In particular, the compounds according to the invention, including the pharmaceutically acceptable salts thereof, are suitable for the prevention or treatment of diabetes, particularly type 1 and type 2 diabetes mellitus, and/or diabetic complications.

The compounds of the invention are useful for symptoms of metabolic syndrome, glucose intolerance, hyperglycemica, hyperlipidemia, cardiovascular disease, lipodystrophy, Cushing's syndrome, Addison's Disease, visceral fat obesity associated with glucocorticoid therapy, polycystic ovarian syndrome, infertility and hypergonadism. The compounds of the invention can be used as therapeutic agents for pseudo Cushing's Syndrome associated with alcoholic liver disease. Additional diseases or disorders that can be treated with the disclosed compound include lipid disorders such as hypertriglyceridemia, hypercholesterolemia, low HDL levels and high LDL levels; vascular restenosis, pancreatitis, neurodegenerative disease, stroke, peripheral vascular disease, hyperinsulinemia, viral diseases, and Syndrome X.

The dosage required to achieve the corresponding activity for treatment or prevention (i.e., "effective amount") usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include, for example, those which potentiate the therapeutic effect of an 11β-hydroxysteroid dehydrogenase (HSD) 1 antagonist according to the invention with respect to one of the indications mentioned and/or which allow the dosage of an 11β-hydroxysteroid dehydrogenase (HSD) 1 antagonist according to the invention to be reduced. Therapeutic agents which are suitable for such a combination include, for example, antidiabetic agents such as metformin, sulfonylureas (e.g. glibenclamide, tolbutamide, glimepiride), nateglinide, repaglinide, thiazolidinediones (e.g. rosiglitazone, pioglitazone), SGLT 2 inhibitors (e.g. dapagliflozin, remogliflozin etabonate, sergliflozin, canagliflozin), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. Sitagliptin, Vildagliptin, Saxagliptin, Alogliptin, Linagliptin), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase and glucokinase activators, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, SDRIs, axokine, leptin, leptin mimetics, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a pharmaceutically acceptable salt of such a compound combined with at least one of the active substances described above as a combination partner, for preparing a pharmaceutical composition which is suitable for the treatment or prevention of diseases or conditions which can be affected by inhibiting the enzyme 11β-hydroxysteroid dehydrogenase (HSD) 1. These are preferably metabolic diseases, particularly one of the diseases or conditions listed above, most particularly diabetes or diabetic complications.

The use of the compound according to the invention, or a pharmaceutically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a pharmaceutically acceptable salt of such a compound and at least one of the active substances described above as combination partners, optionally together with one or more inert carriers and/or diluents.

Thus, for example, a pharmaceutical composition according to the invention comprises a combination of a compound of formula I according to the invention or a pharmaceutically acceptable salt of such a compound and at least one angiotensin II receptor antagonist optionally together with one or more inert carriers and/or diluents.

The compound according to the invention, or a pharmaceutically acceptable salt thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

Analytical HPLC-MS parameters employed for characterization of products:

| method 1 | Waters Xbridge C18, | | | method 2 | Waters Xbridge C18, | | |
|---|---|---|---|---|---|---|---|
| column | 30 × 4.6 mm, 2.5 μm | | | column | 30 × 4.6 mm, 2.5 μm | | |
| mobile | A: water + 0.1% NH$_3$ | | | mobile | A: water + 0.1% NH$_3$ | | |
| phase | B: methanol | | | phase | B: methanol | | |
| | time (min) | A % | B % | | time (min) | A % | B % |
| | 0.00 | 90 | 10 | | 0 | 90 | 10 |
| | 0.08 | 90 | 10 | | 0.15 | 90 | 10 |
| | 2.10 | 0 | 100 | | 4.00 | 0 | 100 |
| | 2.50 | 0 | 100 | | 4.40 | 0 | 100 |
| | 2.60 | 90 | 10 | | 4.55 | 90 | 10 |
| | 2.85 | 90 | 10 | | 5.00 | 90 | 10 |
| flow rate | 2.8 mL/min | | | flow rate | 1.6 mL/min | | |
| wavelength | UV 220, 230, or 254 nm | | | wavelength | UV 220, 230, or 254 nm | | |
| method 3 | Merck Cromolith Speed ROD, | | | method 4 | YMC-PACK ODS-AQ, 50 × 2.0 | | |
| column | RP18e, 50 × 4.6 mm | | | column | mm, 5 μm, 50° C. | | |
| mobile | A: water + 0.1% HCO$_2$H | | | mobile | A: H$_2$O (4 l) + F$_3$CCO$_2$H (1.5 l) | | |
| phase | B: acetonitrile + 0.1% HCO$_2$H | | | phase | B: MeCN (4 l) + F$_3$CCO$_2$H (0.75 l) | | |
| | time (min) | A % | B % | | time (min) | A % | B % |
| | 0.00 | 90 | 10 | | 0.00 | 90 | 10 |
| | 4.50 | 10 | 90 | | 2.2 | 20 | 80 |
| | 5.00 | 10 | 90 | | 2.5 | 20 | 80 |
| | 5.50 | 90 | 10 | | | | |
| flow rate | 1.5 mL/min | | | flow rate | 1.0 mL/min | | |
| wavelength | UV 220, 230, or 254 nm | | | wavelength | UV 220 nm | | |
| | method 5 | Merck Cromolith SpeedROD, | | | | | |
| | column | RP18e, 50 × 4.6 mm | | | | | |
| | mobile | A: 0.01% F$_3$CCO$_2$H/water, | | | | | |
| | phase | B: 0.01% F$_3$CCO$_2$H/CH$_3$CN | | | | | |
| | time (min) | A % | B % | | | | |
| | 0.0 | 90 | 10 | | | | |
| | 2.0 | 10 | 90 | | | | |
| | 2.4 | 10 | 90 | | | | |
| | 2.5 | 90 | 10 | | | | |
| | 3.0 | 90 | 10 | | | | |
| | flow rate | 1.0 mL/min | | | | | |

INTERMEDIATE 1

3-(4-Bromo-phenyl)-oxetan-3-ol

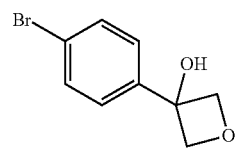

n-Butyllithium (1.6 mol/L in hexanes, 1.33 mL) was added to a solution of 1,4-dibromobenzene (0.50 g) in tetrahydrofuran (5 mL) cooled to −78° C. The solution was stirred at this temperature for 30 min prior to the dropwise addition of 3-oxetanone (0.15 g) dissolved in tetrahydrofuran (2 mL). The solution was warmed in the cooling bath to room temperature overnight. Aqueous NH$_4$Cl solution was then added and the resulting mixture was extracted with ethyl acetate. The combined extracts were dried (Na$_2$SO$_4$) and the solvent was evaporated. The residue was purified by HPLC on reversed phase (acetonitrile/water) to give the title compound. Yield: 0.19 g (39% of theory); Mass spectrum (ESI$^−$): m/z=273/275 (Br) [M+HCOO]$^−$.

INTERMEDIATE 2

1-(5-Bromo-pyridin-2-yl-cyclopropanecarbonitrile

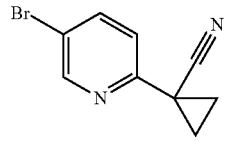 [SMILES: N#CC1(c2ccc(Br)cn2)CC1]

Potassium hexamethyldisilazide (0.5 mol/L in toluene, 34 mL) was added over a period of 5 min to a solution of 5-bromo-2-fluoro-pyridine (1.50 g) and cyclopropanecarbonitrile (0.63 mL) in toluene (2 mL) chilled in an ice bath. Aqueous NH$_4$Cl solution was then added and the resulting mixture was extracted with ethyl acetate. The combined extracts were dried (Na$_2$SO$_4$) and the solvent was evaporated. The residue was chromatographed on silica gel (cyclohexane/ethyl acetate 1:0→8:2) to give the title compound as a colorless solid. Yield: 0.19 g (10% of theory); LC (method 2): t$_R$=3.34 min; Mass spectrum (ESI$^+$): m/z=223/225 (Br) [M+H]$^+$.

Alternatively, the title compound was prepared from (5-bromo-pyridin-2-yl)-acetonitrile and 1,2-dibromoethane following a procedure analogous to that described in Step 3 for Intermediate 4. Yield: 88% of theory.

INTERMEDIATE 3

1-(5-Bromo-pyridin-2-yl)-cyclopropanecarboxylic acid amide

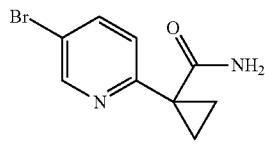 [SMILES: NC(=O)C1(c2ccc(Br)cn2)CC1]

A mixture of 1-(5-bromo-pyridin-2-yl)-cyclopropanecarbonitrile (0.18 g) and sulfuric acid (95%, 1.8 mL) was stirred at room temperature overnight. The solution was poured on crushed ice and the resulting solution was basified using 4 M aqueous NaOH solution. The solution was extracted with dichloromethane, the combined extracts were dried (Na$_2$SO$_4$), and the solvent was evaporated to give the title compound as a colorless solid. Yield: 0.20 g (quantitative); LC (method 2): t$_R$=2.38 min; Mass spectrum (ESI$^+$): m/z=241/243 (Br) [M+H]$^+$.

INTERMEDIATE 4

1-(6-Chloro-pyridazin-3-yl)-cyclopropanecarbonitrile

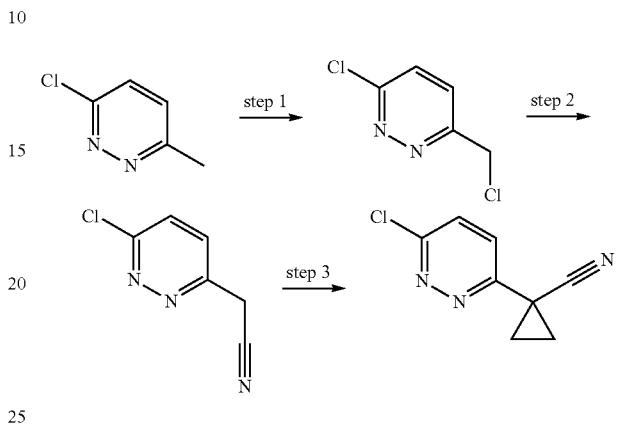

Step 1: 3-chloro-6-chloromethyl-pyridazine

Trichloroisocyanuric acid (3.62 g) was added to a solution of 3-chloro-6-methyl-pyridazine (5.00 g) in chloroform (130 mL) heated to 60° C. The mixture was stirred at 60° C. for 2 h and then at room temperature overnight. The mixture was filtered over Celite and the filtrate was concentrated. The residue was chromatographed on silica gel (cyclohexane/ethyl acetate 98:2→70:30) to give the title compound as a colorless oil that solidified on standing. Yield: 2.48 g (39% of theory); Mass spectrum (ESI$^+$): m/z=163/165/167 (2 Cl) [M+H]$^+$.

Step 2: (6-chloro-pyridazin-3-yl)-acetonitrile

3-Chloro-6-chloromethyl-pyridazine (1.50 g) dissolved in dimethyl sulfoxide (7.5 mL) was added to a solution of potassium cyanide (0.90 g) in water (1 mL) and dimethyl sulfoxide (7.5 mL) stirred at 80° C. The solution was stirred at this temperature for 30 min and then cooled to room temperature. Water and ethyl acetate were added and the resulting mixture was filtered over Celite. The aqueous phase of the filtrate was separated and extracted twice with ethyl acetate. The extracts and the organic phase of the filtrate were combined and washed with brine and dried (Na$_2$SO$_4$). The solvent was evaporated and the residue was chromatographed on silica gel (cyclohexane/ethyl acetate 1:1→0:1) to give the title compound as a solid. Yield: 0.23 g (16% of theory); LC (method 2): t$_R$=0.76 min; Mass spectrum (ESI$^+$): m/z=154/156 (Cl) [M+H]$^+$.

Step 3: 1-(6-chloro-pyridazin-3-yl)-cyclopropanecarbonitrile

Aqueous NaOH solution (50%, 5 mL) was added to a solution of (6-chloro-pyridazin-3-yl)-acetonitrile (0.21 g), 1,2-dibromoethane (0.14 mL), and benzyltributylammonium chloride (0.43 g) in acetonitrile (5 mL) at room temperature. The resulting mixture was stirred at room temperature for 4 h and was then extracted with ethyl acetate. The combined extracts were washed with brine and dried (MgSO$_4$). The solvent was evaporated and the residue was chromatographed on silica gel (cyclohexane/ethyl acetate 1:1→0:1) to give the title compound as a solid. Yield: 0.14 g (57% of theory); LC (method 1): $t_R$=1.12 min; Mass spectrum (ESI$^+$): m/z=180/182 (Cl) [M+H]$^+$.

INTERMEDIATE 5

1-(5-Bromo-pyridin-2-yl)-cyclopropanecarboxylic acid methylamide

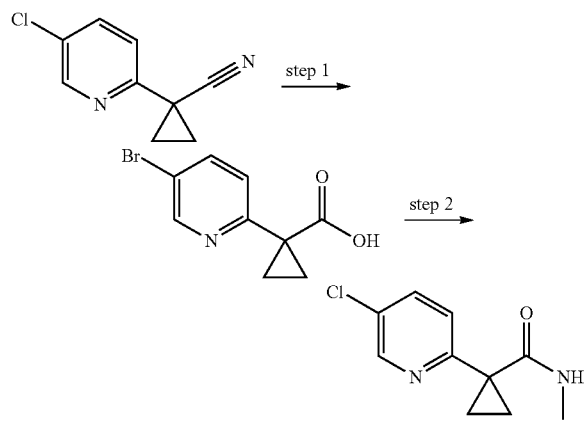

Step 1:
1-(5-bromo-pyridin-2-yl)-cyclopropanecarboxylic acid

A flask charged with a stir bar, 1-(5-bromo-pyridin-2-yl)-cyclopropanecarbonitrile (1.00 g), 25% aqueous NaOH solution (1 mL), and ethanol (10 mL) was heated to 100° C., and the mixture was stirred at this temperature for 14 h. After cooling to room temperature, the solution was poured into ice-cold saturated aqueous Na$_2$HPO$_4$ solution and the resulting mixture was adjusted to pH 4 by the addition of 1 M aqueous hydrochloric acid. The mixture was extracted with ethyl acetate and the combined extracts were washed with brine and dried (MgSO$_4$). The solvent was evaporated and the residue was recrystallized from diisopropyl ether to give the title compound as a yellowish solid. Yield: 0.58 g (53% of theory); LC (method 1): $t_R$=0.60 min; Mass spectrum (ESI$^+$): m/z=242/244 (Br) [M+H]$^+$.

Step 2:
1-(5-bromo-pyridin-2-yl)-cyclopropanecarboxylic acid methylamide 2-(1H-Benzotriazol-1-yl)-1,1,3,3-tetramethyluronium tetrafluoroborate (0.13 g; alternatively, 2-(7-aza-1H-benzotriazol-1-yl)-1,1,3,3-tetramethyluronium hexafluorophosphate may be used) was added to a solution of 1-(5-bromo-pyridin-2-yl)-cyclopropanecarboxylic acid (0.10 g) and ethyl-diisopropyl-amine (70 μL) in N,N-dimethylformamide (1 mL) at room temperature. The solution was stirred for 20 min prior to the addition of methylamine (2 mol/L in tetrahydrofuran, 0.62 mL). The resulting solution was stirred at room temperature for 1 h and then concentrated. The residue was purified by HPLC on reversed phase (0.125% aqueous ammonia/methanol) to afford the title compound. Yield: 0.10 g (95% of theory); LC (method 1): $t_R$=1.44 min; Mass spectrum (ESI$^+$): m/z=255/257 (Br) [M+H]$^+$.

INTERMEDIATE 6

1-(5-Bromo-pyridin-2-yl)-cyclopropanecarboxylic acid dimethylamide

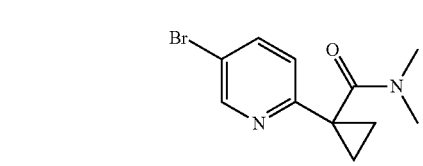

The title compound was prepared from 1-(5-bromo-pyridin-2-yl)-cyclopropanecarboxylic acid and dimethylamine (2 mol/L in tetrahydrofuran) following a procedure analogous to that described in Step 2 for Intermediate 5. Yield: quantitative; LC (method 1): $t_R$=1.65 min; Mass spectrum (ESI$^+$): m/z=269/271 (Br) [M+H]$^+$.

INTERMEDIATE 7

1-(6-Chloro-pyridazin-3-yl)-cyclopropanecarboxylic acid ethyl ester

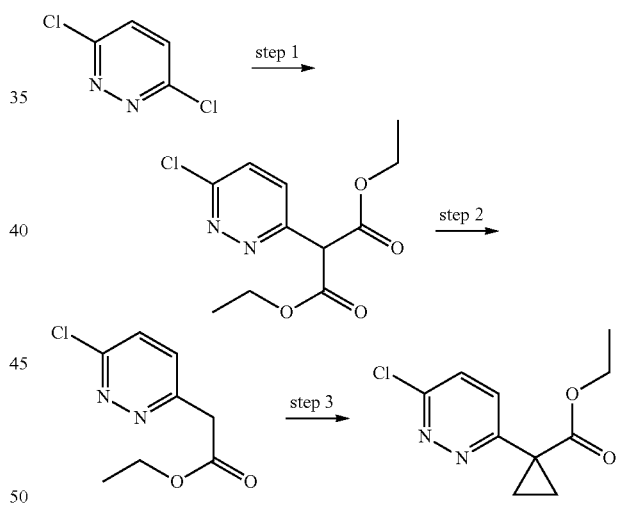

Step 1: 2-(6-chloro-pyridazin-3-yl)-malonic acid diethyl ester

Cesium carbonate (43.7 g) was added to a solution of 3,6-dichloropyridazine (10.0 g) and malonic acid diethyl ester (15.2 mL) in dimethyl sulfoxide (20 mL) at room temperature. The mixture was stirred at 110° C. for 1 h and then cooled to room temperature. Water and ethyl acetate were added and the resulting mixture was filtered over Celite. The aqueous phase of the filtrate was separated and extracted twice with ethyl acetate. The extracts and the organic phase of the filtrate were combined and washed with water and brine. Silica gel (50 g) and charcoal (5 g) were then added and the resulting mixture was stirred for 30 min at room temperature. The silica gel and charcoal were separated by filtration and the filtrate was concentrated to give the crude title compound that was used without further purification. Yield: 19.0 g (ca. 65% pure); LC (method 1): $t_R$=1.25 min; Mass spectrum (ESI$^+$): m/z=273/275 (Cl) [M+H]$^+$.

Step 2: (6-chloro-pyridazin-3-yl)-acetic acid ethyl ester

A mixture of 2-(6-chloro-pyridazin-3-yl)-malonic acid diethyl ester (from step 1, ca. 65%, 19.0 g), sodium chloride (11.8 g), water (1.3 mL), and dimethyl sulfoxide (80 mL) was stirred at 150° C. for 4.5 h. More sodium chloride (5.0 g) and water (0.6 mL) were then added and stirring was continued at 160° C. for another 2 h. After cooling to room temperature, water was added and the resulting mixture was extracted with tert-butyl methyl ether. The combined extracts were washed with water and brine and dried (MgSO$_4$). The solvent was evaporated to give the crude title compound that was submitted to the next reaction step without further purification. Yield: 9.0 g (64% of theory); LC (method 1): $t_R$=1.18 min.

Step 3: 1-(6-chloro-pyridazin-3-yl)-cyclopropanecarboxylic acid ethyl ester

The title compound was prepared from (6-chloro-pyridazin-3-yl)-acetic acid ethyl ester and 1,2-dibromoethane following a procedure analogous to that described in Step 3 for Intermediate 4. Yield: 20% of theory; LC (method 1): $t_R$=1.45 min; Mass spectrum (ESI$^+$): m/z=227/228 (Cl) [M+H]$^+$.

INTERMEDIATE 8

4-Bromo-1-[(S)-tetrahydro-furan-3-yl]-1H-pyridin-2-one

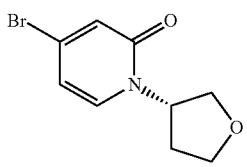

A mixture of 4-bromo-1H-pyridin-2-one (0.50 g), (R)-toluene-4-sulfonic acid tetrahydrofuran-3-yl ester (0.40 g), potassium carbonate (0.80 g), and dimethylsulfoxide (5 mL) was stirred at 80° C. overnight. After cooling to ambient temperature, water was added and the resulting mixture was extracted with ethyl acetate. The combined organic extracts were washed with brine, dried (MgSO$_4$), and concentrated. The residue was purified by HPLC on reversed phase (acetonitrile/water) to afford the title compound [besides, 4-bromo-2-[(S)-tetrahydro-furan-3-yloxy]-pyridine was isolated in 0.36 g (56% of theory)]. Yield: 0.11 g (16% of theory); LC (method 3): $t_R$=2.18 min; Mass spectrum (ESI$^+$): m/z=244/246 (Br) [M+H]$^+$.

INTERMEDIATE 9

4-Bromo-1-[(R)-tetrahydro-furan-3-yl]-1H-pyridin-2-one

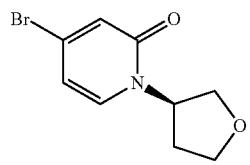 [SMILES: O=c1cc(Br)ccn1[C@@H]1CCOC1]

The title compound was prepared from 4-bromo-1H-pyridin-2-one and (S)-toluene-4-sulfonic acid tetrahydrofuran-3-yl ester following a procedure analogous to that described for Intermediate 8. Yield: 18% of theory; LC (method 3): $t_R$=2.18 min; Mass spectrum (ESI$^+$): m/z=244/246 (Br) [M+H]$^+$.

INTERMEDIATE 10

4-Bromo-1-(tetrahydro-pyran-4-yl)-1H-pyrazole

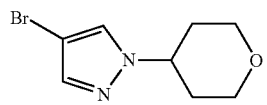

A mixture of 4-bromo-triazole (0.30 g), toluene-4-sulfonic acid tetrahydro-pyran-4-yl ester (0.52 g), cesium carbonate (1.00 g), and N,N-dimethylformamide (7 mL) was stirred at 60° C. overnight. After cooling to ambient temperature, water was added and the resulting mixture was extracted with ethyl acetate. The combined organic extracts were washed with brine, dried (MgSO$_4$), and concentrated. The residue was triturated with cyclohexane/diethyl ether to afford the title compound as a colorless solid. Yield: 0.26 g (55% of theory); LC (method 3): $t_R$=2.75 min; Mass spectrum (ESI$^+$): m/z=231/233 (Br) [M+H]$^+$.

INTERMEDIATE 11

4-Bromo-1-[(R)-tetrahydro-furan-3-yl]-1H-pyrazole

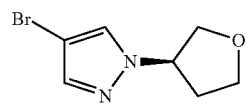

The title compound was prepared from 4-bromo-triazole and (S)-toluene-4-sulfonic acid tetrahydro-furan-3-yl ester following a procedure analogous to that described for Intermediate 10, except for purifying the product by chromatography on silica gel (cyclohexane/ethyl acetate 9:1→1:1).

Yield: 26% of theory; LC (method 3): $t_R$=2.54 min; Mass spectrum (ESI⁺): m/z=217/219 (Br) [M+H]⁺.

INTERMEDIATE 12

4-Bromo-1-[(S)-tetrahydro-furan-3-yl]-1H-pyrazole

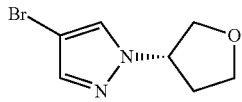

The title compound was prepared from 4-bromo-triazole and (R)-toluene-4-sulfonic acid tetrahydro-furan-3-yl ester following a procedure analogous to that described for Intermediate 10, except for purifying the product by chromatography on silica gel (cyclohexane/ethyl acetate 9:1→1:1). Yield: 74% of theory; LC (method 3): $t_R$=2.54 min; Mass spectrum (ESI⁺): m/z=217/219 (Br) [M+H]⁺.

INTERMEDIATE 13

1-(6-Chloro-pyridin-3-yl)-cyclopropanecarbonitrile

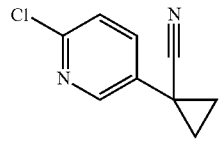 [SMILES: N#CC1(c2ccc(Cl)nc2)CC1]

The title compound was prepared from (6-chloro-pyridin-3-yl)-acetonitrile and 1,2-dibromoethane following a procedure analogous to that described in Step 3 for Intermediate 4. Yield: 43% of theory; LC (method 3): $t_R$=2.71 min; Mass spectrum (ESI⁺): m/z=179/181 (Cl) [M+H]⁺.

INTERMEDIATE 14

5-Bromo-2-(1-methanesulfonyl-cyclopropyl)-pyridine

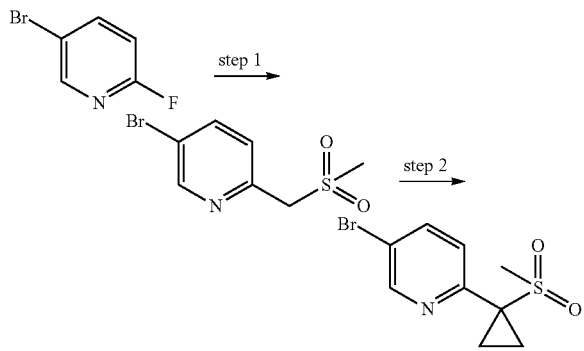

Step 1: 5-bromo-2-methanesulfonylmethyl-pyridine

5-Bromo-2-fluoro-pyridine (2.00 g) dissolved in tetrahydrofuran (20 mL) was added dropwise to a solution of sodium hexamethyldisilazide (2 mol/L in tetrahydrofuran, 28.5 mL) in tetrahydrofuran (20 mL) cooled to ca. −17° C. Dimethylsulfone (4.30 g) was added and stirring continued in the cooling bath for 1 h. The cooling bath was then removed and the solution was stirred at room temperature for one more h. Aqueous NH₄Cl solution and brine were added and the resulting mixture was extracted with ethyl acetate. The combined extracts were dried (MgSO₄) and the solvent was evaporated. The residue was treated with little ethyl acetate to precipitate the title compound. Yield: 1.73 g (63% of theory); LC (method 3): $t_R$=2.01 min; Mass spectrum (ESI⁺): m/z=250/252 (Br) [M+H]⁺.

Step 2: 5-bromo-2-(1-methanesulfonyl-cyclopropyl)-pyridine

The title compound was prepared from 5-bromo-2-methanesulfonylmethyl-pyridine and 1,2-dibromoethane following a procedure analogous to that described in Step 3 for Intermediate 4. Yield: 19% of theory; LC (method 3): $t_R$=2.52 min; Mass spectrum (ESI⁺): m/z=276/278 (Br) [M+H]⁺.

INTERMEDIATE 15

1-(6-Chloro-pyridin-3-yl)-cyclopropanecarboxylic acid amide

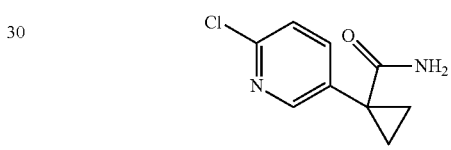

The title compound was prepared from 1-(6-chloro-pyridin-3-yl)-cyclopropanecarbonitrile following a procedure analogous to that described in Intermediate 3. Yield: 86% of theory; LC (method 3): $t_R$=1.93 min; Mass spectrum (ESI⁺): m/z=197/199 (Cl) [M+H]⁺.

INTERMEDIATE 16

2-Bromo-6-(1-methanesulfonyl-cyclopropyl)-pyridine

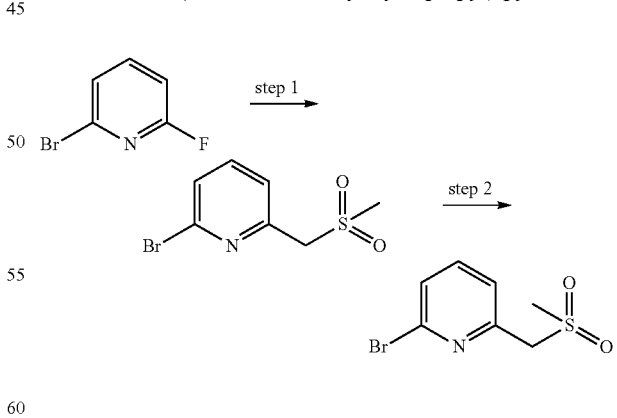

Step 1: 2-bromo-6-methanesulfonylmethyl-pyridine

The title compound was prepared from 2-bromo-6-fluoropyridine and dimethylsulfone following a procedure analogous to that described in Step 1 for Intermediate 14. Yield: ca. 70% of theory (crude); LC (method 3): $t_R$=1.98 min; Mass spectrum (ESI⁺): m/z=250/252 (Br) [M+H]⁺.

Step 2: 2-bromo-6-(1-methanesulfonyl-cyclopropyl)-pyridine

The title compound was prepared from 2-bromo-6-methanesulfonylmethyl-pyridine and 1,2-dibromoethane following a procedure analogous to that described in Step 3 for Intermediate 4. Yield: 53% of theory; LC (method 3): $t_R$=2.56 min; Mass spectrum (ESI$^+$): m/z=276/278 (Br) [M+H]$^+$.

INTERMEDIATE 17

4-Bromo-2-(1-methanesulfonyl-cyclopropyl)-pyridine

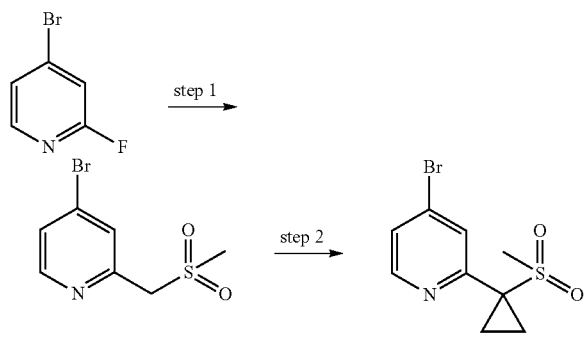

Step 1: 4-bromo-2-methanesulfonylmethyl-pyridine

The title compound was prepared from 4-bromo-2-fluoropyridine and dimethylsulfone following a procedure analogous to that described in Step 1 for Intermediate 14. Yield: ca. 91% of theory (crude); LC (method 3): $t_R$=2.01 min; Mass spectrum (ESI$^+$): m/z=250/252 (Br) [M+H]$^+$.

Step 2: 4-bromo-2-(1-methanesulfonyl-cyclopropyl)-pyridine

The title compound was prepared from 4-bromo-2-methanesulfonylmethyl-pyridine and 1,2-dibromoethane following a procedure analogous to that described in Step 3 for Intermediate 4. Yield: 20% of theory; Mass spectrum (ESI$^+$): m/z=276/278 (Br) [M+H]$^+$.

INTERMEDIATE 18

1-(6-Bromo-pyridin-2-yl)-cyclopropanecarboxylic acid amide

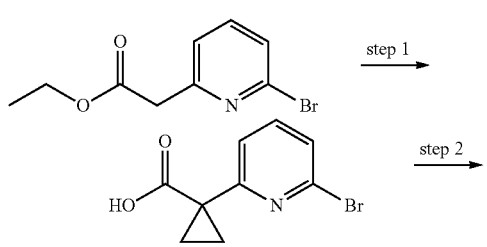

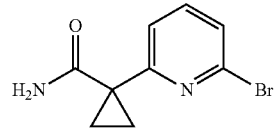

Step 1: 1-(6-bromo-pyridin-2-yl)-cyclopropanecarboxylic acid

The title compound was prepared from (6-bromo-pyridin-2-yl)-acetic acid ethyl ester and 1,2-dibromoethane following a procedure analogous to that described in Step 3 for Intermediate 4; under these conditions the ester group was hydrolyzed. Yield: 57% of theory; LC (method 3): $t_R$=2.60 min; Mass spectrum (ESI$^+$): m/z=242/244 (Br) [M+H]$^+$.

Step 2: 4-bromo-2-(1-methanesulfonyl-cyclopropyl)-pyridine

The title compound was prepared from 1-(6-bromo-pyridin-2-yl)-cyclopropanecarboxylic acid and ammonia (32% in water) following a procedure analogous to that described in Step 2 for Intermediate 5. Yield: 65% of theory; LC (method 3): $t_R$=2.05 min; Mass spectrum (ESI$^+$): m/z=241/243 (Br) [M+H]$^+$.

INTERMEDIATE 19

1-(6-Bromo-pyridin-2-yl)-cyclopropanecarboxylic acid methylamide

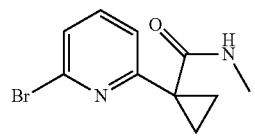

The title compound was prepared from 1-(6-bromo-pyridin-2-yl)-cyclopropanecarboxylic acid and methylamine (2 mol/L in tetrahydrofuran) following a procedure analogous to that described in Step 2 for Intermediate 5. Yield: 70% of theory; LC (method 3): $t_R$=2.27 min; Mass spectrum (ESI$^+$): m/z=255/257 (Br) [M+H]$^+$.

INTERMEDIATE 20

1-(6-Bromo-pyridin-2-yl)-cyclopropanecarboxylic acid dimethylamide

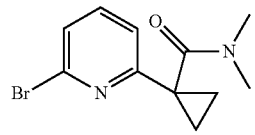

The title compound was prepared from 1-(6-bromo-pyridin-2-yl)-cyclopropanecarboxylic acid and dimethylamine (2 mol/L in tetrahydrofuran) following a procedure analogous to that described in Step 2 for Intermediate 5. Yield: 70% of theory; LC (method 3): $t_R$=2.97 min; Mass spectrum (ESI$^+$): m/z=255/257 (Br) [M+H]$^+$.

INTERMEDIATE 21

2-Chloro-5-(1-methanesulfonyl-cyclopropyl)-pyridine

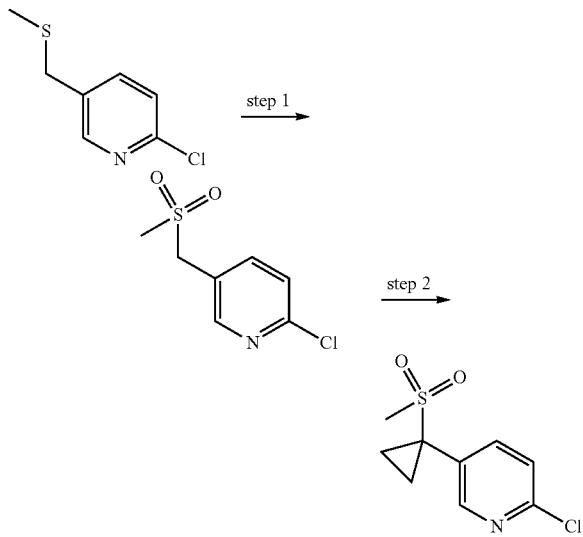

Step 1: 2-chloro-5-methanesulfonylmethyl-pyridine

3-Chloroperoxybenzoic acid (77%, 4.55 g) was added to a solution of 2-chloro-5-methylsulfanylmethyl-pyridine (1.53 g) in dichloromethane (60 mL) chilled in an ice bath. The cooling bath was removed and the solution was stirred at room temperature overnight. The solution was diluted with dichloromethane, washed with 10% aqueous $K_2CO_3$ solution and water, and dried (MgSO$_4$). The solvent was evaporated and the residue was chromatographed on silica gel (cyclohexane/ethyl acetate 3:7→0:1) to afford the title compound. Yield: 0.87 g (48% of theory); Mass spectrum (ESI$^+$): m/z=206/208 (Cl) [M+H]$^+$.

Step 2: 2-chloro-5-(1-methanesulfonyl-cyclopropyl)-pyridine

The title compound was prepared from 2-chloro-5-methanesulfonylmethyl-pyridine and 1,2-dibromoethane following a procedure analogous to that described in Step 3 for Intermediate 4. Yield: 52% of theory; Mass spectrum (ESI$^+$): m/z=232/234 (Cl) [M+H]$^+$.

INTERMEDIATE 22

4-Bromo-1-(oxetan-3-yl)pyridin-2(1H)-one

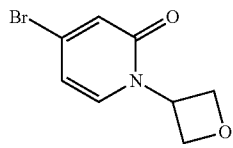 [SMILES: O=c1cc(Br)ccn1C1COC1]

A mixture of 4-bromopyridin-2(1H)-one (173 mg), 3-iodooxetane (184 mg), and $K_2CO_3$ (414 mg) in N,N-dimethylformamide (15 mL) was stirred at 100° C. for 2 h. The reaction mixture was stirred at room temperature for one more hour and then quenched with $H_2O$ (30 mL). The resulting mixture was extracted with ethyl acetate (3×20 mL) and the combined organic phase was dried (Na$_2$SO$_4$) and concentrated to give the crude product, which was purified by preparative TLC to give the title compound. Yield: 68 mg (30% of theory).

INTERMEDIATE 23 tert-Butyl 3-(4-bromo-2-oxopyridin-1 (2H)-yl)azetidine-1-carboxylate

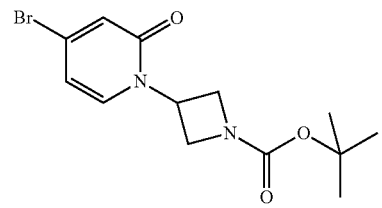 [SMILES: CC(C)(C)OC(=O)N1CC(n2ccc(Br)cc2=O)C1]

The title compound was prepared from 4-bromopyridin-2 (1H)-one and 3-iodo-azetidine-1-carboxylic acid tert-butyl ester following a procedure analogous to that described for Intermediate 22.

INTERMEDIATE 24

1-(5-Bromopyrimidin-2-yl)imidazolidin-2-one

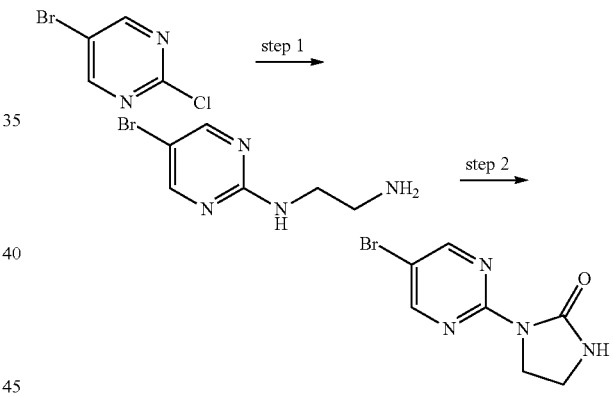

Step 1: N$^1$-(5-bromopyrimidin-2-yl)ethane-1,2-diamine

Ethane-1,2-diamine (200 mg) was added to a solution of 5-bromo-2-chloro-pyrimidine (500 mg) and triethylamine (1 mL) in ethanol (10 mL) at 0° C. The reaction mixture was stirred under nitrogen at room temperature overnight. The formed mixture was concentrated to give crude N$^1$-(5-bromopyrimidin-2-yl)ethane-1,2-diamine. Yield: 687 mg (100% of theory).

Step 2: 1-(5-bromopyrimidin-2-yl)imidazolidin-2-one

N$^1$-(5-Bromopyrimidin-2-yl)ethane-1,2-diamine (100 mg) was added to a solution of carbonyl diimidazole (30 mg) in tetrahydrofuran (5 mL) at 0° C. The reaction mixture was stirred under nitrogen at room temperature for 1 h. The formed solution was concentrated to give an oil, which was purified by preparative TLC to afford the title compound. Yield: 13 mg (12% of theory).

INTERMEDIATE 25

1-(5-bromopyrimidin-2-yl)-3-methylimidazolidin-2-one

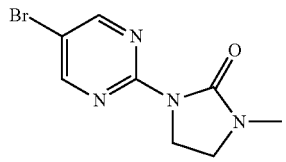

NaH (10 mg) was added to a solution of 1-(5-bromopyrimidin-2-yl)imidazolidin-2-one (50 mg) in N,N-dimethylformamide (5 mL) under nitrogen at 0° C. After stirring for 30 min, MeI (36 mg) was added. The reaction mixture was stirred at room temperature until the starting material was completely consumed (TLC). The reaction mixture was then quenched with $H_2O$ (20 mL) and the resulting mixture was extracted with ethyl acetate (3×20 mL). The combined extracts were washed with $H_2O$ (3×20 mL), dried ($Na_2SO_4$), and concentrated. The residue was purified by preparative TLC to afford the title compound. Yield: 10 mg (19% of theory).

INTERMEDIATE 26

1-(5-bromopyrimidin-2-yl)pyrrolidin-2-one

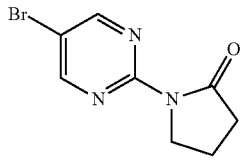 [SMILES: O=C1CCCN1c1ncc(Br)cn1]

A mixture of 5-bromo-2-chloropyrimidine (11.3 g), pyrrolidin-2-one (5 g), and $K_2CO_3$ (27.4 g) in 1-methylpyrrolidin-2-one (100 mL) was heated to 80° C. under nitrogen and stirred at this temperature overnight. After cooling to room temperature, the reaction mixture was concentrated to give an oil which was poured into water (50 mL). The resulting mixture was extracted with ethyl acetate (3×50 mL) and the combined organic phase was concentrated to afford an oil, which was purified by column chromatography on silica gel to afford the title compound. Yield: 592 mg (4% of theory).

INTERMEDIATE 27

3-(azetidin-1-yl)-6-chloropyridazine

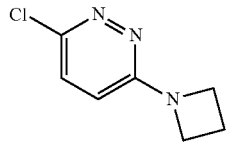 [SMILES: Clc1ccc(N2CCC2)nn1]

Azetidine (250 mg) was added to a stirred solution of 3,6-dichloropyridazine (650 mg) and N,N-diisopropyl-ethylamine (0.9 mL) in n-propanol (10 mL). The mixture was stirred at room temperature for 9 days and then concentrated. The solid residue was partitioned between ethyl acetate (100 mL) and water (10 mL). The organic layer was separated and washed with brine (10 mL), dried ($Na_2SO_4$), and concentrated to leave a white solid (627 mg). Chromatography on a 12-g silica gel cartridge (eluted with a 0-100% ethyl acetate in hexanes gradient) afforded the title compound as a white solid. Yield: 441 mg (59% of theory); $^1H$ NMR (CDCl$_3$) δ 2.47 (m, 2H), 4.13 (m, 4H), 6.48 (d, 1H), 7.16 (d, 1H).

INTERMEDIATE 28

5-bromo-2-(3-fluoroazetidin-1-yl)pyrimidine

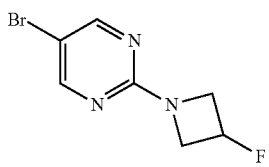 [SMILES: FC1CN(c2ncc(Br)cn2)C1]

The title compound was prepared following a procedure analogous to that described for Intermediate 27 using 5-bromo-2-chloropyrimidine and 3-fluoroazetidine hydrogen chloride salt. LC (method 5): $t_R$=1.33 min; Mass spectrum (ESI$^+$): m/z=232/234 (Br) [M+H]$^+$.

INTERMEDIATE 29

5-bromo-2-(3,3-difluoroazetidin-1-yl)pyrimidine

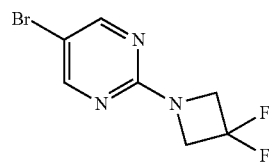 [SMILES: FC1(F)CN(c2ncc(Br)cn2)C1]

The title compound was prepared following a procedure analogous to that described for Intermediate 27 using 5-bromo-2-chloropyrimidine and 3,3-difluoroazetidine hydrogen chloride salt. LC (method 5): $t_R$=1.57 min; Mass spectrum (ESI$^+$): m/z=250/252 (Br) [M+H]$^+$.

INTERMEDIATE 30

1-(5-bromopyrimidin-2-yl)azetidin-3-ol

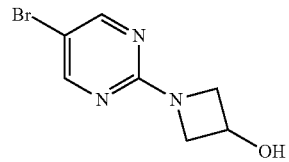 [SMILES: OC1CN(c2ncc(Br)cn2)C1]

The title compound was prepared following a procedure analogous to that described for Intermediate 27 using 5-bromo-2-chloropyrimidine and 3-hydroxyazetidine hydrogen chloride salt. Purification by preparative HPLC provided the compound as its trifluoroacetic acid salt. LC (method 5): $t_R$=0.95 min; Mass spectrum (ESI⁺): m/z=230/232 (Br) [M+H]⁺.

INTERMEDIATE 31

1-(5-Bromo-pyridin-2-yl)-cyclopentanecarboxylic acid amide

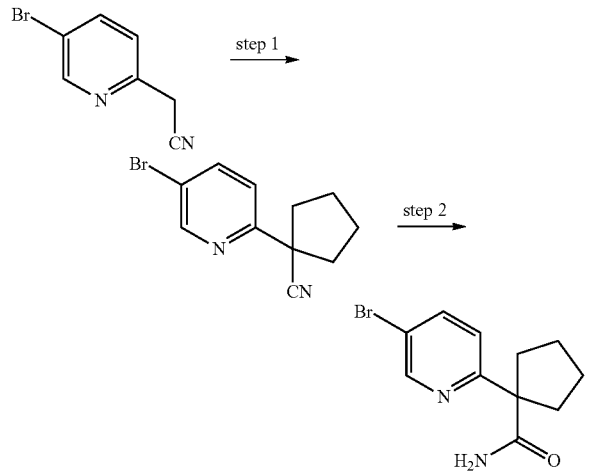

Step: 1:
1-(5-bromo-pyridin-2-yl)-cyclopentanecarbonitrile

The title compound was prepared from (5-bromo-pyridin-2-yl)-acetonitrile and 1,4-dibromobutane following a procedure analogous to that described in Step 3 for Intermediate 4. Yield: 78% of theory; Mass spectrum (ESI⁺): m/z=251/253 (Br) [M+H]⁺.

Step 2:
1-(5-bromo-pyridin-2-yl)-cyclopentanecarboxylic acid amide

The title compound was prepared from 1-(5-bromo-pyridin-2-yl)-cyclopentanecarbonitrile following a procedure analogous to that described in Intermediate 3. Yield: 93% of theory; LC (method 1): $t_R$=1.75 min; Mass spectrum (ESI⁺): m/z=269/271 (Br) [M+H]⁺.

INTERMEDIATE 32

1-(5-Bromo-pyridin-2-yl)-cyclohexanecarboxylic acid amide

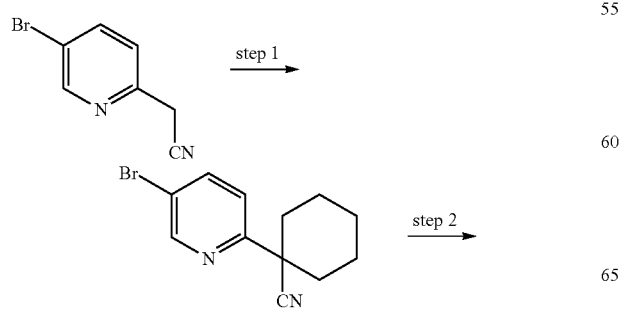

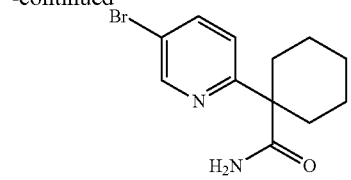

Step 1:
1-(5-bromo-pyridin-2-yl)-cyclohexanecarbonitrile

The title compound was prepared from (5-bromo-pyridin-2-yl)-acetonitrile and 1,5-dibromopentane following a procedure analogous to that described in Step 3 for Intermediate 4. Yield: 60% of theory; Mass spectrum (ESI⁺): m/z=265/267 (Br) [M+H]⁺.

Step 2:
1-(5-bromo-pyridin-2-yl)-cyclohexanecarboxylic acid amide

The title compound was prepared from 1-(5-bromo-pyridin-2-yl)-cyclohexanecarbonitrile following a procedure analogous to that described in Intermediate 3. Yield: 86% of theory; LC (method 1): $t_R$=1.89 min; Mass spectrum (ESI⁺): m/z=283/285 (Br) [M+H]⁺.

INTERMEDIATE 33

1-(4-Bromo-pyridin-2-yl)-cyclopropanecarboxylic acid ethyl ester

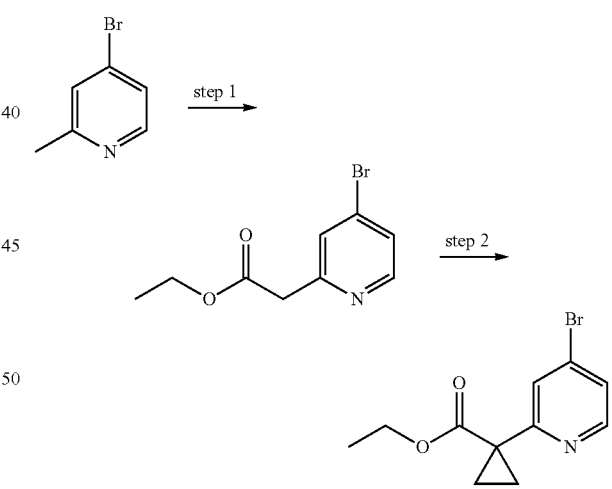

Step 1: (4-bromo-pyridin-2-yl)-acetic acid ethyl ester

Lithium diisopropylamide (2 mol/L in tetrahydrofuran/heptane/ethylbenzene, 3.00 mL) was added to a solution of 4-bromo-2-methylpyridine (2.00 g) and diethyl carbonate (1.8 mL) in tetrahydrofuran (30 mL) cooled to −70° C. The solution was stirred for 1 h prior to the addition of another portion of lithium diisopropylamide (2 mol/L in tetrahydrofuran/heptane/ethylbenzene, 3.00 mL). Stirring was continued at −70° C. for one more hour and then the reaction was quenched by the addition of water. The resulting mixture was extracted with ethyl acetate and the combined extracts were washed with brine and dried (Na$_2$SO$_4$). The solvent was evaporated and the residue was chromatographed on silica gel (cyclohexane/ethyl acetate 95:5→1:1) to give the title compound. Yield: 2.35 g (83% of theory); LC (method 3): t$_R$=2.86 min; Mass spectrum (ESI$^+$): m/z=244/246 (Br) [M+H]$^+$.

Step 2:
1-(4-bromo-pyridin-2-yl)-cyclopropanecarboxylic acid ethyl ester

NaH (55% in mineral oil, 0.72 g) was added to a solution of (4-bromo-pyridin-2-yl)-acetic acid ethyl ester (1.80 g) in N,N-dimethylformamide (20 mL) chilled in an ice bath. The resulting mixture was stirred for 10 min at room temperature and then cooled again in an ice bath. 1,2-Dibromoethane (0.70 mL) was added dropwise and the cooling bath was removed. The mixture was stirred at room temperature overnight. Brine was added and the resulting mixture was extracted with ethyl acetate. The combined extracts were washed with brine and dried (MgSO$_4$). The solvent was evaporated and the residue was chromatographed on silica gel (cyclohexane/ethyl acetate 95:5→1:1) to give the title compound as an oil. Yield: 1.28 g (64% of theory); Mass spectrum (ESI$^+$): m/z=270/272 (Br) [M+H]$^+$.

INTERMEDIATE 34

4-(5-Bromo-pyridin-2-yl)-tetrahydro-pyran-4-carboxylic acid amide

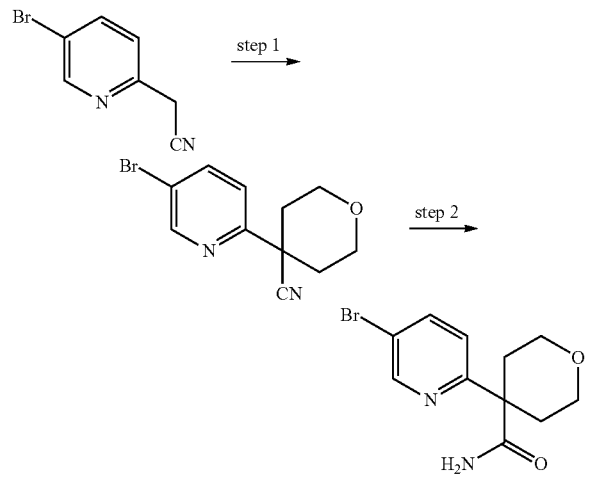

Step 1: 4-(5-bromo-pyridin-2-yl)-tetrahydro-pyran-4-carbonitrile

NaH (55% in mineral oil, 0.23 g) was added to a solution of (5-bromo-pyridin-2-yl)-acetonitrile (0.50 g) in N,N-dimethylformamide (5 mL) chilled in an ice bath. The resulting mixture was stirred for 10 min in the cooling bath prior to the dropwise addition of bis(2-bromoethyl)ether (0.35 mL) dissolved in N,N-dimethylformamide (2 mL). The mixture was stirred with cooling for 2 h and at room temperature for 1 h. Water was added and the resulting mixture was extracted with ethyl acetate. The combined extracts were washed with brine and dried (MgSO$_4$). The solvent was evaporated and the residue was chromatographed on silica gel (cyclohexane/ethyl acetate 4:1→1:1) to give the title compound as a colorless oil. Yield: 0.62 g (91% of theory); LC (method 1): t$_R$=1.70 min; Mass spectrum (ESI$^+$): m/z=267/269 (Br) [M+H]$^+$.

Step 2: 4-(5-bromo-pyridin-2-yl)-tetrahydro-pyran-4-carboxylic acid amide

The title compound was prepared from 4-(5-bromo-pyridin-2-yl)-tetrahydro-pyran-4-carbonitrile following a procedure analogous to that described in Intermediate 3. Yield: 85% of theory; LC (method 1): t$_R$=1.43 min; Mass spectrum (ESI$^+$): m/z=285/287 (Br) [M+H]$^+$.

INTERMEDIATE 35

1-(5-Bromo-pyridin-2-yl)-cyclobutanecarboxylic acid amide

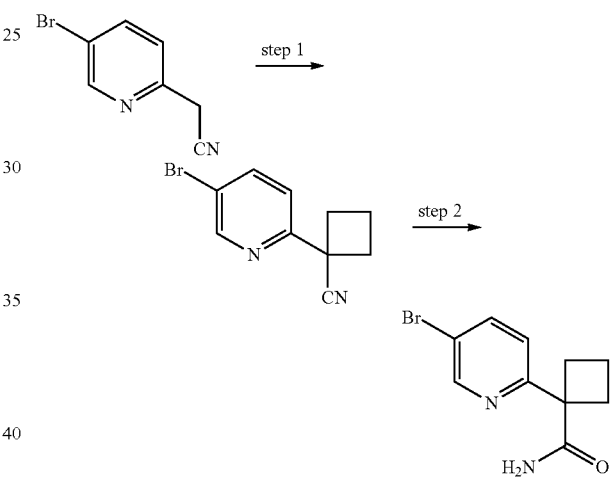

Step: 1:
1-(5-bromo-pyridin-2-yl)-cyclobutanecarbonitrile

The title compound was prepared from (5-bromo-pyridin-2-yl)-acetonitrile and 1,3-dibromopropane following a procedure analogous to that described in Step 1 for Intermediate 34; additionally, 7-bromo-3,4-dihydro-2H-quinolizine-1-carbonitrile was obtained {Yield: 75% of theory; LC (method 1): t$_R$=1.72 min; Mass spectrum (ESI$^+$): m/z=237/239 (Br) [M+H]$^+$}. Yield: 25% of theory; LC (method 1): t$_R$=1.86 min; Mass spectrum (ESI$^+$): m/z=237/239 (Br) [M+H]$^+$.

Step 2:
1-(5-bromo-pyridin-2-yl)-cyclobutanecarboxylic acid amide

The title compound was prepared from 1-(5-bromo-pyridin-2-yl)-cyclobutanecarbonitrile following a procedure analogous to that described in Intermediate 3. Yield: quantitative; LC (method 1): t$_R$=1.62 min; Mass spectrum (ESI$^+$): m/z=255/257 (Br) [M+H]$^+$.

INTERMEDIATE 36

3-(5-Bromo-pyridin-2-yl)-1-methyl-pyrrolidin-2-one

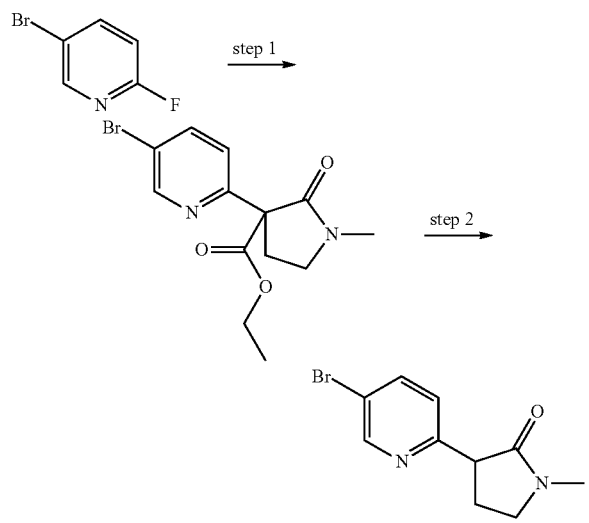

Step 1: 3-(5-bromo-pyridin-2-yl)-1-methyl-2-oxo-pyrrolidine-3-carboxylic acid ethyl ester A mixture of 5-bromo-2-fluoro-pyridine (3.45 g), 1-methyl-2-oxo-pyrrolidine-3-carboxylic acid ethyl ester (5.00 g), cesium carbonate (12.77 g), and dimethyl sulfoxide (10 mL) was stirred at 100° C. overnight. After cooling to room temperature, acetic acid (4.5 mL) was added and the resulting solution was extracted with ethyl acetate. The extract was washed with brine, dried (MgSO$_4$), and concentrated. The residue was chromatographed on silica gel (dichloromethane/ethyl acetate 1:0→1:1) to give the title compound as an oil. Yield: 3.92 g (61% of theory); Mass spectrum (ESI$^+$): m/z=327/329 (Br) [M+H]$^+$.

Step 2: 3-(5-bromo-pyridin-2-yl)-1-methyl-pyrrolidin-2-one

Aqueous NaOH solution (1 mol/L, 3 mL) was added to 3-(5-bromo-pyridin-2-yl)-1-methyl-2-oxo-pyrrolidine-3-carboxylic acid ethyl ester (0.50 g) in ethanol (10 mL) at room temperature. The solution was stirred at room temperature overnight and then neutralized with 1 M aqueous hydrochloric acid. The resulting mixture was concentrated and the residue was taken up in ethyl acetate and filtered to remove the non-dissolving parts. The filtrate was dried (MgSO$_4$) and concentrated. The residue was chromatographed on silica gel (ethyl acetate/methanol 9:1) to give the title compound as a colorless oil. Yield: 0.28 g (71% of theory); Mass spectrum (ESI$^+$): m/z=255/257 (Br) [M+H]$^+$.

INTERMEDIATE 37

3-{(S)-1-[4-(6-Fluoro-pyridin-3-yl)-phenyl]-ethyl}-(S)-6-(2-hydroxy-2-methyl-propyl)-6-phenyl-[1,3]oxazinan-2-one

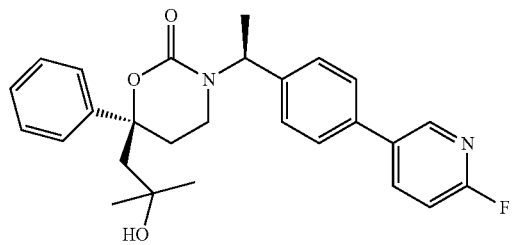 [SMILES: C[C@@H](c1ccc(-c2ccc(F)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 5-bromo-2-fluoro-pyridine following a procedure analogous to that described in Example 1. Yield: 71% of theory; Mass spectrum (ESI$^+$): m/z=449 [M+H]$^+$.

INTERMEDIATE 38

3-{(S)-1-[4-(6-Chloro-pyridazin-3-yl)-phenyl]-ethyl}-(S)-6-(2-hydroxy-2-methyl-propyl)-6-phenyl-[1,3]oxazinan-2-one

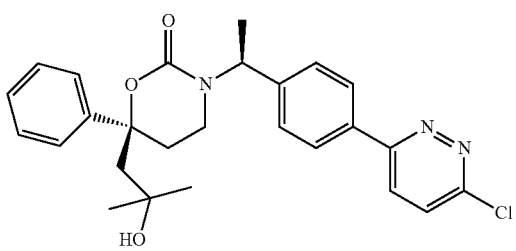 [SMILES: C[C@@H](c1ccc(-c2ccc(Cl)nn2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 3-chloro-6-iodo-pyridazine following a procedure analogous to that described in Example 1. Yield: 62% of theory; LC (method 1): t$_R$=1.88 min; Mass spectrum (ESI$^+$): m/z=466/468 (Cl) [M+H]$^+$.

INTERMEDIATE 39

3-(5-Bromo-pyridin-2-yl)-3-hydroxy-1-methyl-pyrrolidin-2-one

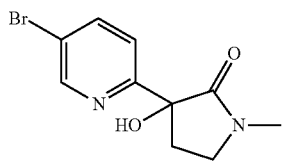

Sodium hydride (55% in mineral oil, 0.13 g) was added to a solution of 3-(5-bromo-pyridin-2-yl)-1-methyl-pyrrolidin-2-one (0.69 g) in N,N-dimethylformamide (10 mL) at room temperature. The resulting mixture was stirred in the presence of air for 1.5 h and then diluted with ethyl acetate. The precipitate formed thereafter was separated by filtration, washed with ether, and dried. The title compound was obtained as a colorless solid. Yield: 0.71 g (93% of theory); LC (method 1): $t_R$=1.38 min; Mass spectrum (ESI$^+$): m/z=271/273 (Br) [M+H]$^+$.

INTERMEDIATE 40

3-(5-Bromo-pyridin-2-yl)-1,3-dimethyl-pyrrolidin-2-one

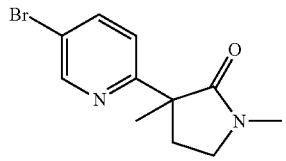

Sodium hydride (55% in mineral oil, 0.17 g) was added to a solution of 3-(5-bromo-pyridin-2-yl)-1-methyl-pyrrolidin-2-one (0.77 g) and methyl iodide (0.44 mL) in N,N-dimethylformamide (15 mL) in argon atmosphere at room temperature. The resulting mixture was stirred at room temperature overnight. Water and ethyl acetate were then added and the organic phase of the resulting mixture was separated. The organic phase was washed with brine, dried (MgSO$_4$), and concentrated. The residue was chromatographed on silica gel (dichloro-methane/ethyl acetate 1:1) to give the title compound as a colorless oil. Yield: 0.50 g (61% of theory); LC (method 1): $t_R$=1.60 min; Mass spectrum (ESI$^+$): m/z=269/271 (Br) [M+H]$^+$.

INTERMEDIATE 41

5-Bromo-1-oxetan-3-yl-1H-pyridin-2-one

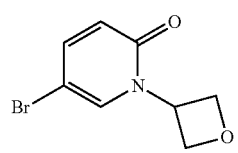 [SMILES: O=c1ccc(Br)cn1C1COC1]

The title compound was prepared from 5-bromopyridin-2(1H)-one and 3-iodooxetane following a procedure analogous to that described for Intermediate 22.

INTERMEDIATE 42

(S)-6-Cyclopropylmethyl-6-(2-hydroxy-2-methyl-propyl)-3-{(S)-1-[4-(4,4,5,5-tetramethyl-[1,3,2]diox-aborolan-2-yl)-phenyl]-ethyl}-[1,3]oxazinan-2-one

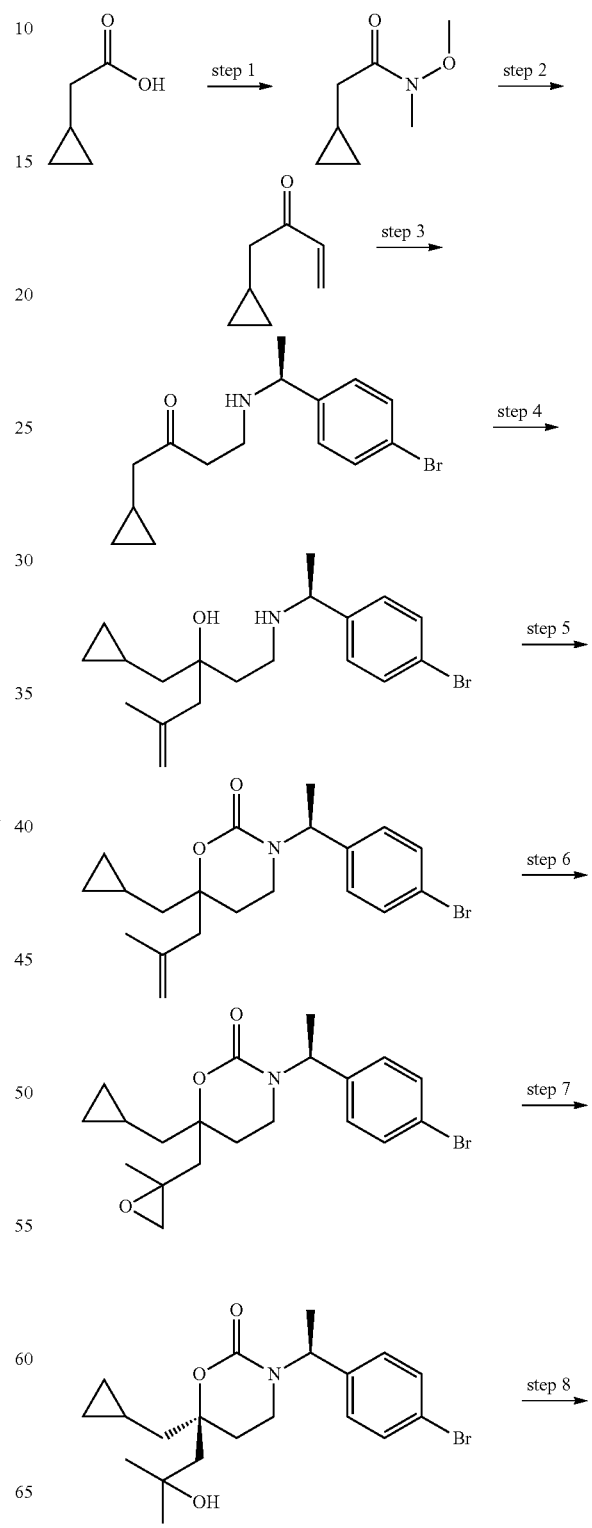

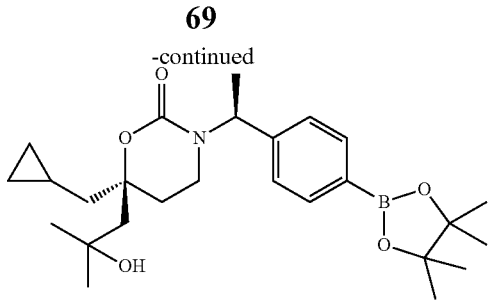

Step 1: 2-cyclopropyl-N-methoxy-N-methyl-acetamide 2-(7-Aza-1H-benzotriazol-1-yl)-1,1,3,3-tetramethyluronium hexafluorophosphate (19.0 g), N-methoxymethanamine (5.0 g), and triethylamine (15.1 g) were added to a solution of 2-cyclopropylacetic acid (5.0 g) in CH$_2$Cl$_2$ (200 mL) at 0° C. The mixture was stirred at room temperature for 3 h. The reaction mixture was then washed with water and the aqueous washing phase was extracted with ethyl acetate (5×50 mL). The combined organic layers were dried (Na$_2$SO$_4$) and concentrated. The residue was purified by chromatography on silica gel (petroleum ether/ethyl acetate 20:1→5:1) to give the title compound. Yield: 4.1 g (58% of theory).

Step 2 1-cyclopropyl-but-3-en-2-one

Vinylmagnesium bromide (1 mol/L, 112 mL) was added to a solution of 2-cyclopropyl-N-methoxy-N-methylacetamide (4.0 g) in tetrahydrofuran (100 mL) under N$_2$ at −78° C. The mixture was stirred at −78° C. for 1 h and then warmed to room temperature. After stirring the mixture at room temperature for 5 h, the reaction was quenched with 1 M aqueous HCl solution and the resulting mixture was extracted with ethyl acetate (4×40 mL) The organic layer was dried (Na$_2$SO$_4$) and concentrated to afford the crude title compound, which was used without further purification. Yield: 2.2 g (71% of theory).

Step 3: 4-[(S)-1-(4-bromo-phenyl)-ethylamino]-1-cyclopropyl-butan-2-one (S)-1-(4-Bromophenyl)ethanamine (3.33 g) was added to a solution of 1-cyclopropylbut-3-en-2-one (3.07 g) in methanol (10 mL). The mixture was heated to 80° C. and stirred at this temperature for 10 min. After cooling to room temperature, the mixture was concentrated to give the crude title compound which was used without further purification. Yield: 5.20 g (crude).

Step 4: 1-[(S)-1-(4-bromo-phenyl)-ethylamino]-3-cyclopropylmethyl-5-methyl-hex-5-en-3-ol (2-Methylallyl)magnesium chloride (1 mol/L, 168 mL) was added to a solution of 1-[(S)-1-(4-bromophenyl)ethylamino]-3-(cyclopropylmethyl)-5-methylhex-5-en-3-ol (5.20 g) in tetrahydrofuran (100 mL) under N$_2$ at −78° C. The mixture was stirred at −78° C. for 2 h. The reaction was then quenched with aqueous NH$_4$Cl solution (50 mL) and the resulting mixture was extracted with ethyl acetate (3×50 mL). The organic layer was dried (Na$_2$SO$_4$) and concentrated. The residue was purified by chromatography on silica gel (petroleum ether/ethyl acetate 10:1→5:1) to give the title compound. Yield: 0.80 g (13% of theory).

Step 5: 3-[(S)-1-(4-bromo-phenyl)-ethyl]-6-cyclopropylmethyl-6-(2-methyl-allyl)-[1,3]oxazinan-2-one Triphosgene (653 mg) was added to a solution of 1-[(S)-1-(4-bromophenyl)ethylamino]-3-(cyclopropylmethyl)-5-methylhex-5-en-3-ol (800 mg) and triethylamine (667 mg) in CH$_2$Cl$_2$ (15 mL) at 0° C. The mixture was stirred at room temperature overnight and the reaction was then quenched with water. The resulting mixture was extracted with CH$_2$Cl$_2$ and the combined organic layer was washed with brine and dried (Na$_2$SO$_4$). The solvent was evaporated and the residue was purified by chromatography on silica gel (petroleum ether/ethyl acetate 3:1) to afford the title compound. Yield 670 mg (78% of theory).

Step 6: 3-[(S)-1-(4-bromo-phenyl)-ethyl]-6-cyclopropylmethyl-6-(2-methyl-oxiranylmethyl)-[1,3]oxazinan-2-one m-Chloroperbenzoic acid (455 mg) was added to a solution of 3-[(S)-1-(4-bromophenyl)-ethyl]-6-(cyclopropylmethyl)-6-(2-methylallyl)-1,3-oxazinan-2-one (516 mg) in CH$_2$Cl$_2$ (15 mL) at 0° C. The mixture was stirred at room temperature overnight. The mixture was then washed with 3% aqueous Na$_2$SO$_2$O$_3$ solution and saturated aqueous NaHCO$_3$ solution. The aqueous washing phase was extracted with ethyl acetate (3×30 mL) and the combined organic layer was washed with brine, dried (Na$_2$SO$_4$), and concentrated to afford the crude title compound which was used without further purification. Yield: 490 mg (91% of theory).

Step 7: 3-[(S)-1-(4-bromo-phenyl)-ethyl]-(S)-6-cyclopropylmethyl-6-(2-hydroxy-2-methyl-propyl)-[1,3]oxazinan-2-one LiBHEt$_3$ solution (1 mol/L, 34 mL) was added dropwise to a solution of 3-[(S)-1-(4-bromophenyl)ethyl]-6-(cyclopropylmethyl)-6-[(2-methyloxiran-2-yl)methyl]-1,3-oxazinan-2-one (1.40 g) in tetrahydrofuran (200 mL) at 0° C. The resulting solution was stirred at 2-3° C. for 1.5 h and then at room temperature for another 3 h. 30% aqueous H$_2$O$_2$ solution (30 mL) was added dropwise at 0° C. and the mixture was diluted with tert-butyl methyl ether (200 mL). The mixture was washed with 3% aqueous Na$_2$SO$_2$O$_3$ solution and saturated aqueous NaHCO$_3$ solution (4×100 mL) and dried (Na$_2$SO$_4$). The solvent was evaporated and the residue was purified by chromatography on silica gel (petroleum ether/ethyl acetate 1:1→3:1) to afford the title compound; besides, the diastereomer, 3-[(S)-1-(4-bromophenyl)ethyl]-(R)-6-(cyclopropylmethyl)-6-(2-hydroxy-2-methylpropyl)-1,3-oxazinan-2-one was also isolated (0.40 g, 29% yield). Yield: 0.55 g (40% of theory).

Step 8: (S)-6-cyclopropylmethyl-6-(2-hydroxy-2-methyl-propyl)-3-{(S)-1-[4-(4,4,5,5-tetramethyl-[1,3,2]dioxaborolan-2-yl)-phenyl]-ethyl}-[1,3]oxazinan-2-one

[1,1'-Bis(diphenylphosphino)ferrocene]-dichloropalladium(II) (20 mg) was added to a mixture of 3-[(S)-1-(4-bromophenyl)ethyl]-(S)-6-(cyclopropylmethyl)-6-(2-hydroxy-2-methylpropyl)-1,3-oxazinan-2-one (500 mg), 4,4,4',4',5,5,5',5'-octamethyl-2,2'-bi(1,3,2-dioxaborolane) (1.50 g), and potassium acetate (436 mg) in dimethyl sulfoxide (8 mL) under N₂. The mixture was heated to 85° C. and stirred at this temperature for 3 h. After cooling to room temperature, the reaction mixture was diluted with ethyl acetate (3×30 mL) and washed with water (2×50 mL) and brine (50 mL). The organic phase was dried (Na₂SO₄) and concentrated, and the residue was purified by chromatography on silica gel (petroleum ether/ethyl acetate 1:1) to give the title compound. Yield: 450 mg (81% of theory).

EXAMPLE 1

(S)-6-(2-Hydroxy-2-methyl-propyl)-3-{(S)-1-[4'-(3-hydroxy-oxetan-3-yl)-biphenyl-4-yl]-ethyl}-6-phenyl-[1,3]oxazinan-2-one

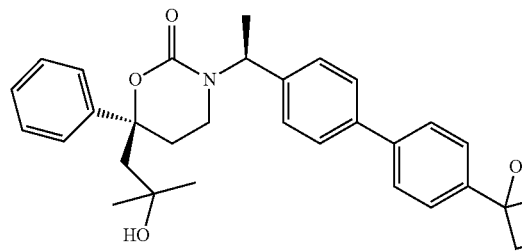

2 M aqueous Na₂CO₃ solution (0.21 mL) was added to a solution of (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one (100 mg) and 3-(4-bromophenyl)-oxetan-3-ol (53 mg) in N,N-dimethylformamide (2 mL). The resulting mixture was sparged with argon for 10 min prior to the addition of [1,1'-bis(diphenylphosphino)ferrocene]-dichloropalladium(II) dichloromethane complex (17 mg). The mixture was heated to 100° C. and stirred at this temperature for 4 h. After cooling to ambient temperature, water was added and the resulting mixture was extracted with ethyl acetate. The combined organic extracts were washed with brine, dried (MgSO₄), and concentrated. The residue was purified by HPLC on reversed phase (acetonitrile/water) to afford the title compound as a foam-like solid. Yield: 34 mg (32% of theory); Mass spectrum (ESI⁺): m/z=502 [M+H]⁺; ¹H NMR (400 MHz, DMSO-d₆) δ 0.82 (s, 3H), 1.19 (s, 3H), 1.47 (d, J=6.9 Hz, 3H), 2.02 (s, 2H), 2.15 (m$_c$, 1H), 2.38-ca. 2.50 (m, 2H) superimposed by D₃CSOCHD₂ signal, 3.01 (m$_c$, 1H), 4.23 (s, 1H), 4.70 (d, J=6.3 Hz, 2H), 4.79 (d, J=6.3 Hz, 2H), 5.44 (incompletely resolved q, 1H), 6.35 (s, 1H), 6.94 (d, J=7.9 Hz, 2H), 7.26-7.43 (m, 7H), 7.59 (d, J=8.2 Hz, 2H), 7.66 (d, J=8.2 Hz, 2H).

EXAMPLE 2

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarbonitrile

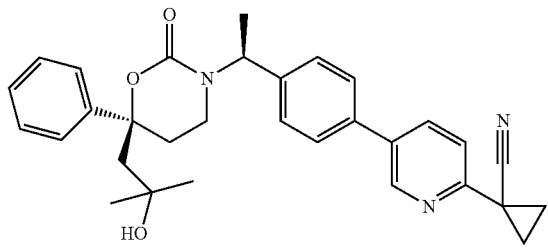 [SMILES: C[C@@H](c1ccc(-c2ccc(C3(C#N)CC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclopropanecarbonitrile following a procedure analogous to that described in Example 1. Yield: 16% of theory; Mass spectrum (ESI⁺): m/z=496 [M+H]⁺; ¹H NMR (400 MHz, DMSO-d₆) δ 0.81 (s, 3H), 1.18 (s, 3H), 1.47 (d, J=7.0 Hz, 3H), 1.70-1.74 (m, 2H), 1.81-1.85 (m, 2H), 2.02 (s, 2H), 2.11-2.20 (m, 1H), 2.38-ca. 2.50 (m, 2H) superimposed by D₃CSOCHD₂ signal, 3.03 (m$_c$, 1H), 4.23 (s, 1H), 5.44 (q, J=7.0 Hz, 1H), 6.98 (d, J=8.3 Hz, 2H), 7.26-7.39 (m, 5H), 7.44 (d, J=8.3 Hz, 2H), 7.60 (d, J=8.3 Hz, 1H), 8.03 (dd, J=8.3, 2.4 Hz, 1H), 8.73 (d, J=2.0 Hz, 1H).

EXAMPLE 3

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid amide

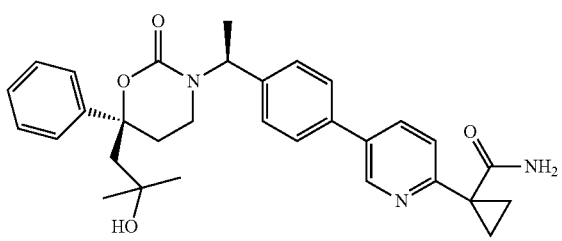 [SMILES: C[C@@H](c1ccc(-c2ccc(C3(C(N)=O)CC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclopropanecarboxylic acid amide following a procedure analogous to that described in Example 1. Yield: 47% of theory; LC (method 2): t$_R$=3.35 min; Mass spectrum (ESI⁺): m/z=514 [M+H]⁺.

EXAMPLE 4

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarbonitrile

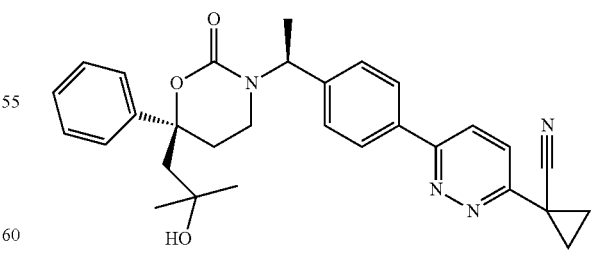

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-chloro-pyridazin-3-yl)-cyclopropanecarbonitrile following a procedure analogous to that described in Example 1. Yield: 51% of theory; LC (method 2): $t_R$=3.42 min; Mass spectrum (ESI$^+$): m/z=497 [M+H]$^+$.

EXAMPLE 5

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid methylamide

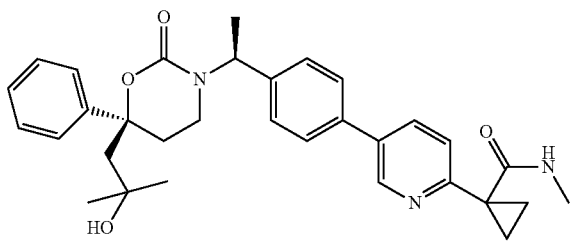 [SMILES: CNC(=O)C1(c2ccc(-c3ccc([C@H](C)N4CC[C@](CC(C)(C)O)(c5ccccc5)OC4=O)cc3)cn2)CC1]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclopropanecarboxylic acid methylamide following a procedure analogous to that described in Example 1. Yield: 91% of theory; LC (method 1): $t_R$=1.88 min; Mass spectrum (ESI$^+$): m/z=528 [M+H]$^+$.

EXAMPLE 6

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid dimethylamide

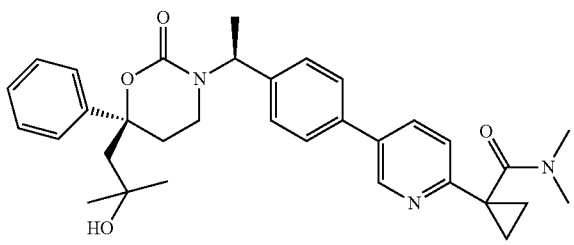 [SMILES: C[C@@H](c1ccc(-c2ccc(C3(C(=O)N(C)C)CC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclopropanecarboxylic acid dimethylamide following a procedure analogous to that described in Example 1. Yield: 75% of theory; LC (method 1): $t_R$=1.92 min; Mass spectrum (ESI$^+$): m/z=542 [M+H]$^+$.

EXAMPLE 7

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarboxylic acid ethyl ester

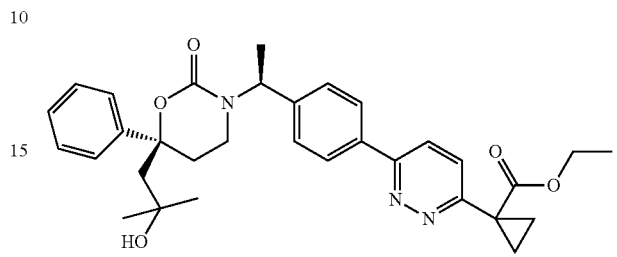

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-chloro-pyridazin-3-yl)-cyclopropanecarboxylic acid ethyl ester following a procedure analogous to that described in Example 1. Yield: 44% of theory; LC (method 1): $t_R$=1.97 min; Mass spectrum (ESI$^+$): m/z=544 [M+H]$^+$.

EXAMPLE 8

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarboxylic acid

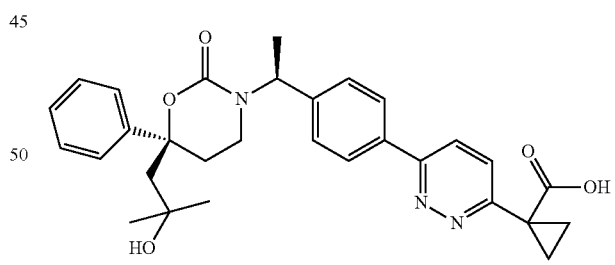

4 M aqueous NaOH solution (1.5 mL) was added to a solution of 1-[6-(4-{1-[6-(2-hydroxy-2-methylpropyl)-2-oxo-6-phenyl-[1,3]oxazinan-3-yl]-ethyl}-phenyl)-pyridazin-3-yl]-cyclopropanecarboxylic acid ethyl ester (0.81 g) in methanol (5 mL) at room temperature. The solution was stirred at room temperature for 2 h and was then neutralized with 1 M aqueous hydrochloric acid. Most of the methanol was evaporated, the residue was diluted with water, and the resulting mixture was extracted with ethyl acetate. The combined extracts were washed with brine, dried (Na$_2$SO$_4$), and concentrated to give the title compound as a solid. Yield: 0.72 g (93% of theory); LC (method 1): $t_R$=1.44 min; Mass spectrum (ESI$^+$): m/z=516 [M+H]$^+$.

EXAMPLE 9

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarboxylic acid amide

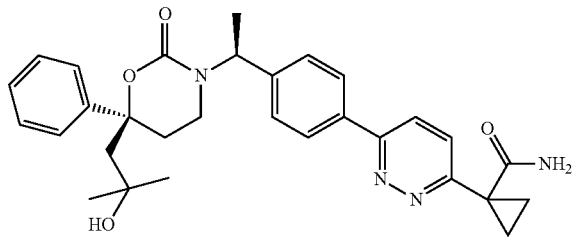 [SMILES: C[C@@H](c1ccc(-c2ccc(C3(C(N)=O)CC3)nn2)cc1)N1CC[C@](CC(C)(C)O)(c2ccccc2)OC1=O]

The title compound was prepared from 1-[6-(4-{(S)-1-[(S)-6-(2-hydroxy-2-methyl-propyl)-2-oxo-6-phenyl-[1,3]oxazinan-3-yl]-ethyl}-phenyl)-pyridazin-3-yl]-cyclopropanecarboxylic acid and ammonia (32% in water) following a procedure analogous to that described in Step 2 for Intermediate 5. Yield: 50% of theory; LC (method 1): $t_R$=1.72 min; Mass spectrum (ESI$^+$): m/z=515 [M+H]$^+$.

EXAMPLE 10

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarboxylic acid methylamide

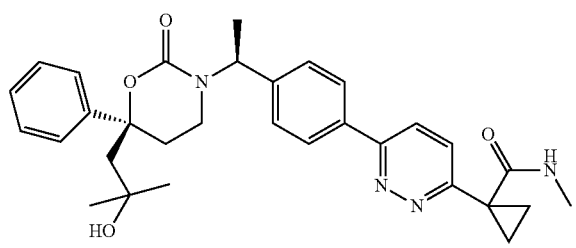 [SMILES: CNC(=O)C1(c2ccc(-c3ccc([C@H](C)N4CC[C@](CC(C)(C)O)(c5ccccc5)OC4=O)cc3)nn2)CC1]

The title compound was prepared from 1-[6-(4-{(S)-1-[(S)-6-(2-hydroxy-2-methyl-propyl)-2-oxo-6-phenyl-[1,3]oxazinan-3-yl]-ethyl}-phenyl)-pyridazin-3-yl]-cyclopropanecarboxylic acid and methylamine (2 mol/L in tetrahydrofuran) following a procedure analogous to that described in Step 2 for Intermediate 5. Yield: 49% of theory; LC (method 1): $t_R$=1.76 min; Mass spectrum (ESI$^+$): m/z=529 [M+H]$^+$.

EXAMPLE 11

1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-cyclopropanecarboxylic acid dimethylamide

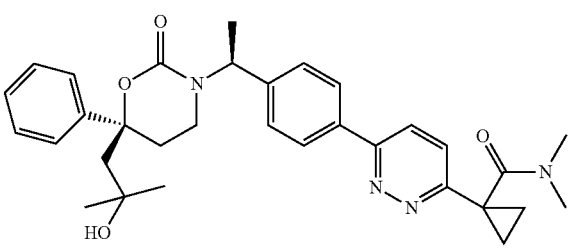 [SMILES: C[C@@H](c1ccc(-c2ccc(C3(C(=O)N(C)C)CC3)nn2)cc1)N1CC[C@](CC(C)(C)O)(c2ccccc2)OC1=O]

The title compound was prepared from 1-[6-(4-{(S)-1-[(S)-6-(2-hydroxy-2-methyl-propyl)-2-oxo-6-phenyl-[1,3]oxazinan-3-yl]-ethyl}-phenyl)-pyridazin-3-yl]-cyclopropanecarboxylic acid and dimethylamine (2 mol/L in tetrahydrofuran) following a procedure analogous to that described in Step 2 for Intermediate 5. Yield: 21% of theory; LC (method 1): $t_R$=1.79 min; Mass spectrum (ESI$^+$): m/z=543 [M+H]$^+$.

EXAMPLE 12

(S)-6-(2-Hydroxy-2-methyl-propyl)-3-((S)-1-{4-[2-oxo-1-((R)-tetrahydro-furan-3-yl)-1,2-dihydro-pyridin-4-yl]-phenyl}-ethyl)-6-phenyl-[1,3]oxazinan-2-one

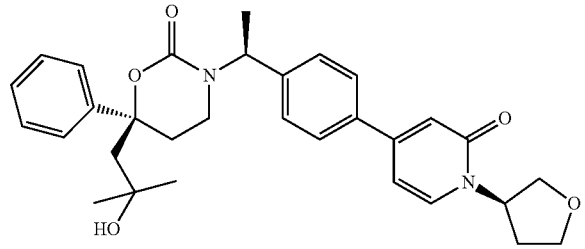 [SMILES: C[C@@H](c1ccc(-c2ccn([C@@H]3CCOC3)c(=O)c2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-1-[(R)-tetrahydro-furan-3-yl]-1H-pyridin-2-one following a procedure analogous to that described in

EXAMPLE 13

(S)-6-(2-Hydroxy-2-methyl-propyl)-3-((S)-1-{4-[2-oxo-1-((S)-tetrahydro-furan-3-yl)-1,2-dihydro-pyridin-4-yl]-phenyl}-ethyl)-6-phenyl-[1,3]oxazinan-2-one

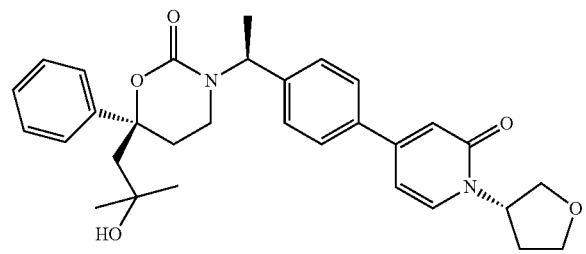 [SMILES: C[C@@H](c1ccc(-c2ccn([C@H]3CCOC3)c(=O)c2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-1-[(S)-tetrahydro-furan-3-yl]-1H-pyridin-2-one following a procedure analogous to that described in Example 1. Yield: 71% of theory; LC (method 3): $t_R$=2.95 min; Mass spectrum (ESI$^+$): m/z=517 [M+H]$^+$.

EXAMPLE 14

(S)-6-(2-Hydroxy-2-methyl-propyl)-6-phenyl-3-((S)-1-{4-[1-(tetrahydro-pyran-4-yl)-1H-pyrazol-4-yl]-phenyl}-ethyl)-[1,3]oxazinan-2-one

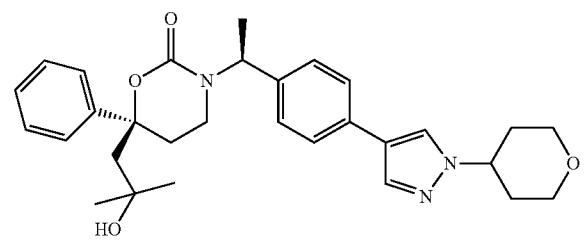 [SMILES: C[C@@H](c1ccc(-c2cnn(C3CCOCC3)c2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-1-(tetrahydro-pyran-4-yl)-1H-pyrazole following a procedure analogous to that described in Example 1. Yield: 18% of theory; LC (method 3): $t_R$=2.98 min; Mass spectrum (ESI$^+$): m/z=504 [M+H]$^+$.

EXAMPLE 15

(S)-6-(2-Hydroxy-2-methyl-propyl)-6-phenyl-3-((S)-1-{4-[1-((R)-tetrahydro-furan-3-yl)-1H-pyrazol-4-yl]-phenyl}-ethyl)-[1,3]oxazinan-2-one

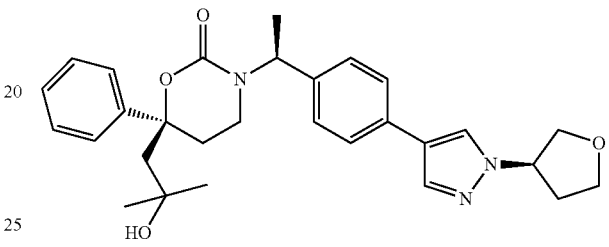

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-1-[(R)-tetrahydro-furan-3-yl]-1H-pyrazole following a procedure analogous to that described in Example 1. Yield: 31% of theory; LC (method 3): $t_R$=3.16 min; Mass spectrum (ESI$^+$): m/z=490 [M+H]$^+$.

EXAMPLE 16

(S)-6-(2-Hydroxy-2-methyl-propyl)-6-phenyl-3-((S)-1-{4-[1-((S)-tetrahydro-furan-3-yl)-1H-pyrazol-4-yl]-phenyl}-ethyl)-[1,3]oxazinan-2-one

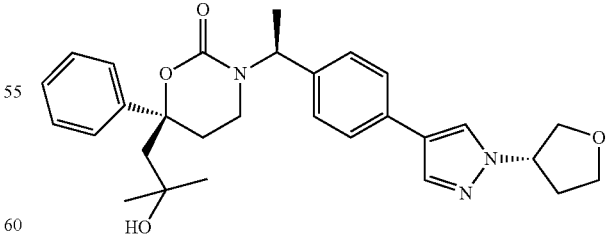

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-1-[(S)-tetrahydro-furan-3-yl]-1H-pyrazole following a procedure analogous to that described in Example 1.

Yield: 37% of theory; LC (method 3): $t_R$=3.16 min; Mass spectrum (ESI$^+$): m/z=490 [M+H]$^+$.

EXAMPLE 17

1-[6-(4-{(S)-1-[(S)-6-(2-Hydroxy-2-methyl-propyl)-2-oxo-6-phenyl-[1,3]oxazinan-3-yl]-ethyl}-phenyl)-pyridin-3-yl]-cyclopropanecarbonitrile

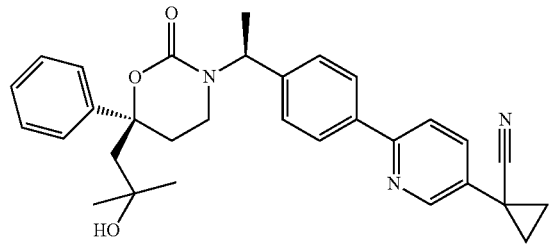 [SMILES: C[C@@H](c1ccc(-c2ccc(C3(C#N)CC3)cn2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-chloro-pyridin-3-yl)-cyclopropanecarbonitrile following a procedure analogous to that described in Example 1. Yield: 48% of theory; LC (method 3): $t_R$=3.52 min; Mass spectrum (ESI$^+$): m/z=496 [M+H]$^+$.

EXAMPLE 18

(S)-6-(2-Hydroxy-2-methyl-propyl)-3-((S)-1-{4-[6-(1-methanesulfonyl-cyclopropyl)-pyridin-3-yl]-phenyl}-ethyl)-6-phenyl-[1,3]oxazinan-2-one

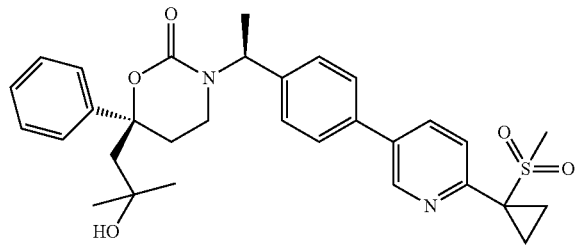 [SMILES: C[C@@H](c1ccc(-c2ccc(C3(S(C)(=O)=O)CC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 5-bromo-2-(1-methanesulfonyl-cyclopropyl)-pyridine following a procedure analogous to that described in Example 1. Yield: 58% of theory; LC (method 1): $t_R$=1.86 min; Mass spectrum (ESI$^+$): m/z=549 [M+H]$^+$.

EXAMPLE 19

1-[6-(4-{(S)-1-[(S)-6-(2-Hydroxy-2-methyl-propyl)-2-oxo-6-phenyl-[1,3]oxazinan-3-yl]-ethyl}-phenyl)-pyridin-3-yl]-cyclopropanecarboxylic acid amide

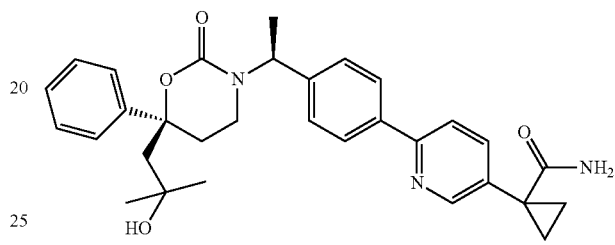

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-chloro-pyridin-3-yl)-cyclopropanecarboxylic acid amide following a procedure analogous to that described in Example 1. Yield: 47% of theory; LC (method 1): $t_R$=1.85 min; Mass spectrum (ESI$^+$): m/z=514 [M+H]$^+$.

EXAMPLE 20

(S)-6-(2-Hydroxy-2-methyl-propyl)-3-((S)-1-{4-[6-(1-methanesulfonyl-cyclopropyl)-pyridin-2-yl]-phenyl}-ethyl)-6-phenyl-[1,3]oxazinan-2-one

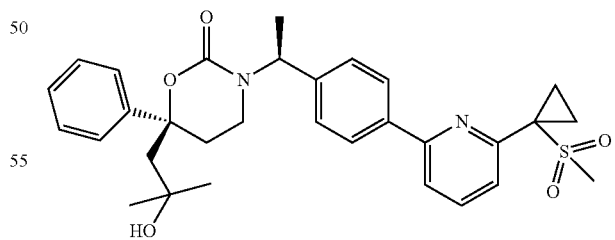

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 2-bromo-6-(1-methanesulfonyl-cyclopropyl)-pyridine following a procedure analogous to that described in Example 1. Yield: 76% of theory; LC (method 1): $t_R$=1.93 min; Mass spectrum (ESI$^+$): m/z=549 [M+H]$^+$.

Example 1. Yield: 68% of theory; LC (method 1): $t_R$=1.92 min; Mass spectrum (ESI$^+$): m/z=514 [M+H]$^+$.

EXAMPLE 21

(S)-6-(2-Hydroxy-2-methyl-propyl)-3-((S)-1-{4-[2-(1-methanesulfonyl-cyclopropyl)-pyridin-4-yl]-phenyl}-ethyl)-6-phenyl-[1,3]oxazinan-2-one

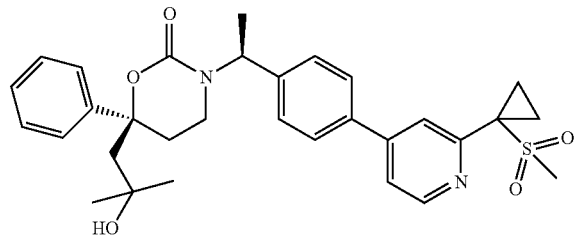 [SMILES: C[C@@H](c1ccc(-c2ccnc(C3(S(C)(=O)=O)CC3)c2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-bromo-2-(1-methanesulfonyl-cyclopropyl)-pyridine following a procedure analogous to that described in Example 1. Yield: 84% of theory; LC (method 1): $t_R$=1.86 min; Mass spectrum (ESI$^+$): m/z=549 [M+H]$^+$.

EXAMPLE 22

1-[6-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid amide

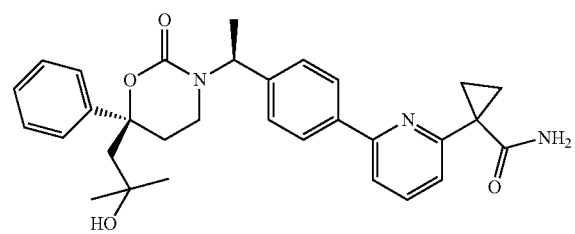 [SMILES: C[C@@H](c1ccc(-c2cccc(C3(C(N)=O)CC3)n2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-bromo-pyridin-2-yl)-cyclopropanecarboxylic acid amide following a procedure analogous to that described in

EXAMPLE 23

1-[6-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid methylamide

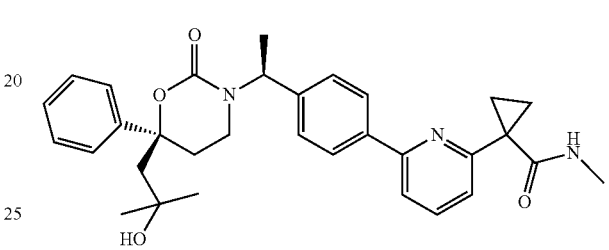

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-bromo-pyridin-2-yl)-cyclopropanecarboxylic acid methylamide following a procedure analogous to that described in Example 1. Yield: 74% of theory; LC (method 1): $t_R$=1.96 min; Mass spectrum (ESI$^+$): m/z=528 [M+H]$^+$.

EXAMPLE 24

1-[6-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid dimethylamide

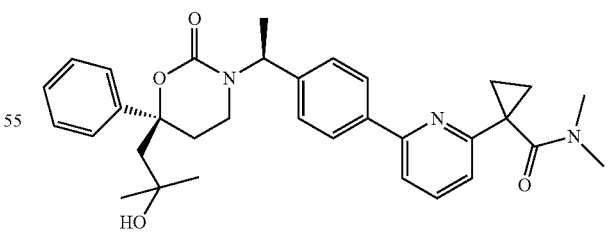

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(6-bromo-pyridin-2-yl)-cyclopropanecarboxylic acid dimethylamide following a procedure analogous to that described in Example 1. Yield: 66% of theory; LC (method 1): $t_R$=2.00 min; Mass spectrum (ESI$^+$): m/z=542 [M+H]$^+$.

EXAMPLE 25

(S)-6-(2-Hydroxy-2-methyl-propyl)-3-((S)-1-{4-[5-(1-methanesulfonyl-cyclopropyl)-pyridin-2-yl]-phenyl}-ethyl)-6-phenyl-[1,3]oxazinan-2-one

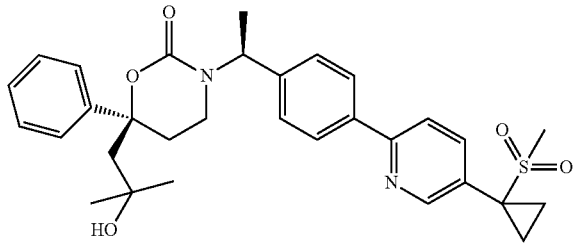 [SMILES: C[C@@H](c1ccc(-c2ccc(C3(S(C)(=O)=O)CC3)cn2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 2-chloro-5-(1-methanesulfonyl-cyclopropyl)-pyridine following a procedure analogous to that described in Example 1. Yield: 20% of theory; LC (method 1): $t_R$=1.83 min; Mass spectrum (ESI$^+$): m/z=549 [M+H]$^+$.

EXAMPLE 26

(S)-6-(2-hydroxy-2-methylpropyl)-3-((S)-1-{4-[1-(oxetan-3-yl)-2-oxo-1,2-dihydropyridin-4-yl]phenyl}ethyl)-6-phenyl-1,3-oxazinan-2-one

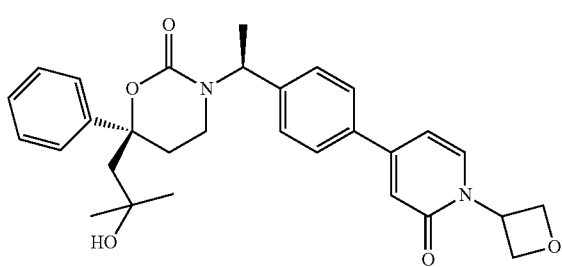 [SMILES: C[C@@H](c1ccc(-c2ccn(C3COC3)c(=O)c2)cc1)N1CC[C@](CC(C)(C)O)(c2ccccc2)OC1=O]

Pd(PPh$_3$)$_4$ (10 mg) was added to a solution of 4-bromo-1-(oxetan-3-yl)pyridin-2(1H)-one (14 mg) in 1,2-dimethoxyethane (6 mL) under nitrogen. The formed mixture was stirred at room temperature for 1 h prior to the addition of (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (24 mg) in ethanol (2 mL) followed by saturated aqueous NaHCO$_3$ solution (2 mL). The mixture was stirred at 100° C. for 2 h. After cooling to room temperature, the reaction was quenched with water and the resulting mixture was extracted with ethyl acetate (3×). The combined organic phase was concentrated and the residue was purified by preparative HPLC to give the title compound. Yield: 14 mg (55% of theory); LC (method 4): $t_R$=0.97 min; Mass spectrum (ESI$^+$): m/z=445 [M-Me$_2$CO+H]$^+$; $^1$H NMR (CDCl$_3$) δ 1.09 (s, 3H), 1.12 (s, 3H), 1.45 (d, 3H), 2.10-2.30 (m, 4H), 2.35 (m, 1H), 2.72 (m, 1H), 4.70 (m, 2H), 5.09 (m, 2H), 5.63 (m, 1H), 5.71 (m, 1H), 6.43 (m, 1H), 6.61 (m, 1H), 6.98 (d, 2H), 7.28 (m, 7H), 7.61 (d, 1H).

EXAMPLE 27

3-((S)-1-{4-[1-(azetidin-3-yl)-2-oxo-1,2-dihydropyridin-4-yl]phenyl}ethyl)-(S)-6-(2-hydroxy-2-methyl-propyl)-6-phenyl-1,3-oxazinan-2-one

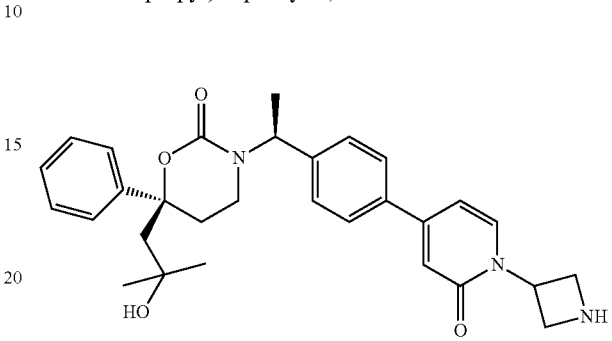

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 3-(4-bromo-2-oxo-2H-pyridin-1-yl)-azetidine-1-carboxylic acid tert-butyl ester following a procedure analogous to that described in Example 26, followed by removal of the tert-butoxycarbonyl group using F$_3$CCO$_2$H in CH$_2$Cl$_2$. LC (method 4): $t_R$=0.82 min; Mass spectrum (ESI$^+$): m/z=502 [M+H]$^+$; $^1$H NMR (CDCl$_3$) δ 1.05 (s, 3H), 1.12 (s, 3H), 1.49 (d, 3H), 2.10-2.22 (m, 4H), 2.34 (m, 1H), 2.72 (m, 1H), 3.71 (m, 2H), 4.13 (m, 2H), 5.52 (m, 1H), 5.64 (m, 1H), 6.40 (m, 1H), 6.61 (m, 1H), 6.97 (d, 2H), 7.25 (m, 7H), 7.71 (d, 1H).

EXAMPLE 28

(S)-6-(2-hydroxy-2-methylpropyl)-3-((S)-1-{4-[2-(2-oxoimidazolidin-1-yl)pyrimidin-5-yl]phenyl}ethyl)-6-phenyl-1,3-oxazinan-2-one

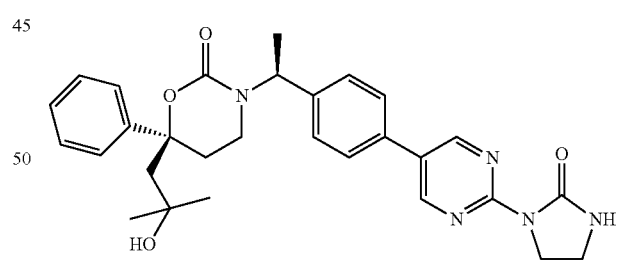

Pd(PPh$_3$)$_4$ (1 mg) was added to a mixture of 1-(5-bromopyrimidin-2-yl)imidazolidin-2-one (13 mg), (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (38.6 mg) and Na$_2$CO$_3$ (17 mg) in toluene (3 mL), ethanol (2 mL), and H$_2$O (1 mL) at room temperature. The reaction mixture was heated to 100° C. under nitrogen and stirred at this temperature for 2 h. After cooling to room temperature, the mixture was concentrated to give an oil, which was purified by preparative HPLC to afford the title compound. Yield: 3.1 mg (11% of theory); LC (method 4): $t_R$=0.93 min; Mass spectrum (ESI$^+$): m/z=516 [M+H]$^+$; $^1$H NMR (CD$_3$OD) δ

0.92 (s, 3H), 1.32 (s, 3H), 1.58 (d, 3H), 2.06 (s, 2H), 2.19 (m, 2H), 2.50 (m, 2H), 3.58 (m, 2H), 4.20 (m, 2H), 5.62 (m, 1H), 7.11 (d, 2H), 7.33 (m, 5H), 7.42 (d, 2H), 8.78 (m, 2H).

EXAMPLE 29

(S)-6-(2-hydroxy-2-methylpropyl)-3-((S)-1-{4-[2-(3-methyl-2-oxoimidazolidin-1-yl)pyrimidin-5-yl]phenyl}ethyl)-6-phenyl-1,3-oxazinan-2-one

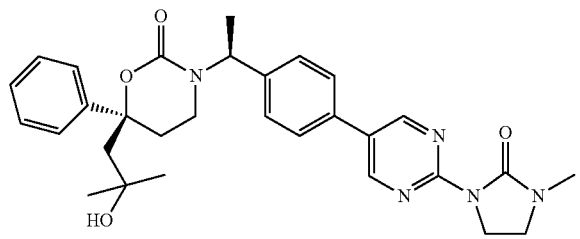 [SMILES: C[C@@H](c1ccc(-c2cnc(N3CCN(C)C3=O)nc2)cc1)N1CC[C@](CC(C)(C)O)(c2ccccc2)OC1=O]

Pd(PPh$_3$)$_4$ (1 mg) was added to a solution of 1-(5-bromopyrimidin-2-yl)-3-methylimidazolidin-2-one (10 mg), (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (38.0 mg), and Na$_2$CO$_3$ (17 mg) in toluene (3 mL), ethanol (2 mL), and H$_2$O (1 mL) under nitrogen at room temperature. The reaction mixture was heated to 100° C. under nitrogen and stirred at this temperature for 2 h. After cooling to room temperature, the mixture was concentrated to afford an oil, which was purified by preparative HPLC to give the title compound. Yield: 2.4 mg (12% of theory); LC (method 4): t$_R$=0.98 min; Mass spectrum (ESI$^+$): m/z=530 [M+H]$^+$; $^1$H NMR (CD$_3$OD) δ 0.88 (s, 3H), 1.32 (s, 3H), 1.48 (d, 3H), 2.05 (m, 2H), 2.12 (m, 2H), 2.41 (m, 2H), 2.81 (s, 3H), 3.42 (m, 2H), 4.01 (m, 2H), 5.52 (m, 1H), 7.02 (d, 2H), 7.26 (m, 5H), 7.31 (m, 2H), 8.67 (s, 2H).

EXAMPLE 30

(S)-6-(2-hydroxy-2-methylpropyl)-3-((S)-1-{4-[2-(2-oxopyrrolidin-1-yl)pyrimidin-5-yl]phenyl]ethyl}-6-phenyl-1,3-oxazinan-2-one

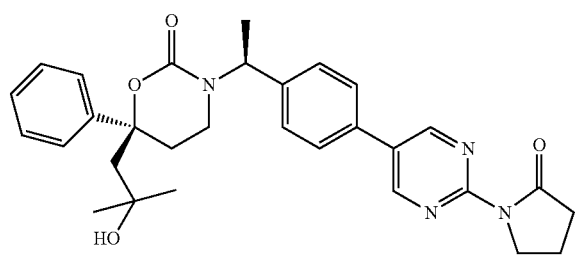 [SMILES: C[C@@H](c1ccc(-c2cnc(N3CCCC3=O)nc2)cc1)N1CC[C@](CC(C)(C)O)(c2ccccc2)OC1=O]

The title compound was prepared from 1-(5-bromopyrimidin-2-yl)pyrrolidin-2-one and (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one following a procedure analogous to that described in Example 28. LC (method 4): t$_R$=1.02 min; Mass spectrum (ESI$^+$): m/z=515 [M+H]$^+$; $^1$H NMR (CD$_3$OD) δ 0.81 (s, 3H), 1.17 (s, 3H), 1.47 (d, 3H), 2.09 (m, 3H), 2.13 (m, 2H), 2.41 (m, 2H), 2.57 (m, 2H), 2.96 (m, 1H), 4.08 (m, 2H), 5.52 (m, 1H), 7.02 (d, 2H), 7.23 (m, 5H), 7.38 (m, 2H), 8.78 (s, 2H).

EXAMPLE 31

3-((S)-1-{4-[6-(azetidin-1-yl)pyridazin-3-yl]phenyl}ethyl)-(S)-6-(2-hydroxy-2-methylpropyl)-6-phenyl-1,3-oxazinan-2-one

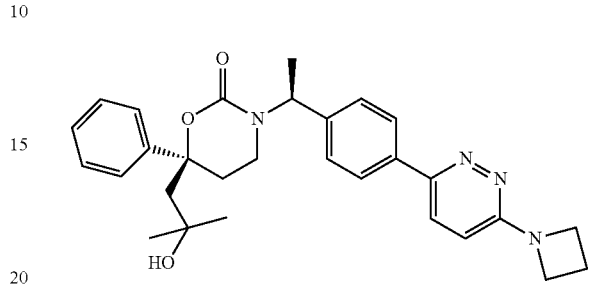

A heavy-walled glass vial was charged with a stir bar, (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (26 mg), 3-(azetidin-1-yl)-6-chloropyridazine (18 mg), K$_3$PO$_4$ (20 mg), Pd$_2$(dibenzylideneacetone)$_3$ (5.0 mg), and tricyclohexylphosphine (3.7 mg, 0.013 mmol). The vial was capped with a septum and flushed with N$_2$. 1,4-Dioxane (1 mL) and water (0.1 mL) were introduced by syringe and the mixture was heated to 100° C. in an oil bath and stirred at this temperature for 18 h. After cooling to room temperature, the mixture was diluted with methanol (0.75 mL) and 5% aqueous HCl (0.25 mL) and filtered. The filtrate was purified by preparative HPLC to afford the title compound as its trifluoroacetic acid salt. Yield: 9 mg (34% of theory); LC (method 5): t$_R$=1.12 min; Mass spectrum (ESI$^+$): m/z=487 [M+H]$^+$; $^1$H NMR (CD$_3$OD) δ 0.97 (s, 3H), 1.26 (s, 3H), 1.58 (d, 3H), 2.16 (s, 2H), 2.24 (m, 1H), 2.40-2.70 (m, 4H), 3.09 (m, 1H), 4.43 (m, 4H), 5.58 (q, 1H), 7.12 (d, 2H), 7.25-7.35 (m, 5H), 7.44 (d, 1H), 7.74 (d, 2H), 8.21 (d, 1H).

EXAMPLE 32

3-((S)-1-{4-[2-(3-fluoroazetidin-1-yl)pyrimidin-5-yl]phenyl}ethyl)-(S)-6-(2-hydroxy-2-methylpropyl)-6-phenyl-1,3-oxazinan-2-one

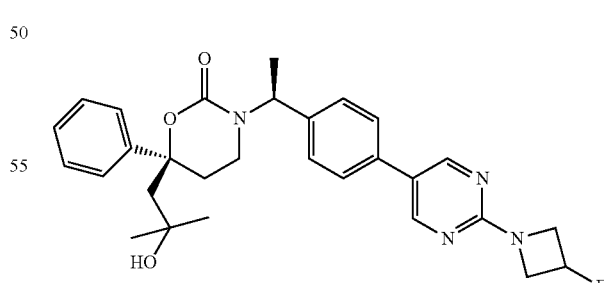

The title compound was prepared following a procedure analogous to Example 31 using (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 5-bromo-2-(3-fluoroazetidin-1-yl)pyrimidine. LC (method 5): t$_R$=1.55 min; Mass spectrum (ESI$^+$): m/z=505 [M+H]$^+$;

¹H NMR (CD₃OD) δ 0.95 (s, 3H), 1.25 (s, 3H), 1.54 (d, 3H), 2.12 (s, 2H), 2.20 (m, 1H), 2.44 (m, 2H), 3.03 (m, 1H), 4.21 (m, 2H), 4.46 (m, 2H), 5.45-5.60 (m, 2H), 7.03 (d, 2H), 7.25-7.40 (m, 7H), 8.53 (s, 2H).

EXAMPLE 33

3-((S)-1-{4-[2-(3,3-difluoroazetidin-1-yl)pyrimidin-5-yl]phenyl}ethyl)-(S)-6-(2-hydroxy-2-methylpropyl)-6-phenyl-1,3-oxazinan-2-one

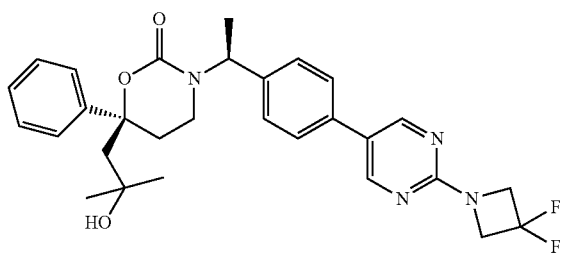 [SMILES: C[C@@H](c1ccc(-c2cnc(N3CC(F)(F)C3)nc2)cc1)N1CC[C@](CC(C)(C)O)(c2ccccc2)OC1=O]

The title compound was prepared following a procedure analogous to Example 31 using (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 5-bromo-2-(3,3-difluoroazetidin-1-yl)pyrimidine. LC (method 5): t_R=1.7 min; Mass spectrum (ESI⁺): m/z=523 [M+H]⁺; ¹H NMR (CD₃OD) δ 0.94 (s, 3H), 1.25 (s, 3H), 1.54 (d, 3H), 2.14 (s, 2H), 2.20 (m, 1H), 2.46 (m, 2H), 3.03 (m, 1H), 4.51 (m, 4H), 5.57 (q, 1H), 7.07 (d, 2H), 7.25-7.40 (m, 7H), 8.60 (s, 2H).

EXAMPLE 34

3-((S)-1-{4-[2-(azetidin-1-yl)pyrimidin-5-yl)phenyl]ethyl}-(S)-6-(2-hydroxy-2-methylpropyl)-6-phenyl-1,3-oxazinan-2-one

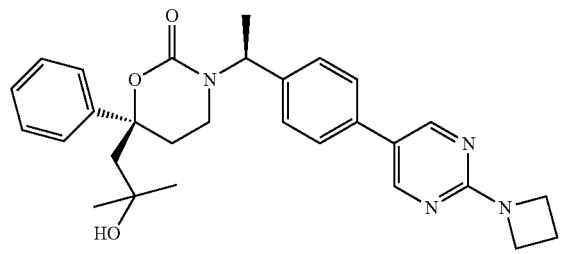 [SMILES: C[C@@H](c1ccc(-c2cnc(N3CCC3)nc2)cc1)N1CC[C@](CC(C)(C)O)(c2ccccc2)OC1=O]

The title compound was prepared following a procedure analogous to Example 31 using (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 2-(azetidin-1-yl)-5-bromopyrimidine. LC (method 5): t_R=1.48 min; Mass spectrum (ESI⁺): m/z=487 [M+H]⁺; ¹H NMR (CD₃OD) δ 0.95 (s, 3H), 1.23 (s, 3H), 1.55 (d, 3H), 2.14 (s, 2H), 2.20 (m, 1H), 2.40-2.60 (m, 4H), 3.04 (m, 1H), 4.33 (m, 4H), 5.57 (q, 1H), 7.08 (d, 2H), 7.25-7.40 (m, 7H), 8.62 (s, 2H).

EXAMPLE 35

(S)-6-(2-hydroxy-2-methylpropyl)-3-((S)-1-{4-[2-(3-hydroxyazetidin-1-yl)pyrimidin-5-yl]phenyl}ethyl)-6-phenyl-1,3-oxazinan-2-one

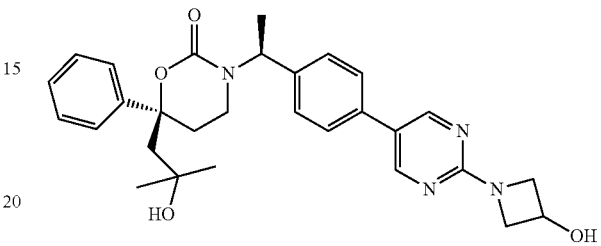

A heavy-walled glass vial was charged with (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one (13 mg), 1-(5-bromopyrimidin-2-yl)azetidin-3-ol trifluoroacetic acid salt (18 mg), Cs₂CO₃ (18 mg), water (0.1 mL), and 1,4-dioxane (1 mL). The mixture was sparged with N₂ for 10 min before PdCl₂[1,1'-bis(diphenylphosphino)ferrocene] (2 mg) was added. The mixture was sparged with N₂ for 10 min and then heated in a microwave oven at 110° C. for 30 min. After cooling to room temperature, the reaction mixture was purified by preparative HPLC to afford the title compound as its trifluoroacetic acid salt as an oil. Yield: 12.1 mg (89% of theory); LC (method 5): t_R=1.3 min; Mass spectrum (ESI⁺): m/z=503 [M+H]⁺; ¹H NMR (CD₃OD) δ 0.95 (s, 3H), 1.26 (s, 3H), 1.56 (d, 3H), 2.16 (s, 2H), 2.23 (m, 1H), 2.47 (m, 2H), 3.05 (m, 1H), 4.07 (m, 2H), 4.49 (m, 2H), 4.73 (m, 1H), 5.57 (q, 1H), 7.09 (d, 2H), 7.25-7.40 (7H), 8.63 (s, 2H).

EXAMPLE 36

(S)-6-(2-hydroxy-2-methylpropyl)-3-((S)-1-{4-[2-(2-oxopyridin-1 (2H)-yl)thiazol-5-yl]phenyl}ethyl)-6-phenyl-1,3-oxazinan-2-one

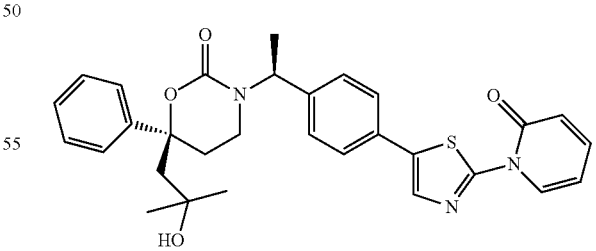

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 1-(5-bromothiazol-2-yl)pyridin-2(1H)-one following a procedure analogous to that described in Example 31. LC (method 5): t_R=1.72 min; Mass spectrum (ESI⁺): m/z=472, 530 [M+H]⁺; ¹H NMR (CDCl₃) δ 1.12 (s, 3H), 1.18 (s, 3H), 1.56 (d, 3H), 2.19 (s, 2H), 2.25 (m, 1H), 2.39 (m, 1H), 2.60 (m, 1H), 2.86 (m, 1H), 5.69 (q, 1H), 6.45 (t, 1H), 6.80 (d, 1H), 6.99 (d, 2H), 7.25-7.40 (7H), 7.46 (m, 1H), 7.77 (s, 1H), 8.81 (d, 1H).

EXAMPLE 37

(S)-6-(2-hydroxy-2-methylpropyl)-3-((S)-1-{4-[2-(2-oxopyridin-1(2H)-yl)thiazol-4-yl]phenyl}ethyl)-6-phenyl-1,3-oxazinan-2-one

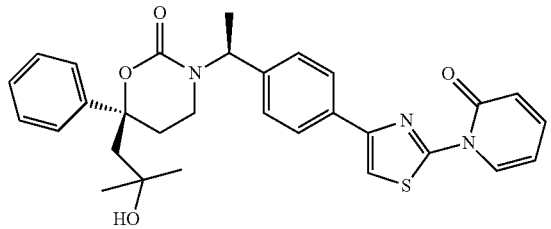 [SMILES: C[C@@H](c1ccc(-c2csc(-n3ccccc3=O)n2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 1-(4-bromothiazol-2-yl)pyridin-2(1H)-one following a procedure analogous to that described in Example 31. LC (method 5): $t_R$=1.73 min; Mass spectrum (ESI$^+$): m/z=472, 530 [M+H]$^+$; $^1$H NMR (CDCl$_3$) δ 1.10 (s, 3H), 1.20 (s, 3H), 1.57 (d, 3H), 2.20-2.30 (m, 4H), 2.39 (m, 1H), 2.91 (m, 1H), 5.72 (q, 1H), 6.52 (t, 1H), 6.83 (d, 1H), 7.05 (d, 2H), 7.20-7.40 (m, 6H), 7.50 (m, 1H), 7.70 (d, 2H), 8.98 (d, 1H).

EXAMPLE 38

(S)-6-(2-hydroxy-2-methylpropyl)-3-{(S)-1-[4-(2-morpholinopyrimidin-4-yl)phenyl]ethyl}-6-phenyl-1,3-oxazinan-2-one

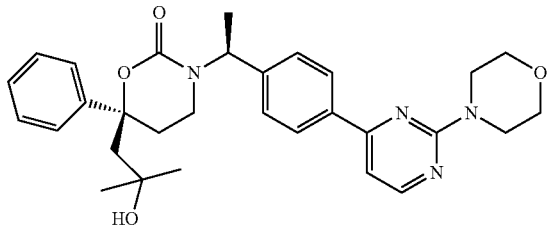 [SMILES: C[C@@H](c1ccc(-c2ccnc(N3CCOCC3)n2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]ethyl}-1,3-oxazinan-2-one and 4-(4-bromopyrimidin-2-yl)morpholine following a procedure analogous to that described in Example 35. LC (method 5): $t_R$=1.15 min; Mass spectrum (ESI$^+$): m/z=517 [M+H]$^+$; $^1$H NMR (CD$_3$OD) δ 0.95 (s, 3H), 1.25 (s, 3H), 1.58 (d, 3H), 2.17 (s, 2H), 2.30 (m, 1H), 2.50 (m, 2H), 3.15 (m, 1H), 3.29 (m, 4H), 3.84 (m, 4H), 5.59 (q, 1H), 7.05 (d, 1H), 7.12 (d, 2H), 7.25-7.40 (5H), 7.94 (d, 2H), 8.17 (d, 1H).

EXAMPLE 39

(S)-6-(2-hydroxy-2-methylpropyl)-3-((S)-1-{4-[6-(2-oxopiperidin-1-yl)pyridin-2-yl]phenyl}ethyl)-6-phenyl-1,3-oxazinan-2-one

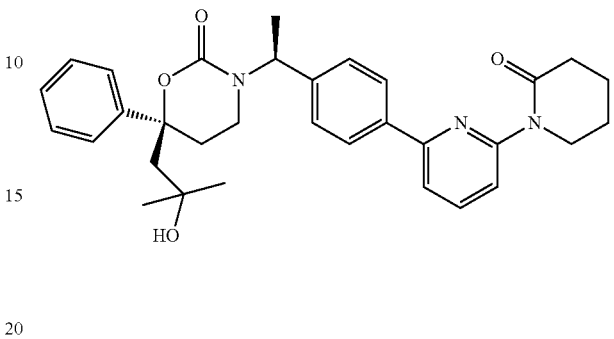

The title compound was prepared from 1-[6-(4,4,5,5-tetramethyl-1,3,2-dioxaborolan-2-yl)pyridin-2-yl]piperidin-2-one (purchased from CombiPhos Catalysts Inc., Princeton, N.J., USA) and (S)-3-[(S)-1-(4-bromophenyl)ethyl]-6-(2-hydroxy-2-methyl-propyl)-6-phenyl-1,3-oxazinan-2-one following a procedure analogous to that described in Example 35. LC (method 5): $t_R$=1.62 min; Mass spectrum (ESI$^+$): m/z=528 [M+H]$^+$.

EXAMPLE 40

(S)-6-(2-hydroxy-2-methylpropyl)-3-{(S)-1-[4-(6-morpholinopyridin-2-yl)phenyl]ethyl}-6-phenyl-1,3-oxazinan-2-one

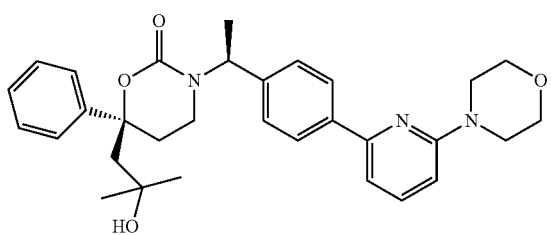

The title compound was prepared from 4-[6-(4,4,5,5-tetramethyl-1,3,2-dioxaborolan-2-yl)pyridin-2-yl]morpholine (purchased from CombiPhos Catalysts Inc., Princeton, N.J., USA) and (S)-3-[(S)-1-(4-bromophenyl)ethyl]-6-(2-hydroxy-2-methyl-propyl)-6-phenyl-1,3-oxazinan-2-one following a procedure analogous to that described in Example 35. LC (method 5): $t_R$=1.68 min; Mass spectrum (ESI$^+$): m/z=516 [M+H]$^+$; $^1$H NMR (CD$_3$OD) δ 0.95 (s, 3H), 1.24 (s, 3H), 1.58 (d, 3H), 2.17 (s, 2H), 2.25 (m, 1H), 2.47 (m, 2H), 3.08 (m, 1H), 3.66 (m, 4H), 3.83 (m, 4H), 5.58 (q, 1H), 7.12 (4H), 7.25-7.40 (5H), 7.63 (d, 2H), 7.88 (m, 1H).

Example 1. Yield: 62% of theory; LC (method 2): $t_R$=2.02 min; Mass spectrum (ESI$^+$): m/z=542 [M+H]$^+$.

EXAMPLE 41

(S)-6-(2-hydroxy-2-methylpropyl)-3-((S)-1-{4-[6-(2-oxopyridin-1 (2H)-yl)pyridin-2-yl]phenyl}ethyl)-6-phenyl-1,3-oxazinan-2-one

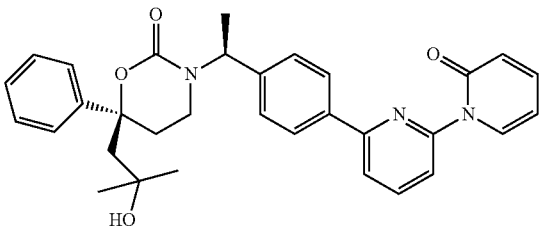 [SMILES: C[C@@H](c1ccc(-c2cccc(-n3ccccc3=O)n2)cc1)N1CC[C@](CC(C)(C)O)(c2ccccc2)OC1=O]

The title compound was prepared from 1-[6-(4,4,5,5-tetramethyl-1,3,2-dioxaborolan-2-yl)pyridin-2-yl]pyridin-2 (1H)-one (purchased from CombiPhos Catalysts Inc., Princeton, N.J., USA) and (S)-3-[(S)-1-(4-bromophenyl)ethyl]-6-(2-hydroxy-2-methylpropyl)-6-phenyl-1,3-oxazinan-2-one following a procedure analogous to that described in Example 35. LC (method 5): $t_R$=1.53 min; Mass spectrum (ESI$^+$): m/z=466, 524 [M+H]$^+$; $^1$H NMR (CD$_3$OD) δ 0.94 (s, 3H), 1.26 (s, 3H), 1.57 (d, 3H), 2.16 (s, 2H), 2.25 (m, 1H), 2.47 (m, 2H), 3.04 (m, 1H), 5.59 (q, 1H), 6.54 (t, 1H), 6.64 (d, 1H), 7.08 (d, 2H), 7.25-7.40 (5H), 7.63 (m, 1H), 7.66 (m, 1H), 7.85-8.00 (5H).

EXAMPLE 42

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopentanecarboxylic acid amide

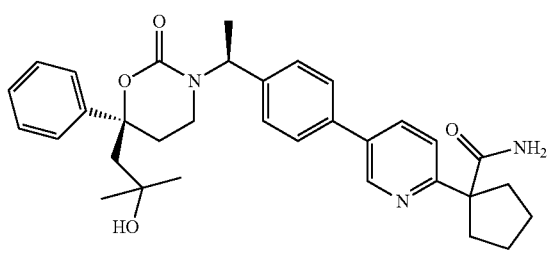 [SMILES: C[C@@H](c1ccc(-c2ccc(C3(C(N)=O)CCCC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclopentanecarboxylic acid amide following a procedure analogous to that described in

EXAMPLE 43

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclohexanecarboxylic acid amide

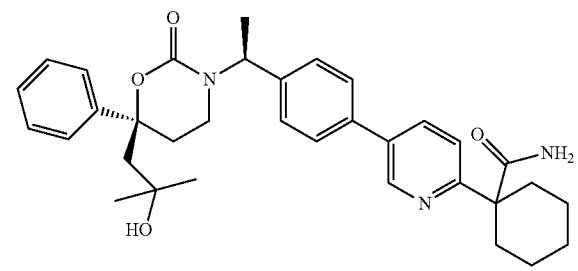

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclohexanecarboxylic acid amide following a procedure analogous to that described in Example 1. Yield: 58% of theory; LC (method 1): $t_R$=2.08 min; Mass spectrum (ESI$^+$): m/z=556 [M+H]$^+$.

EXAMPLE 44

1-[4-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid ethyl ester

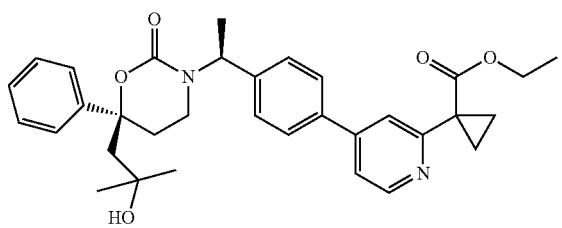 [SMILES: CCOC(=O)C1(c2cc(-c3ccc([C@H](C)N4CC[C@](CC(C)(C)O)(c5ccccc5)OC4=O)cc3)ccn2)CC1]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(4-bromo-pyridin-2-yl)-cyclopropanecarboxylic acid ethyl ester following a procedure analogous to that described in Example 1. Yield: 81% of theory; LC (method 3): $t_R$=2.99 min; Mass spectrum (ESI⁺): m/z=543 [M+H]⁺.

diate 5. Yield: 68% of theory; LC (method 1): $t_R$=2.45 min; Mass spectrum (ESI⁺): m/z=514 [M+H]⁺.

EXAMPLE 45

1-[4-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid

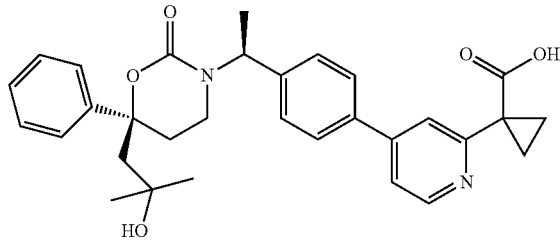 [SMILES: C[C@@H](c1ccc(-c2ccnc(C3(C(=O)O)CC3)c2)cc1)N1CC[C@](CC(C)(C)O)(c2ccccc2)OC1=O]

The title compound was prepared from 1-[4-(4-{(S)-1-[(S)-6-(2-hydroxy-2-methyl-propyl)-2-oxo-6-phenyl-[1,3]oxazinan-3-yl]-ethyl}-phenyl)-pyridin-2-yl]-cyclopropanecarboxylic acid ethyl ester following a procedure analogous to that described in Example 8. Yield: 99% of theory; LC (method 1): $t_R$=1.48 min; Mass spectrum (ESI⁺): m/z=515 [M+H]⁺.

EXAMPLE 46

1-[4-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid amide

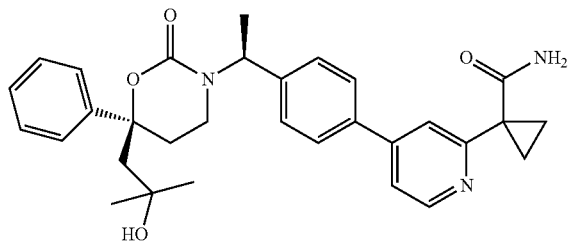 [SMILES: C[C@@H](c1ccc(-c2ccnc(C3(C(N)=O)CC3)c2)cc1)N1CC[C@](CC(C)(C)O)(c2ccccc2)OC1=O]

The title compound was prepared from 1-[4-(4-{(S)-1-[(S)-6-(2-hydroxy-2-methyl-propyl)-2-oxo-6-phenyl-[1,3]oxazinan-3-yl]-ethyl}-phenyl)-pyridin-2-yl]-cyclopropanecarboxylic acid and ammonia (32% in water) following a procedure analogous to that described in Step 2 for Interme-

EXAMPLE 47

1-[4-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid methylamide

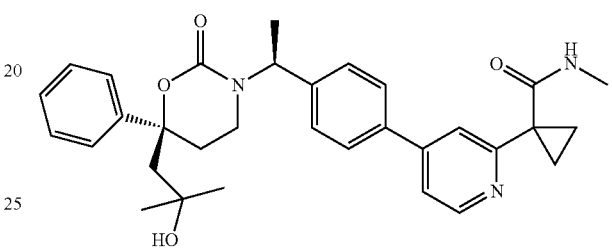

The title compound was prepared from 1-[4-(4-{(S)-1-[(S)-6-(2-hydroxy-2-methyl-propyl)-2-oxo-6-phenyl-[1,3]oxazinan-3-yl]-ethyl}-phenyl)-pyridin-2-yl]-cyclopropanecarboxylic acid and methylamine (2 mol/L in tetrahydrofuran) following a procedure analogous to that described in Step 2 for Intermediate 5. Yield: 59% of theory; LC (method 3): $t_R$=2.57 min; Mass spectrum (ESI⁺): m/z=528 [M+H]⁺.

EXAMPLE 48

1-[4-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclopropanecarboxylic acid dimethylamide

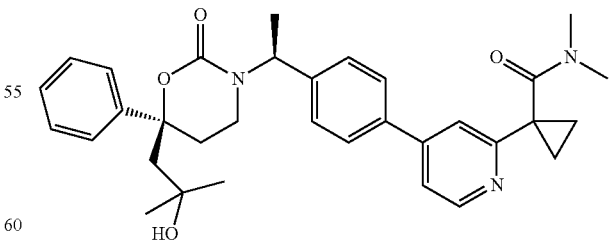

The title compound was prepared from 1-[4-(4-{(S)-1-[(S)-6-(2-hydroxy-2-methyl-propyl)-2-oxo-6-phenyl-[1,3]oxazinan-3-yl]-ethyl}-phenyl)-pyridin-2-yl]-cyclopropanecarboxylic acid and dimethylamine (2 mol/L in tetrahydrofuran) following a procedure analogous to that

EXAMPLE 49

1-[5-(4-{(S)-1-[(S)-4-(2-Hydroxy-2-methyl-propyl)-2-oxo-4-phenyl-tetrahydro-pyrimidin-1-yl]-ethyl}-phenyl)-pyridin-2-yl]-cyclopropanecarboxylic acid amide

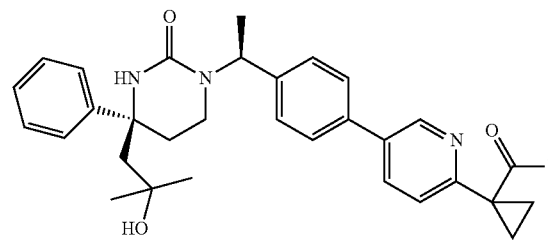

1-(5-Bromo-pyridin-2-yl)-cyclopropanecarboxylic acid amide (120 mg), Na₂CO₃ (443 mg), and Pd(PPh₃)₄ (12 mg) were added to a solution of (S)-4-(2-hydroxy-2-methylpropyl)-4-phenyl-1-{(S)-1-[4-(4,4,5,5-tetramethyl-1,3,2-dioxaborolan-2-yl)phenyl]ethyl}tetrahydro-pyrimidin-2(1H)-one (200 mg; for preparation see WO 2009061498) in ethanol (6 mL), toluene (8 mL), and H₂O (4 mL) at room temperature. The resulting mixture was stirred at 100° C. for 2 h under N₂ atmosphere. After cooling to room temperature, the mixture was concentrated, diluted with H₂O (30 mL), and extracted with ethyl acetate (3×50 mL). The combined organic layers were concentrated to afford an oil which was purified by preparative HPLC to give the title compound. Yield: 124 mg (58% of theory); LC (method 4): $t_R$=0.98 min; Mass spectrum (ESI⁺): m/z=513 [M+H]⁺; ¹H NMR (CDCl₃, 400 MHz) δ 0.69 (s, 3H), 1.29 (m, 2H), 1.31 (m, 3H), 1.50 (d, 3H), 1.79 (m, 2H), 1.98-2.07 (m, 3H), 2.12-2.22 (m, 3H), 2.70-2.83 (m, 1H), 4.55 (s, 1H), 5.80-5.62 (m, 2H), 7.21 (m, 3H), 7.28 (m, 1H), 7.33 (m, 4H), 7.70 (m, 2H), 7.78 (m, 1H) 8.69 (s, 1H).

EXAMPLE 50

4-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-tetrahydro-pyran-4-carboxylic acid amide

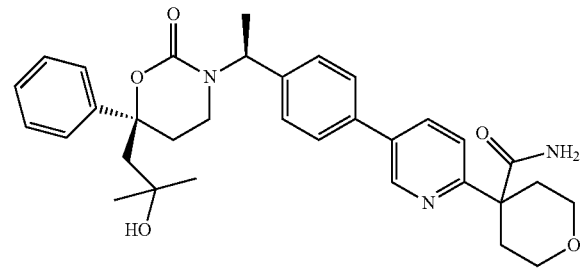 [SMILES: C[C@@H](c1ccc(-c2ccc(C3(C(N)=O)CCOCC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 4-(5-bromo-pyridin-2-yl)-tetrahydro-pyran-4-carboxylic acid amide following a procedure analogous to that described in Example 1. Yield: 97% of theory; LC (method 1): $t_R$=1.81 min; Mass spectrum (ESI⁺): m/z=558 [M+H]⁺.

EXAMPLE 51

1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-cyclobutanecarboxylic acid amide

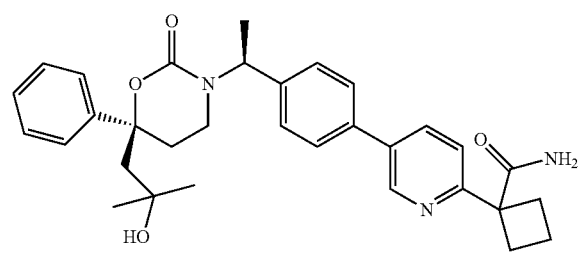 [SMILES: C[C@@H](c1ccc(-c2ccc(C3(C(N)=O)CCC3)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 1-(5-bromo-pyridin-2-yl)-cyclobutanecarboxylic acid amide following a procedure analogous to that described in Example 1. Yield: 41% of theory; LC (method 1): $t_R$=1.94 min; Mass spectrum (ESI⁺): m/z=528 [M+H]⁺.

EXAMPLE 52

(S)-6-(2-Hydroxy-2-methyl-propyl)-3-((S)-1-{4-[6-(1-methyl-2-oxo-pyrrolidin-3-yl)-pyridin-3-yl]-phenyl}-ethyl)-6-phenyl-[1,3]oxazinan-2-one

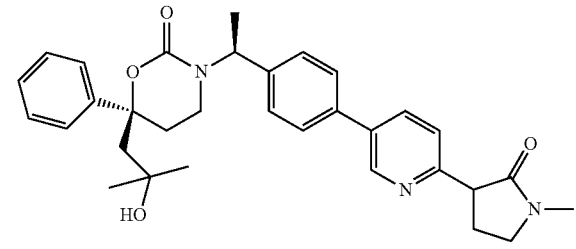 [SMILES: C[C@@H](c1ccc(-c2ccc(C3CCN(C)C3=O)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 3-(5-bromo-pyridin-2-yl)-1-methyl-pyrrolidin-2-one following a procedure analogous to that described in Example 1. Yield: 57% of theory; LC (method 1): $t_R$=1.82 min; Mass spectrum (ESI$^+$): m/z=528 [M+H]$^+$.

EXAMPLE 53

(R)-1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-pyrrolidine-2-carboxylic acid amide

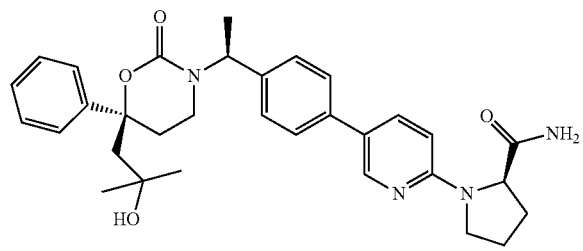 [SMILES: C[C@@H](c1ccc(-c2ccc(N3CCC[C@@H]3C(N)=O)nc2)cc1)N1CC[C@](CC(C)(C)O)(c2ccccc2)OC1=O]

A mixture of 3-{(S)-1-[4-(6-fluoro-pyridin-3-yl)-phenyl]-ethyl}-(S)-6-(2-hydroxy-2-methyl-propyl)-6-phenyl-[1,3]oxazinan-2-one (165 mg), potassium carbonate (76 mg), D-prolinamide (125 mg), and dimethyl sulfoxide (2 mL) was stirred at 100° (overnight. After cooling to room temperature, aqueous NaHCO$_3$ solution was added and the resulting mixture was extracted with dichloromethane. The combined extracts were concentrated and the residue was purified by HPLC on reversed phase (water/methanol) to give the title compound. Yield: 85 mg (43% of theory); Mass spectrum (ESI$^+$): m/z=543 [M+H]$^+$.

EXAMPLE 54

(S)-1-[5-(4-{(S)-1-[(S)-6-(2-Hydroxy-2-methyl-propyl)-2-oxo-6-phenyl-[1,3]oxazinan-3-yl]-ethyl}-phenyl)-pyridin-2-yl]-pyrrolidine-2-carboxylic acid amide

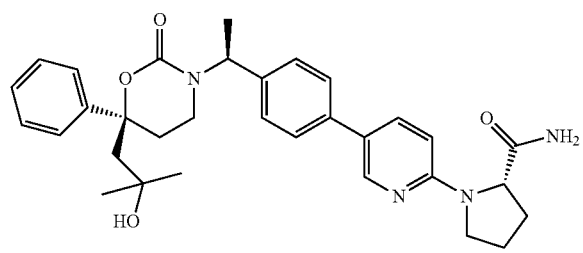 [SMILES: C[C@@H](c1ccc(-c2ccc(N3CCC[C@H]3C(N)=O)nc2)cc1)N1CC[C@](CC(C)(C)O)(c2ccccc2)OC1=O]

The title compound was prepared from 3-{(S)-1-[4-(6-fluoro-pyridin-3-yl)-phenyl]-ethyl}-(S)-6-(2-hydroxy-2-methyl-propyl)-6-phenyl-[1,3]oxazinan-2-one and L-prolinamide following a procedure analogous to that described in Example 53. Yield: 30% of theory; Mass spectrum (ESI$^+$): m/z=543 [M+H]$^+$.

EXAMPLE 55

(R)-1-[6-(4-{(S)-1-[(S)-6-(2-Hydroxy-2-methyl-propyl)-2-oxo-6-phenyl-[1,3]oxazinan-3-yl]-ethyl}-phenyl)-pyridazin-3-yl]-pyrrolidine-2-carboxylic acid amide

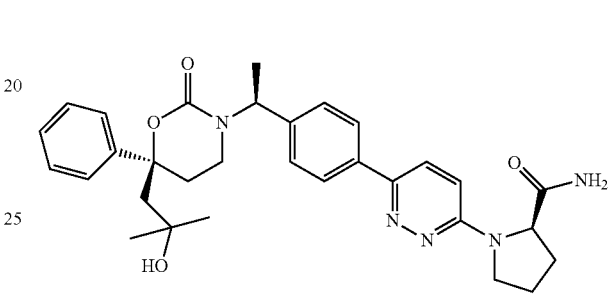

The title compound was prepared from 3-{(S)-1-[4-(6-chloro-pyridazin-3-yl)-phenyl]-ethyl}-(S)-6-(2-hydroxy-2-methyl-propyl)-6-phenyl-[1,3]oxazinan-2-one and D-prolinamide following a procedure analogous to that described in Example 53. Yield: 26% of theory; Mass spectrum (ESI$^+$): m/z=544 [M+H]$^+$.

EXAMPLE 56

3-((S)-1-{4-[6-(3-Hydroxy-1-methyl-2-oxo-pyrrolidin-3-yl)-pyridin-3-yl]-phenyl}-ethyl)-(S)-6-(2-hydroxy-2-methyl-propyl)-6-phenyl-[1,3]oxazinan-2-one

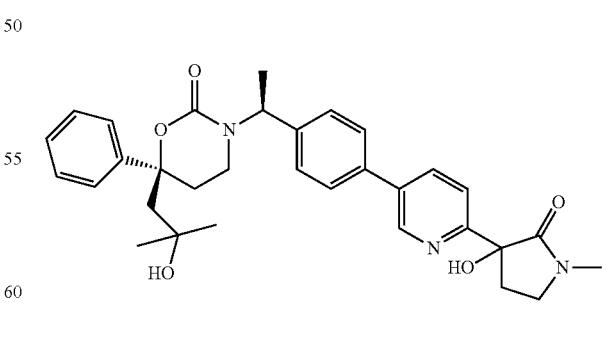

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 3-(5-bromo-pyridin-2-yl)-3-hydroxy-1-methyl-pyrrolidin-2-one following a procedure analogous to that described in Example 1. Yield: 14% of theory; LC (method 3): $t_R$=2.76 min; Mass spectrum (ESI$^+$): m/z=544 [M+H]$^+$.

EXAMPLE 57

3-((S)-1-{4-[6-(1,3-Dimethyl-2-oxo-pyrrolidin-3-yl)-pyridin-3-yl]-phenyl}-ethyl)-(S)-6-(2-hydroxy-2-methyl-propyl)-6-phenyl-[1,3]oxazinan-2-one

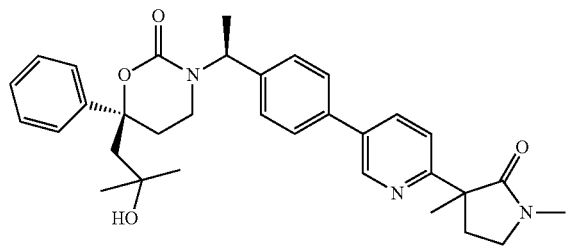 [SMILES: C[C@@H](c1ccc(-c2ccc(C3(C)CCN(C)C3=O)nc2)cc1)N1CC[C@](CC(C)(C)O)(c2ccccc2)OC1=O]

The title compound was prepared from (S)-6-(2-hydroxy-2-methylpropyl)-6-phenyl-3-{(S)-1-[4-(4,4,5,5-tetramethyl-1,3,2-dioxaborolan-2-yl)phenyl]-ethyl}-1,3-oxazinan-2-one and 3-(5-bromo-pyridin-2-yl)-1,3-dimethyl-pyrrolidin-2-one following a procedure analogous to that described in Example 1. Yield: 65% of theory; LC (method 3): $t_R$=3.06 min; Mass spectrum (ESI$^+$): m/z=542 [M+H]$^+$.

EXAMPLE 58

(S)-6-(2-Hydroxy-2-methyl-propyl)-3-{(S)-1-[4-(1-oxetan-3-yl-6-oxo-1,6-dihydro-pyridin-3-yl)-phenyl]-ethyl}-6-phenyl-[1,3]oxazinan-2-one

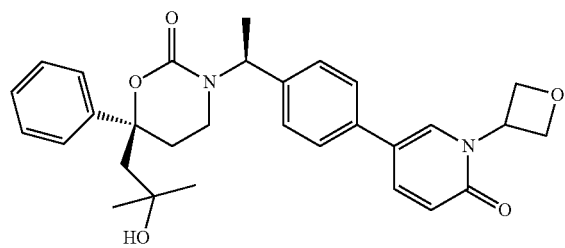 [SMILES: C[C@@H](c1ccc(-c2ccc(=O)n(C3COC3)c2)cc1)N1CC[C@](CC(C)(C)O)(c2ccccc2)OC1=O]

The title compound was prepared from (S)-6-(2-hydroxy-2-methyl-propyl)-6-phenyl-3-{(S)-1-[4-(4,4,5,5-tetramethyl-1,3,2-dioxaborolan-2-yl)phenyl]-ethyl}-1,3-oxazinan-2-one and 5-bromo-1-oxetan-3-yl-1H-pyridin-2-one following a procedure analogous to that described in Example 35. LC (method 4): $t_R$=0.97 min; Mass spectrum (ESI$^+$): m/z=503 [M+H]$^+$; $^1$H NMR (CDCl$_3$) δ 1.05 (s, 3H), 1.12 (s, 3H), 1.48 (d, 3H), 2.10-2.22 (m, 5H), 2.34 (m, 1H), 2.83 (m, 1H), 4.72 (m, 2H), 5.10 (m, 2H), 5.63 (m, 1H), 5.83 (m, 1H), 6.57 (d, 1H), 6.97 (d, 2H), 7.12 (d, 2H), 7.20-7.32 (m, 5H), 7.49 (d, 1H), 7.65 (s, 1H).

EXAMPLE 59

1-[5-(4-{(S)-1-[(S)-6-Cyclopropylmethyl-6-(2-hydroxy-2-methyl-propyl)-2-oxo-[1,3]oxazinan-3-yl]-ethyl}-phenyl)-pyridin-2-yl]-cyclopropanecarboxylic acid amide

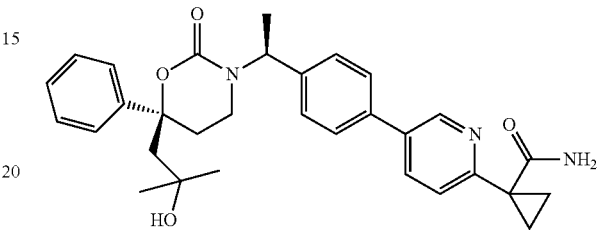

Tetrakis(triphenylphosphine)palladium(0) (3.3 mg) was added to a solution of (S)-6-(cyclopropylmethyl)-6-(2-hydroxy-2-methylpropyl)-3-{(S)-1-[4-(4,4,5,5-tetramethyl-1,3,2-dioxaborolan-2-yl)phenyl]ethyl}-1,3-oxazinan-2-one (150 mg), 1-(5-bromopyridin-2-yl)cyclopropanecarboxamide (94 mg), and Na$_2$CO$_3$ (348 mg, 3.28 mmol) in ethanol (8 mL), toluene (12 mL), and H$_2$O (4 mL) at room temperature. The reaction mixture was heated to 100° C. for 2 h. After cooling to room temperature, the formed mixture was concentrated to afford an oil which was diluted with H$_2$O (30 mL) and extracted with ethyl acetate (3×50 mL). The combined organic layer was concentrated to afford an oil which was purified by preparative TLC and preparative HPLC to give the title compound. Yield: 30 mg (19% of theory); LC (method 4): $t_R$=0.95 min, Mass spectrum (ESI$^+$): m/z=492 [M+H]$^+$; $^1$H NMR (CDCl$_3$, 400 MHz) δ 0.01 (d, 2H), 0.40-0.50 (m, 2H), 0.69 (m, 1H), 1.27 (m, 2H), 1.33 (s, 3H), 1.39 (s, 3H), 1.61 (d, 3H), 1.78 (m, 1H), 1.82 (m, 2H), 1.89-2.05 (m, 4H), 2.21 (m, 1H), 2.80 (m, 1H), 3.19 (m, 1H), 5.51 (1H), 5.85 (m, 1H), 7.29 (m, 1H), 7.48 (d, 2H), 7.58 (d, 2H), 7.82 (1H), 7.89 (d, 1H), 8.79 (s, 1H).

Some examples of formulations will now be described in which the term "active substance" denotes one or more compounds according to the invention, including the salts thereof. In the case of one of the combinations with one or additional active substances as described previously, the term "active substance" also includes the additional active substances.

EXAMPLE A

Tablets Containing 100 Mg of Active Substance
Composition:
  1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE B

Tablets Containing 150 Mg of Active Substance
Composition:
1 tablet contains:

| active substance | 150.0 mg |
|---|---|
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE C

Hard Gelatine Capsules Containing 150 Mg of Active Substance
Composition:
1 capsule contains:

| active substance | 150.0 mg |
|---|---|
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE D

Suppositories Containing 150 Mg of Active Substance
Composition:
1 suppository contains:

| active substance | 150.0 mg |
|---|---|
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 Mg Active Substance
Composition:

| active substance | 10.0 mg |
|---|---|
| 0.01N hydrochloric acid | q.s. |
| double-distilled water | ad 2.0 mL |

Preparation:

The active substance is dissolved in the necessary amount of 0.01 N HCl, made isotonic with common salt, filtered sterile and transferred into 2 mL ampoules.

EXAMPLE F

Ampoules Containing 50 Mg of Active Substance
Composition:

| active substance | 50.0 mg |
|---|---|
| 0.01N hydrochloric acid | q.s. |
| double-distilled water | ad 10.0 mL |

Preparation:

The active substance is dissolved in the necessary amount of 0.01 N HCl, made isotonic with common salt, filtered sterile and transferred into 10 mL ampoules.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula:

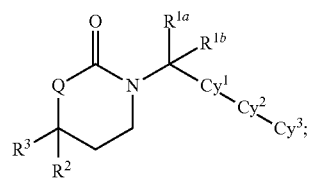

I or a pharmaceutically acceptable salt thereof, wherein:

$Cy^1$ is aryl, heteroaryl, cycloalkyl, or heterocyclyl, each of which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)O—C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O—C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

$Cy^2$ is aryl, heteroaryl, cycloalkyl, or heterocyclyl, each of which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, —$C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$;

$Cy^3$ is cycloalkyl, which is substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$C(=O)NH_2$, —$S(=O)_2NH_2$, —$C(=O)NHR^6$, —$C(=O)NR6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$V^1$—$S(=O)_2R^6$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, carboxy-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$; or heterocyclyl, which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$V^1$—$S(=O)_2R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2 N(R^7)_2$, cyano-$C_{1-6}$-alkyl, carboxy-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$, and —$V^1$—$C(=O)N(R^7)_2$; or aryl or heteroaryl;

$R^{1a}$, $R^{1b}$ independently of each other are hydrogen, $C_{1-6}$-alkyl, $C_{3-6}$-cycloalkyl, $C_{2-6}$-alkenyl, $C_{2-6}$-alkynyl or $C_{1-3}$-alkyloxy-$C_{1-3}$-alkyl, or $R^{1a}$ and $R^{1b}$ are joined and, together with the carbon atom they are attached, form a $C_{3-6}$-cycloalkyl group, wherein the above-mentioned $C_{1-6}$-alkyl, $C_{2-6}$-alkenyl, $C_{2-6}$-alkynyl, $C_{1-3}$-alkoxy-$C_{1-3}$-alkyl, and $C_{3-6}$-cycloalkyl groups are optionally substituted with one to three groups independently selected from fluorine, cyano, $C_{1-6}$-alkyl, oxo and hydroxy;

$R^2$ is $C_{1-6}$-alkyl, aryl, heteroaryl, cycloalkyl, or heterocyclyl, each of which is optionally substituted with 1 to 4 groups independently selected from halogen, cyano, nitro, amino, hydroxy, carboxy, $C_{1-6}$-alkyl, $C_{2-6}$-alkenyl, $C_{2-6}$-alkynyl, $C_{1-6}$-alkoxy, $C_{3-6}$-cycloalkyl, $C_{3-6}$-cycloalkoxy, hydroxy-$C_{1-6}$-alkyl, hydroxy-$C_{3-6}$-cycloalkyl, hydroxy-$C_{2-6}$-alkenyl, hydroxy-$C_{1-6}$-alkoxy, —$R^9$, $C_{4-7}$-cycloalkyl-$C_{1-6}$-alkoxy, halo-$C_{1-6}$-alkoxy, halo-$C_{3-6}$-cycloalkoxy, halo-$C_{4-7}$-cycloalkyl-$C_{1-6}$-alkoxy, $C_{1-6}$-alkoxy-$C_{1-6}$-alkoxy, halo-$C_{1-6}$-alkoxy-$C_{1-6}$-alkoxy, $C_{1-6}$-alkylthio, $C_{3-6}$-cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)O$—$C_{1-6}$-alkyl, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)O$—$C_{1-6}$-alkyl, —$V^1$—$NHC(=O)R^6$, —$V^1$—$NHC(=O)O$—$C_{1-6}$-alkyl, —$NHS(=O)_2R^6$, —$V^1$—$NHS(=O)_2R^6$, —$V^1$—$C(=O)R^6$, —$V^1$—$C(=O)O$—$C_{1-6}$-alkyl, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)O$—$C_{3-6}$-cycloalkyl, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano-$C_{1-6}$-alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

$R^3$ is $C_{1-6}$alkyl, $C_{2-6}$-alkenyl, $C_{2-6}$-alkynyl, $C_{3-5}$-cycloalkyl-$C_{1-4}$-alkyl, $C_{1-3}$-alkoxy-$C_{1-3}$-alkoxy, or $C_{1-3}$-alkoxy-$C_{1-3}$-alkyl, each of which is optionally substituted with one to four groups independently selected from fluorine, cyano, oxo, —$R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, spirocycloalkyl, heterocyclyl (which in turn is optionally substituted with $C_{1-4}$-alkyl, halo-$C_{1-4}$-alkyl, halogen, or oxo), heteroaryl (which in turn is optionally substituted with $C_{1-4}$-alkyl, halo-$C_{1-4}$-alkyl, $C_{1-4}$-alkoxy, $C_{1-4}$-alkylthio, $C_{1-4}$-alkylsulfonyl, halogen, trifluoromethyl, di($C_{1-3}$-alkyl)amino, nitro, cyano, carboxy, aminocarbonyl, $C_{1-4}$-alkylaminocarbonyl, di($C_{1-3}$-alkyl)aminocarbonyl, or oxo), arylamino (which in turn is optionally substituted with $C_{1-4}$-alkyl, $C_{1-4}$-alkoxy, $C_{1-4}$-alkylthio, $C_{1-4}$-alkylsulfonyl, halogen, trifluoromethyl, di($C_{1-4}$-alkyl)amino, nitro, cyano, carboxy, aminocarbonyl, $C_{1-4}$-alkylaminocarbonyl, and di($C_{1-3}$-alkyl)aminocarbonyl) and heteroarylamino (which in turn is optionally substituted with $C_{1-4}$-alkyl, halo-$C_{1-4}$-alkyl, $C_{1-4}$-alkoxy, $C_{1-4}$-alkylthio, $C_{1-4}$-alkylsulfonyl, halogen, trifluoromethyl, di($C_{1-3}$-alkyl)amino, nitro, cyano, carboxy, aminocarbonyl, $C_{1-4}$-alkylaminocarbonyl, di($C_{1-3}$-alkyl)aminocarbonyl, or oxo);

$R^4$ is independently selected from hydrogen, $C_{1-6}$-alkyl and halo-$C_{1-6}$-alkyl $R^6$ is independently selected from $C_{1-6}$-alkyl, $C_{2-6}$-alkenyl, and $C_{2-6}$-alkynyl;

$R^7$ is $C_{3-6}$-cycloalkyl;

$R^8$ is heterocyclyl;

$R^9$ is $C_{4-7}$-cycloalkyl-$C_{1-6}$-alkyl, $C_{3-6}$-cycloalkyl-$C_{2-4}$-alkynyl, halo-$C_{1-6}$-alkyl, halo-$C_{2-6}$-alkenyl, halo-$C_{3-6}$-cycloalkyl, halo-$C_{4-7}$-cycloalkyl-$C_{1-6}$-alkyl, $C_{1-6}$-alkoxy-$C_{1-6}$-alkyl, or halo-$C_{1-6}$-alkoxy-$C_{1-6}$-alkyl;

Q is NH; and $V^1$ is independently selected from $C_{1-6}$-alkylene, $C_{2-6}$-alkenylene, $C_{2-6}$-alkynylene, and $C_{1-6}$-alkyleneoxy.

2. The compound of claim 1, wherein:

$Cy^3$ is $C_{3-6}$-cycloalkyl, which is mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl, or 2-oxo-1,2-dihydropyridinyl, which is optionally mono- or disubstituted independently of each other with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl -$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl -aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl.

3. The compound of claim 2, wherein:

$Cy^1$ is cyclohexyl, piperidinyl, phenyl, thienyl, thiazolyl, thiadiazolyl, pyridyl, pyridazinyl, pyrazinyl, pyrimidinyl, benzimidazolyl, indazolyl, benzothiazolyl and benzotriazolyl, each of which is optionally substituted with 1 or 2 groups independently selected from halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy, and halo-$C_{1-4}$-alkoxy;

$Cy^2$ is phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl or 1,1-dioxohexahydro-1,2-thiazinyl, each of which is optionally substituted with 1 or 2 groups independently selected from halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy;

$Cy^3$ is $C_{3-6}$-cycloalkyl, which is mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or 2-oxo-1,2-dihydropyridinyl, which is optionally mono- or disubstituted independently of each other with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl;

$R^{1a}$ and $R^{1b}$ are independently of each other hydrogen, $C_{1-4}$-alkyl, cyclopropyl or methoxymethyl;

$R^2$ is phenyl, fluorophenyl, $C_{1-4}$-alkyl, trifluoroethyl, cyclopropyl or cyclopropylmethyl; and $R^3$ is methyl, ethyl, propyl, butyl, vinyl, allyl or ethoxyethyl, each of which is optionally substituted with one or two groups independently selected from methyl, cyano, aminocarbonyl, methylaminocarbonyl, dimethylaminocarbonyl, hydroxymethylcarbonylamino, 2-oxo-pyrrolidin-1-yl, carboxy, amino, methylamino, dimethylamino, acetylamino, aminocarbonylamino, methylaminocarbonylamino, ethylaminocarbonylamino, N-methyl-N-methylcarbonyl-amino, methlysulfonylamino, N-methyl-N-methylsulfonyl-amino, hydroxy, methoxy, 2-hydroxyethoxy, aminocarbonyloxy, methylsulfanyl, methylsulfinyl and methylsulfonyl.

4. The compound of any one of claim 3, wherein:
$Cy^1$ is cyclohexyl, piperidinyl, phenyl or pyrimidinyl, each of which is optionally substituted with 1 or 2 groups independently selected from halogen, cyano, $C_{1-6}$-alkyl and $C_{1-6}$-alkoxy;
$Cy^2$ is phenyl, pyrazolyl, thiazolyl, pyridinyl, pyridazinyl, 2-oxo-1,2-dihydropyridinyl or pyrimidinyl, each of which is optionally substituted with 1 or 2 groups independently selected from halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy;
$Cy^3$ is $C_{3-6}$-cycloalkyl, which is monosubstituted with cyano, aminocarbonyl, methylaminocarbonyl, dimethylaminocarbonyl, carboxy, ethoxycarbonyl, methylsulfonyl, or azetidinyl, oxetanyl, pyrrolidinyl, 2-oxo-pyrrolidinyl, tetrahydrofuranyl, piperidinyl, 2-oxo-piperidinyl, tetrahydropyranyl, 2-oxo-imidazolidinyl, or morpholinyl, each of which is optionally mono- or disubstituted with a group independently selected from fluorine, methyl, aminocarbonyl and hydroxy, or 1,2-dihydropyridin-2-on-yl, which is optionally monosubstituted with a group selected from fluorine and methyl;
$R^{1a}$ is methyl, ethyl or cyclopropyl and $R^{1b}$ is hydrogen;
$R^2$ is phenyl, fluorophenyl or cyclopropylmethyl; and
$R^3$ is 2-methylallyl, 2-aminocarbonylethyl, 2-aminocarbonyl-2-methyl-propyl, 3-methylsulfonylamino-propyl, 2-hydroxyethyl, 2-hydroxy-2-methylpropyl, 3-hydroxypropyl, 3-hydroxy-3-methylbutyl or 2-cyano-2-methylpropyl.

5. The compound of any one of claim 4, wherein:
$Cy^1$ is phenyl;
$Cy^2$ is phenyl, pyrazolyl, thiazolyl, pyridinyl, pyridazinyl, 2-oxo-1,2-dihydropyridinyl, or pyrimidinyl;
$Cy^3$ is 1-cyano-cyclopropyl, 1-ethoxycarbonyl-cyclopropyl, 1-carboxy-cyclopropyl, 1-aminocarbonyl-cyclopropyl, 1-methylaminocarbonyl-cyclopropyl, 1-dimethylaminocarbonyl-cyclopropyl, 1-methylsulfonyl-cyclopropyl, 1-aminocarbonyl-cyclobutyl, 1-aminocarbonyl-cyclopentyl, 1-aminocarbonyl-cyclohexyl, 4-aminocarbonyl-tetrahydropyran-4-yl, azetidin-1-yl, azetidin-3-yl, 3-hydroxy-azetidin-1-yl, 3-fluoro-azetidin-1-yl, 3,3-difluoro-azetidinyl, oxetan-3-yl, 3-hydroxy-oxetan-3-yl, 2-aminocarbonyl-pyrrolidin-1-yl, tetrahydrofuran-3-yl, tetrahydropyran-4-yl, pyrrolidin-2-on-1-yl, 1-methyl-pyrrolidin-2-on-3-yl, 1,3-dimethyl-pyrrolidin-2-on-3-yl, 3-hydroxy-1-methyl-pyrrolidin-2-on-3-yl, 2-oxo-imidazolidin-1-yl, 3-methyl-2-oxo-imidazolidin-1-yl, morpholin-4-yl, piperidin-2-on-1-yl, or 1,2-dihydropyridin-2-on-1-yl;
$R^{1a}$ is methyl and $R^{1b}$ is hydrogen;
$R^2$ is phenyl; and
$R^3$ is 2-hydroxy-2-methyl-propyl.

6. The compound of any one of claim 4, wherein $Cy^1$ is phenyl.

7. The compound of any one of claim 3, wherein $R^2$ is phenyl, fluorophenyl or cyclopropylmethyl.

8. The compound of claim 1, wherein:
$R^{1a}$ is methyl, ethyl or cyclopropyl and $R^{1b}$ is hydrogen;
$R^3$ is 2-methylallyl, 2-aminocarbonylethyl, 2-aminocarbonyl-2-methyl-propyl, 3-methylsulfonylamino-propyl, 2-hydroxyethyl, 2-hydroxy-2-methylpropyl, 3-hydroxypropyl, 3-hydroxy-3-methylbutyl or 2-cyano-2-methylpropyl;
$Cy^1$ is phenyl;
$Cy^2$ is phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl or 1,1-dioxo-hexahydro-1,2-thiazinyl, each of which is optionally substituted with 1 or 2 groups independently selected from halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy;
$Cy^3$ is $C_{3-6}$-cycloalkyl, which is mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$- alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl, or 2-oxo-1,2-dihydropyridinyl, which is optionally mono- or disubstituted independently of each other with a group independently selected from fluorine, fluoro-$C_{1-4}$-alkyl-, difluoro-$C_{1-4}$-alkyl-, trifluoro-$C_{1-4}$-alkyl-, $C_{1-4}$-alkyl, cyano, cyano-$C_{1-4}$-alkyl-, aminocarbonyl, aminocarbonyl-$C_{1-4}$-alkyl-, $C_{1-4}$-alkylaminocarbonyl, $C_{1-4}$-alkylaminocarbonyl-$C_{1-4}$-alkyl-, di-$C_{1-4}$-alkyl-aminocarbonyl, di-$C_{1-4}$-alkylaminocarbonyl-$C_{1-4}$-alkyl-, carboxy, carboxy-$C_{1-4}$-alkyl-, $C_{1-4}$-alkoxy-carbonyl, $C_{1-4}$-alkoxy-carbonyl-$C_{1-4}$-alkyl-, hydroxy, hydroxy-$C_{1-4}$-alkyl, $C_{1-4}$-alkoxy, $C_{1-4}$-alkoxy-$C_{1-4}$-alkyl, $C_{1-4}$-alkylsulfonyl and $C_{1-4}$-alkylsulfonyl-$C_{1-4}$-alkyl; and $R^{1a}$ is methyl, ethyl or cyclopropyl and $R^{1b}$ is hydrogen.

9. The compound of any one of claim 8, wherein $Cy^2$ is phenyl, pyrazolyl, thiazolyl, pyridinyl, pyridazinyl, 2-oxo-1,2-dihydropyridinyl or pyrimidinyl, each of which is optionally substituted with 1 or 2 groups independently selected from halogen, cyano, hydroxy, $C_{1-6}$-alkyl, halo-$C_{1-4}$-alkyl, $C_{2-6}$-alkenyl, $C_{2-6}$-alkynyl, $C_{1-6}$-alkoxy and halo-$C_{1-4}$-alkoxy.

10. The compound of claim 9, wherein $Cy^3$ is $C_{3-6}$-cycloalkyl, which is mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or azetidinyl, oxetanyl, pyrrolidinyl, tetrahydrofuranyl, piperidinyl, tetrahydropyranyl, imidazolidinyl, piperazinyl, or morpholinyl, in each of which one $CH_2$ group is optionally replaced by carbonyl and each of which is optionally mono- or disubstituted with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl, or 2-oxo-1,2-dihydropyridinyl, which is optionally mono- or disubstituted independently of each other with a group independently selected from fluorine, $C_{1-4}$-alkyl, cyano, aminocarbonyl, $C_{1-4}$-alkylaminocarbonyl, di-$C_{1-4}$-alkyl-aminocarbonyl, carboxy, $C_{1-4}$-alkoxy-carbonyl, hydroxy, $C_{1-4}$-alkoxy and $C_{1-4}$-alkylsulfonyl.

11. The compound of claim 10, wherein:
$R^{1a}$ is methyl and $R^{1b}$ is hydrogen; and
$R^3$ is 2-hydroxy-2-methyl-propyl.

12. The compound of claim 10, wherein:
$Cy^3$ is $C_{3-6}$-cycloalkyl, which is monosubstituted with cyano, aminocarbonyl, methylaminocarbonyl, dimethylaminocarbonyl, carboxy, ethoxycarbonyl, methylsulfonyl, or azetidinyl, oxetanyl, pyrrolidinyl, 2-oxo-pyrrolidinyl, tetrahydrofuranyl, piperidinyl, 2-oxo-piperidinyl, tetrahydropyranyl, 2-oxo-imidazolidinyl, or morpholinyl, each of which is optionally mono- or disubstituted with a group independently selected from fluorine, methyl, aminocarbonyl and hydroxy, or 1,2-dihydropyridin-2-on-yl, which is optionally monosubstituted with a group selected from fluorine and methyl; and
$R^3$ is 2-hydroxy-2-methyl-propyl.

13. A method of treating a subject with a disease or disorder selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome, comprising the step of administering to the subject an effective amount of the compound of claim 1, or a pharmaceutically acceptable salt thereof.

14. A pharmaceutical composition comprising: i) a pharmaceutically acceptable carrier or diluent; and ii) the compound of claim 1; or a pharmaceutically acceptable salt, thereof.

15. The compound of claim 1, wherein the compound is 1-[5-(4-{(S)-1-[(S)-4-(2-Hydroxy-2-methyl-propyl)-2-oxo-4-phenyl-tetrahydro-pyrimidin-1-yl]-ethyl}-phenyl)-pyridin-2-yl]-cyclopropanecarboxylic acid amide, or a pharmaceutically acceptable salt thereof.

16. A pharmaceutical composition comprising: i) a pharmaceutically acceptable carrier or diluent; and ii) the compound of claim 15; or a pharmaceutically acceptable salt thereof.

17. A method of treating a subject with a disease or disorder selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome, comprising the step of administering to the subject an effective amount of the compound of claim 15, or a pharmaceutically acceptable salt thereof.

* * * * *